US007479482B2

(12) United States Patent
Frangione et al.

(10) Patent No.: US 7,479,482 B2
(45) Date of Patent: Jan. 20, 2009

(54) SYNTHETIC IMMUNOGENIC BUT NON-DEPOSIT-FORMING POLYPEPTIDES AND PEPTIDES HOMOLOGOUS TO AMYLOID β, PRION PROTEIN, AMYLIN, α-SYNUCLEIN, OR POLYGLUTAMINE REPEATS FOR INDUCTION OF AN IMMUNE RESPONSE THERETO

(75) Inventors: Blas Frangione, New York, NY (US); Thomas Wisniewski, Statent Island, NY (US); Einar M. Sigurdsson, New York, NY (US)

(73) Assignee: New York University, New York, NY (US)

( * ) Notice: Subject to any disclaimer, the term of this patent is extended or adjusted under 35 U.S.C. 154(b) by 267 days.

(21) Appl. No.: 10/301,488

(22) Filed: Nov. 21, 2002

(65) Prior Publication Data

US 2003/0166558 A1 Sep. 4, 2003

Related U.S. Application Data

(60) Provisional application No. 60/331,801, filed on Nov. 21, 2001.

(51) Int. Cl.
*A61K 38/16* (2006.01)
*C07K 14/00* (2006.01)
*C07K 19/00* (2006.01)
(52) U.S. Cl. .......................... 514/12; 530/300; 530/350
(58) Field of Classification Search ................. None
See application file for complete search history.

(56) References Cited

U.S. PATENT DOCUMENTS

| 5,843,446 | A  | 12/1998 | Ladd et al. ............... 424/184.1 |
| 5,948,763 | A  | 9/1999  | Soto-Jara et al. ............... 514/14 |
| 6,274,615 | B1 | 8/2001  | Pappolla et al. ............. 514/415 |
| 6,462,171 | B1 | 10/2002 | Soto-Jara et al. ............ 530/326 |
| 6,713,450 | B2 | 3/2004  | Frangione et al. |

FOREIGN PATENT DOCUMENTS

| EP | 0 908 727 | * | 4/1999 |
| WO | 93/23432  |   | 11/1993 |
| WO | 95/31996  |   | 11/1995 |
| WO | 96/39834  |   | 12/1996 |
| WO | 99/27944  |   | 6/1999  |
| WO | 99/27949  |   | 6/1999  |
| WO | 99/48489  |   | 9/1999  |
| WO | 00/71671  |   | 11/2000 |
| WO | 00/72880  |   | 12/2000 |
| WO | 01/90182  |   | 11/2001 |
| WO | 03/044051 | * | 5/2003  |

OTHER PUBLICATIONS

Benkirane 1993. Journal of Biological Chemistry 268:26279-26285.*
Bodles 2001. Journal of Neurochemistry 78:384-395.*
Conway 2000. Biochemistry 39:2552-2563.*
Lowenadler 1990. European Journal of Immunology 20:1541-1545.*
Van Regenmortel et al. 1998. Current Opinion in Biotechnology 9:377-382.*
Aguado et al., Vaccine (1999) 17:2321-2328.
Biere et al., J Biol Chem (2000) 275:34574-34579.
Büeler et al., Cell (1993) 73:1339-1347.
Büeler et al., Nature (1992) 356:577-582.
Buschle et al., Proc. Natl. Acad. Sci. USA (1997) 94:3256-3261.
Calero et al., J. of Neurochemistry (2001) 77:628-637.
Chesebro et al., Nature (1985) 315:331-333.
Deierkauf et al., J. Cell Physiol. (1977) 92:169-175.
Di Nicola et al., Brit. J. of Haematology (2000) 111:344-350.
Farmer et al., Cell. Immunology (1993) 146:198-209.
Findeis, Biochim Biophys Acta (2000) 1502:76-84.
Frenkel et al., Neuroimmunomodulation (1999) 6:444 (P43).
Futaki et al., J. of Biological Chem. (2001) 276:5836-40.
Ghetti et al., Mol Neurobiol (1994) 8:41-48.
Ghetti et al., Proc Natl Acad Sci USA (1996) 93:744-748.
Giasson et al., Neuron (2002) 34:521-533.
Goedert, Nat Rev Neurosci (2001) 2:492-501.
Horwich et al., Cell (1997) 89:499-510.
Hsiao et al., Proc Natl Acad Sci USA (1994) 91:9126-9130.
Johnson et al., N Engl J Med (1989) 321:513-518.
Kaytor et al., J Biol Chem (1999) 274:37507-37510.
Kisilevsky, Drugs & Aging (1996) 8:75-83.
Kretzschmar et al., Am J Pathol (1986) 122:1-5.
Martinez-Fong et al., Hepatology, (1994) 20:1602-1608.
Moriarty et al., Biochemistry (1999) 38:1811-1818.
Oesch et al., Cell (1985) 40:735-746.
Pallitto et al., Biochemistry (1999) 38:3570-3578.
Peterson et al., Infection and Immunity (1984) 43:561-566.
Prusiner et al., Cell (1998) 93:337-348.
Prusiner et al., Proc Natl Acad Sci USA (1993) 90:10608-10612.
Rubinsztein et al., J Med Genet (1999) 36:265-270.
Schenk et al., Nature (1999) 400:173-177.
Schwarzenberger et al., Amer. J. of the Medical Sciences (2001) 321:129-136.
Serpell et al., Proc Natl Acad Sci USA (2000) 97:4897-4902.
Shen et al., J. of Biol. Chem. (1985) 260:10905-10908.
Sigurdsson et al., Amer. Journal of Pathology (2001) 159:439-447.
Sigurdsson et al., Amer. Journal of Pathology (2002) 161:13-17.

(Continued)

*Primary Examiner*—Daniel E. Kolker
(74) *Attorney, Agent, or Firm*—Darby & Darby P.C.

(57) ABSTRACT

The present invention relates to immunogenic but non-depositing-forming polypeptides or peptides homologous to amyloid β, prion, amylin or α-synuclein which can be used alone or conjugated to an immunostimulatory molecule in an immunizing composition for inducing an immune response to amyloid β peptides and amyloid deposits, to prion protein and prion deposits, to amylin and amylin deposits, to α-synuclein and deposits containing α-synuclein, or to polyglutamine repeats and deposits of proteins containing polyglutamine repeats. Described are also antibodies directed against such peptides, their generation, and their use in methods of passive immunization to such peptides and deposits.

8 Claims, 33 Drawing Sheets

OTHER PUBLICATIONS

Sigurdsson et al., Drug Development Research (2002) 56:135-142.
Sigurdsson et al., J. of Neuropathology and Exp. Neurology (2000) 59:11-17.
Sigurdsson et al., Trends in Mol. Medicine (2002) 8:411-413.
Solomon et al., Proc. Natl. Acad. Sci. USA, (1997) 94:4109-4112.
Soto et al., Lancet (2000) 355:192-197.
Soto et al., Nat Med (1998) 4:822-826.
Spillantini et al., Nature (1997) 388:839-840.
Taglivini et al., Proc. Natl. Acad. Sci. USA, (1993) 90:9678-9682.
Telling et al., Genes & Dev (1996) 10:1736-1750.
Wang et al., J. of Pathology (1989) 159:159-167.
Westermark et al., Proc Natl Acad Sci USA (1990) 87:5036-5040.
Wisniewski and Sigurdsson, Curr Neur. and Neurosci. Rpts (2002) 2:400-404.
Wisniewski et al., Biochemical Society (2002) 30:574-578.
Wood et al., Biochemistry (1995) 34:724-730.
Poduslo et al., "β-Sheet Breaker Peptide Inhibitor of Alzheimer's Amyloidogenesis with Increased Blood-Brain Barrier Permeability and Resistance to Proteolytic Degradation in Plasma", J. Neurobiol., 1999, p. 375, second column, first complete paragraph.

* cited by examiner

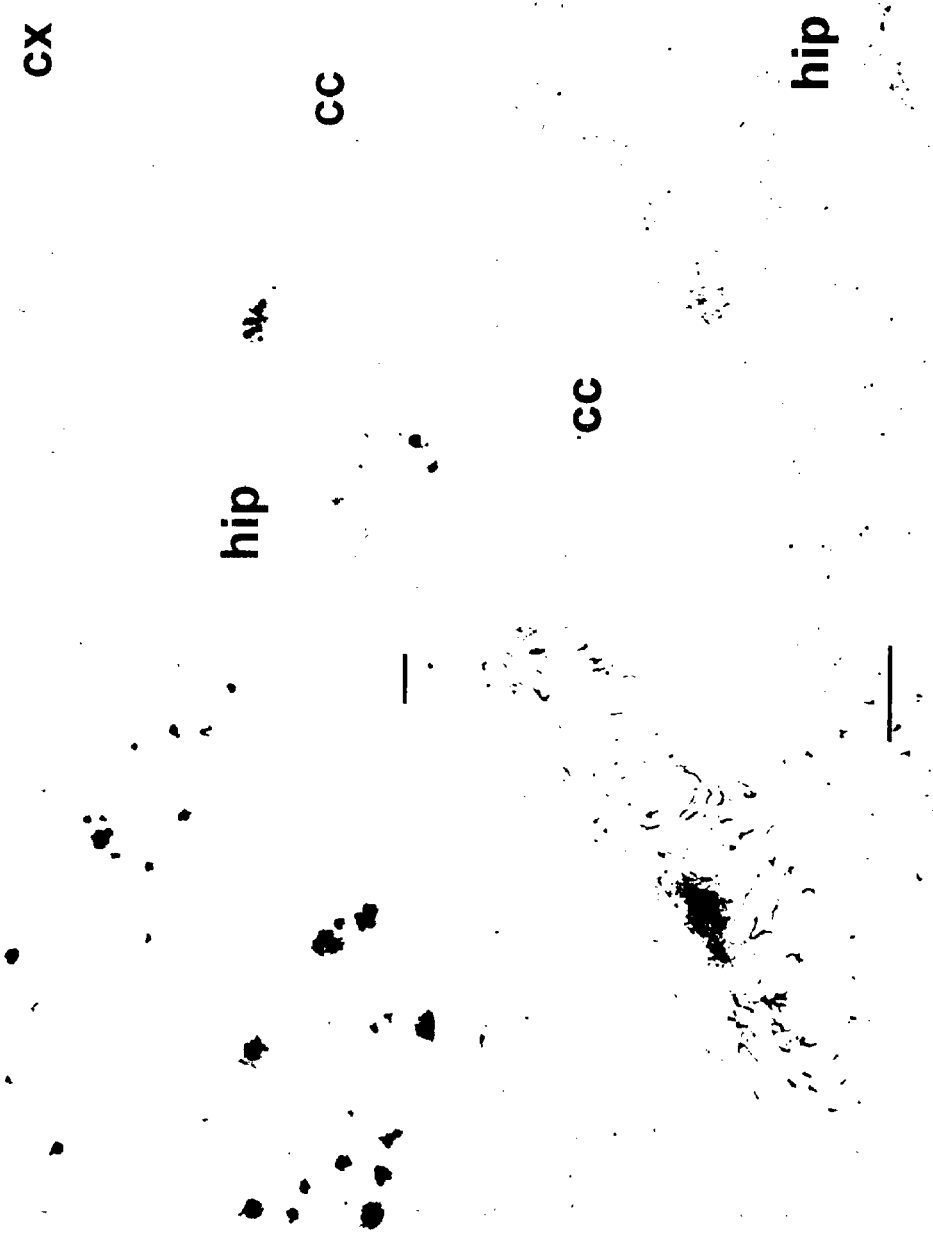

SYNTHETIC IMMUNOGENIC BUT NON-DEPOSIT-FORMING POLYPEPTIDES AND PEPTIDES HOMOLOGOUS TO AMYLOID β, PRION PROTEIN, AMYLIN, α-SYNUCLEIN, OR POLYGLUTAMINE REPEATS FOR INDUCTION OF AN IMMUNE RESPONSE THERETO

This application claims the priority under 35 U.S.C. 119(e) of U.S. Provisional Application No. 60/331,801, filed Nov. 21, 2001, which is hereby incorporated by reference in its entirety.

GOVERNMENT LICENSE RIGHTS

The experiments performed in this application were supported in part by the National Institutes of Health, Grant Nos. AG08721, AR02594, AG17617, AG20245, AG02594, AG05891, and AG20197. The U.S. Government has a paid-up license in this invention and the right in limited circumstances to require the patent owner to license others on reasonable terms as provided for by the terms of each respective grant listed above.

BACKGROUND OF THE INVENTION

1. Field of the Invention

The present invention relates to the field of amyloid β peptides, prion protein, amylin, α-synuclein, and polyglutamine repeats and methods for inducing an immune response to amyloid β peptides and amyloid deposits, prion proteins and deposits, amylin and amylin fibrils, filaments and fibrils containing α-synuclein, or protein aggregates containing polyglutamine repeats. The invention also relates to a method of treating or preventing amyloid plaque forming diseases or amyloidosis by the use of a synthetic immunogenic but not deposit forming polypeptide homologous to the protein which forms the amyloid plaque.

2. Description of the Background Art

Amyloid β

Alzheimer's disease (AD) is the most common form of late-life dementia in adults (Soto et al., 1994), constituting the fourth leading cause of death in the United States. Approximately 10% of the population over 65 years old is affected by this progressive degenerative disorder that is characterized by memory loss, confusion and a variety of cognitive disabilities. Neuropathologically, AD is characterized by four major lesions: a) intraneuronal, cytoplasmic deposits of neurofibrillary tangles (NFT), b) parenchymal amyloid deposits called neuritic plaques, c) cerebrovascular amyloidosis, and d) synaptic and neuronal loss. One of the key events in AD is the deposition of amyloid as insoluble fibrous masses (amyloidogenesis) resulting in extracellular neuritic plaques and deposits around the walls of cerebral blood vessels. The major constituent of the neuritic plaques and congophilic angiopathy is amyloid β (Aβ), although these deposits also contain other proteins such as glycosaminoglycans and apolipoproteins.

Aβ is a 4.1-4.3 kDa hydrophobic peptide that is codified in chromosome 21 as part of a much longer amyloid precursor protein APP (Muller-Hill et al., 1989). The APP starts with a leader sequence (signal peptide), followed by a cysteine-rich region, an acidic-rich domain, a protease inhibitor motif, a putative N-glycosylated region, a transmembrane domain, and finally a small cytoplasmic region. The Aβ sequence begins close to the membrane on the extracellular side and ends within the membrane. Two-thirds of Aβ faces the extracellular space, and the other third is embedded in the membrane (Kang et al., 1987 and Dyrks et al., 1988). Several lines of evidence suggest that amyloid may play a central role in the early pathogenesis of AD.

Evidence that amyloid may play an important role in the early pathogenesis of AD comes primarily from studies of individuals affected by the familial form of AD (FAD) or by Down's syndrome. Down's syndrome patients have three copies of the APP gene and develop AD neuropathology at an early age (Wisniewski et al., 1985). Genetic analysis of families with hereditary AD revealed mutations in chromosome 21, near or within the Aβ sequence (Forsell et al., 1995), in addition to mutations within the presenilin 1 and 2 genes. Moreover, it was reported that transgenic mice expressing high levels of human mutant APP progressively develop amyloidosis in brain (Games et al., 1995). These findings appear to implicate amyloidogenesis in the pathophysiology of AD. In addition, Aβ fibrils are toxic in neuronal culture (Yankner et al., 1989) and to some extent when injected into animal brains (Sigurdsson et al., 1996 and 1997).

Furthermore, several other pieces of evidence suggest that the deposition of Aβ is a central triggering event in the pathogenesis of AD, which leads subsequently to NFT formation and neuronal loss. The amyloid deposits in AD share a number of properties with all the other cerebral amyloidoses, such as the prion related amyloidoses, as well as the systemic amyloidoses. These characteristics are: 1) being relatively insoluble; 2) having a high β-sheet secondary structure, which is associated with a tendency to aggregate or polymerize; 3) ultrastructurally, the deposits are mainly fibrillary; 4) presence of certain amyloid-associated proteins such as amyloid P component, proteoglycans and apolipoproteins; 5) deposits show a characteristic apple-green birefringence when viewed under polarized light after Congo red staining.

The same peptide that forms amyloid deposits in AD brain was also found in a soluble form (sAβ) normally circulating in the human body fluids (Seubert et al., 1992 and Shoji et al., 1992). Zlokovic et al. (1994), reported that the blood-brain barrier (BBB) has the capability to control cerebrovascular sequestration and transport of circulating sAβ, and that the transport of the sAβ across the BBB was significantly increased when sAβ was perfused in guinea pigs as a complex with apolipoprotein J (apoJ). The sAβ-apoJ complex was found in normal cerebrospinal fluid (CSF; Ghiso et al., 1994) and in vivo studies indicated that sAβ is transported with apoJ as a component of the high density lipoproteins (HDL) in normal human plasma (Koudinov et al., 1994). It was also reported by Zlokovic et al. (1996), that the transport of sAβ across the BBB was almost abolished when the apoJ receptor gp330 was blocked. It is believed that the conversion of sAβ to insoluble fibrils is initiated by a conformational modification of the 2-3 amino acid longer soluble form. It has been suggested that the amyloid formation is a nucleation-dependent phenomena in which the initial insoluble "seed" allows the selective deposition of amyloid (Jarrett et al., 1993).

Peptides containing the sequence 1-40 or 1-42 of Aβ and shorter derivatives can form amyloid-like fibrils in the absence of other protein (Soto et al., 1994), suggesting that the potential to form amyloid resides mainly in the structure of Aβ. The relation between the primary structure of Aβ and its ability to form amyloid-like fibrils was analyzed by altering the sequence of the peptide. Substitution of hydrophilic residues for hydrophobic ones in the internal Aβ hydrophobic regions (amino acids 17-21) impaired fibril formation (Hilbich et al., 1992), suggesting that Aβ assembly is partially driven by hydrophobic interactions. Indeed, larger Aβ peptides (Aβ1-42/43) comprising two or three additional hydrophobic C-terminal residues are more amyloidogenic (Jarrett et al., 1993). Secondly, the conformation adopted by Aβ peptides is crucial in amyloid formation. Aβ peptides incubated at different pH, concentrations and solvents can have either a mainly α-helical, random coil, or a β-sheet secondary structure (Barrow et al., 1992; Burdick et al., 1992 and Zagorski et al., 1992). The Aβ peptide with α-helical or random coil structure aggregates slowly; Aβ with β-sheet conformation aggregates rapidly (Zagorski et al., 1992; Soto et al., 1995 and Soto et al., 1996). The importance of hydrophobicity and β-sheet secondary structure on amyloid formation also is suggested by comparison of the sequence of other amyloidogenic proteins.

Analysis of Aβ aggregation by turbidity measurements indicates that the length of the C-terminal domain of Aβ influences the rate of Aβ assembly by accelerating nucleus formation (Jarrett et al., 1993). Thus, the C-terminal domain of Aβ may regulate fibrillogenesis. However, in vitro modulators of Aβ amyloid formation, such as metal cations (Zn, Al) (Bush et al., 1994 and Exley et al., 1993) heparin sulfate proteoglycans, and apolipoprotein E (Strittmatter et al., 1993) interact with the 12-28 region of Aβ. Moreover, mutations in the APP gene within the N-terminal Aβ domain yield analogs more fibrillogenic (Soto et al., 1995 and Wisniewski et al., 1991). Finally, while the C-terminal domain of Aβ invariably adopts a β-strand structure in aqueous solutions, environmental parameters determine the existence of alternative conformation in the Aβ N-terminal domain (Barrow et al., 1992; Soto et al., 1995 and Burdick et al., 1992). Therefore, the N-terminus may be a potential target site for inhibition of the initial random coil to β-sheet conformational change.

The emerging picture from studies with synthetic peptides is that Aβ amyloid formation is dependent on hydrophobic interactions of Aβ peptides adopting an antiparallel β-sheet conformation and that both the N- and C-terminal domains are important for amyloid formation. The basic unit of fibril formation appears to be the conformer adopting an antiparallel β-sheet composed of strands involving the regions 10-24 and 29-40/42 of the peptide (Soto et al., 1994). Amyloid formation proceeds by intermolecular interactions between the β-strands of several monomers to form an oligomeric β-sheet structure precursor of the fibrillar β-cross conformation. Wood et al., (1995) reported the insertion of aggregation-blocking prolines into amyloid proteins and peptides to prevent aggregation of such proteins and peptides. In this manner, the authors suggest that novel proteins can be designed to avoid the problem of aggregation as a barrier to their production without affecting the structure or function of the native protein. Thus, Wood et al. seek to produce novel proteins that would not aggregate during recombinant protein production and purification by inserting aggregation/blocking prolines into these novel peptides.

To date there is no cure or effective therapy for reducing a patient's amyloid burden or preventing amyloid deposition in AD, and even the unequivocal diagnosis of AD can only be made after postmortem examination of brain tissues for the hallmark neurofibrillary tangles (NFT) and neuritic plaques. However, there are an increasing number of publications outlining strategies for the treatment of Alzheimer's disease. Amyloid-related therapeutic strategies include the use of compounds that affect processing of the amyloid-β precursor protein (APP; Dovey et al., 2001), that interfere with fibril formation or that promote fibril disassembly (Soto et al., 1998; Sigurdsson et al., 2000; and Findeis, 2000).

Heparin sulfate (glycosoaminoglycan) or the heparin sulfate proteoglycan, perlecan, has been identified as a component of all amyloids and has also been implicated in the earliest stages of inflammation-associated amyloid induction. Kisilevsky et al. (1995) describes the use of low molecular weight (135-1,000 Da) anionic sulfonate or sulfate compounds that interfere with the interaction of heparin sulfate with the inflammation-associated amyloid precursor and the β-peptide of AD. Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin-accelerated Alzheimer's Aβ fibril formation and were able to disassemble preformed fibrils in vitro as monitored by electron micrography. Moreover, when administered orally at relatively high concentrations (20 or 50 mM), these compounds substantially arrested murine splenic inflammation-associated amyloid progression in vivo in acute and chronic models. However, the most potent compound, poly-(vinylsulfonate), was acutely toxic.

Anthracycline 4'-iodo-4'-deoxy-doxorubicin (IDOX) has been observed clinically to induce amyloid resorption in patients with immunoglobin light chain amyloidosis (AL). Merlini et al. (1995), elucidated its mechanism of action. IDOX was found to bind strongly via hydrophobic interactions to two distinct binding sites (Scatchard analysis) in five different tested amyloid fibrils, inhibiting fibrillogenesis and the subsequent formation of amyloid deposits in vitro. Preincubation of IDOX with amyloid enhancing factor (AEF) also reduced the formation of amyloid deposits. Specific targeting of IDOX to amyloid deposits in vivo was confirmed in an acute murine model. This binding is distinct from heparin sulfate binding as removal of the glycosaminoglycans from extracted amyloid fibrils with heparinases did not modify IDOX binding. The common structural feature of all amyloids is a β-pleated sheet conformation. However, IDOX does not bind native amyloid precursor light chains which suggests that the β-pleated sheet backbone alone is not sufficient to form the optimal structure for IDOX binding, and that it is the fibril cross-β-sheet quaternary structure that is required for maximal IDOX binding. Tt has been found that the amount of IDOX extracted from spleens is correlated with amyloid load and not circulating serum precursor amyloid levels. IDOX, however, is also extremely toxic.

The regulation and processing of amyloid precursor protein (APP) via inhibition or modulation of phosphorylation of APP control proteins has also been investigated in U.S. Pat. No. 5,385,915 and WO 9427603. Modulating proteolytic processing of APP to nucleating forms of AD has also been examined in AU 9338358 and EP569777. WO 95/046477 discloses synthetic peptides of composition X-X-N-X coupled to a carrier, where X is a cationic amino acid and N is a neutral amino acid, which inhibit Aβ binding to glycosoaminoglycan. Peptides containing Alzheimer's Aβ sequences that inhibit the coupling of α-1-antichymotrypsin and Aβ are disclosed in WO 92/03474.

From experiments conducted at the laboratory of the present inventors, WO 96/39834 discloses that peptides capable of interacting with a hydrophobic portion on a protein or peptide, such as Aβ, involved in amyloid-like deposit formation can be used to inhibit and structurally block the abnormal folding of such proteins and peptides into amyloid or amyloid-like deposits. The peptides which block abnormal folding of Aβ into amyloid deposits have a hydrophobic portion containing β-sheet breaking amino acid residue(s), such as proline, that reduces the propensity of the peptide for adopting a β-sheet conformation. The laboratory of the present inventors, in later reports, have demonstrated that LeuProPhePheAsp (SEQ ID NO:14), a non-amyloidogenic peptide with sequence homology to Aβ blocks fibril formation (Soto et al., 1998), and induces in vivo disassembly of fibrillar Aβ deposits (Sigurdsson et al., 2000).

Recently, the coupling of lysine residues to peptides was proposed by Pallitto et al. (1999), in the design of anti-β sheet peptides or Aβ fibrillogenesis inhibitors that have an Aβ-binding recognition sequence and a hexameric lysine aggregation disrupting element.

In vitro studies have shown that monoclonal antibodies raised against the N-terminal region of Aβ can disaggregate Aβ fibrils, maintain Aβ solubility, and prevent Aβ toxicity in cell culture (Solomon et al., 1996 and 1997).

WO 96/25435 discloses the potential for using a monoclonal antibody, which is end-specific for the free C-terminus of the Aβ1-42 peptide, but not for the Aβ1-43 peptide, in preventing the aggregation of Aβ1-42. The administration of such an Aβ end-specific monoclonal antibody is further disclosed to interact with the free C-terminal residue of Aβ1-42, thereby interfering with and disrupting aggregation that may be pathogenic in AD.

WO 98/44955 takes a different approach to avoiding the problems associated with repeated administration of pharmacological agent and discloses a method for preventing the onset of Alzheimer's Disease or for inhibiting progression of Alzheimer's Disease through the stable ectopic expression in the brain of recombinant antibodies end-specific for amyloid-β peptides.

Recently, Schenk et al. (1999) demonstrated that immunization with amyloid-β attenuated Alzheimer's disease-like pathology in PDAPP transgenic mice serving as an animal model for amyloid-β deposition and Alzheimer's disease-like neuropathologies. They reported that immunization of young animals prior to the onset of Alzheimer's disease-type neuropathologies essentially prevented the development of β-amyloid plaque formation, neuritic dystrophy and astro-gliosis, whereas treatment in older animals after the onset of Alzheimer's disease-type neuropathologies was observed to reduce the extent and progression of these neuropathologies. This effect is thought to be mediated by antibodies, since peripherally administered antibodies against Aβ have been shown to reduce brain parenchymal amyloid burden (Bard et al., 2000). In addition, intranasal immunization with freshly solubilized Aβ1-40 reduces cerebral amyloid burden (Weiner et al., 2000). Two recent studies demonstrated that a vaccination-induced reduction in brain amyloid deposits resulted in cognitive improvements (Morgan et al., 2000; Janus et al., 2000).

Although the results reported by Schenk et al. provides promise for using immunomodulation as a general approach to treat Alzheimer's disease, immunization with intact amyloid-β according to Schenk et al. presents problems that make it inappropriate for human use. First, Schenk et al's experiments used transgenic mice which express a mutated human protein that is foreign to them and that has no physiological function in mice (the mouse and human Aβ peptide sequences are significantly different). However, in humans, the precursor protein (βAPP) is an endogenous protein that has a normal function. Hence, using this approach in humans with a human Aβ peptide may well lead to development of an autoimmune disorder or disease that could make matters worse not better. Second, Martel et al. (1996) and the present inventors have results which demonstrate that Aβ peptides, Aβ1-42 and Aβ1-40, can cross the blood brain barrier in experimental animals. Therefore, in humans, it is expected that Aβ1-42, which is used for immunization in Schenk et al., can cross the blood brain barrier and co-deposit on any existing amyloid plaques leading to increased toxicity, and may actually promote plaque formation. This has not been a problem in the PDAPP transgenic mouse model for AD because human Aβ1-42 is less toxic for the mouse; even with massive deposition of human Aβ1-42, none of the transgenic mice show significant neuronal loss. Thirdly, Schenk et al. use a toxic adjuvant to induce an immune response.

Prion

From a mechanistic point of view, the best understood of the conformational disorders are the prion related diseases (or prionoses). The etiology of these diseases is the conversion of the normal prion protein, $PrP^C$, into its infectious and pathogenic form, $PrP^{Sc}$ (Prusiner et al., 1998; Horwich and Weismann, 1997). $PrP^C$ and $PrP^{Sc}$ are thought to differ only in their conformation, with $PrP^{Sc}$ having a greater β-sheet content.

The first of these disorders to be described was scrapie, a disease of sheep recognized for over 250 years. This illness manifested by hyper-excitability, itching and ataxia, leads to paralysis and death. It is called scrapie because of the tendency of affected animals to rub against the fences of their pens in order to stay upright, reflecting their cerebellar dysfunction. The transmission of this disease was demonstrated first in 1943 when a population of Scottish sheep was accidentally inoculated against a common virus using a formalin extract of lymphoid tissue from an animal with scrapie (Gordon, 1946). After an incubation period of two years about 10% of the inoculated animals developed scrapie.

The first human prionosis was described some years later and is called kuru (Gajdusek and Zigas, 1957; Gajdusek and Zigas, 1959). This is an illness of the Fore people living in the highlands of New Guinea, that is thought to be linked to ritualistic cannibalism. Presumably this illness originated with the accidental consumption of an initial patient with sporadic Creutzfeldt-Jacob disease (CJD). Kuru was once the major cause of death among Fore women; however, the disease has virtually disappeared with the end of cannibalistic rituals. Rather similar to scrapie, patients clinically present with difficulty walking and develop progressive signs of cerebellar dysfunction. Death occurs approximately 1 year following onset of symptoms. The neuropathology of kuru, in common with all prionoses to a variable extent, includes widespread spongiform change and astrocytosis, as well as neuronal loss affecting the cerebral hemispheres and cerebellum. In about 70% of cases, amyloid plaques are found, with amyloid deposition being a common but not invariable accompaniment of the prionoses. It was Gajdusek's detailed description of this illness that lead Hadlow to suggest that kuru might be the human representation of scrapie (Hadlow, 1959). This in turn suggested to Gajdusek and his team to test whether kuru was also transmissible. They first showed kuru was transmissible to chimpanzees, after a long incubation, in 1966 (Gajdusek et al., 1966); this work led to Gajdusek being awarded the Nobel Prize in 1976.

Other human prionoses include Gerstamann-Sträussler-Scheinker disease (GSS), described in a large kindred in 1936 (Gerstmann et al., 1936). This illness presents with a slowly progressive limb and truncal ataxia, as well as dementia, with death occurring from 6 to 10 years following presentation. The pattern of inheritance is autosomal dominant; it is now known that all cases of GSS are associated with mutations of the PrP gene. The neuropathology of GSS is remarkable in that there is extensive and invariable amyloid deposition, in addition to the typical spongiform change, gliosis and neuronal loss. Interestingly, in several kindreds of GSS, extensive neurofibrillary tangle (NFT) formation is found (Ghetti et al., 1994). NFTs are an essential feature of AD. Another variation of autosomal dominantly inherited human prionosis has been termed prion protein-congophilic angiopathy (PrP-CAA), which is characterized by cerebral vessel PrP amyloid deposition and the presence of NFT (Ghetti et al., 1996). CAA is also an essential feature of AD. Both these variants of prionoses further link the pathogenesis of AD and the prion related diseases.

Creutzfeldt-Jacob disease (CJD) was initially described by Jacob in 1921 (Jacob, 1921); ironically, the case reported by Creutzfeldt a year earlier is probably unrelated to the disease which carries his name. Clinically CJD is characterized by a rapidly progressive dementia, associated with myoclonic jerks, as well as a variable constellation of pyramidal, extrapyramidal and cerebellar signs. The EEG typically shows distinctive changes of high voltage, slow (1 to 2 Hz) and sharp wave complexes on an increasingly slow and low-voltage background. CJD is found throughout the world with an incidence of about 1 per million. In addition to extensive cortical spongiosis, gliosis and neuronal loss, 10% of CJD cases have amyloid plaques (Prusiner et al., 1998).

Fatal familial insomnia (FFI) is a disorder presenting with intractable insomnia, dysautonomia, a variety of endocrine abnormalities and motor paralysis (Medori et al., 1992). Neuropathologically, there is marked atrophy of the anterior ventral and mediodorsal thalamic nuclei, due to neuronal loss and gliosis. Unlike other prionoses, spongiform change can be a minor feature or be absent altogether. All patients with FFI have a missense mutation at codon 178 of the PrP gene where Asn is replaced by Asp, coupled with a Met at the polymorphic codon 129 (Goldfarb et al., 1992). The somewhat divergent clinical and neuropathological features of FFI, in comparison to other human prionoses, highlight the wide spectrum of disease associated with PrP dysfunction and suggests that there may be other human illnesses which have yet to be recognized as prionoses.

There has been a recent epidemic of a new prionosis, bovine spongiform encephalopathy (BSE), that has led to more than 160,000 cattle deaths in the UK (Collinge, 1997). This new disease is thought to be caused by meat and bone meal dietary supplements to cattle that were contaminated with scrapie infected sheep and other cattle with BSE. Some evidence suggests that BSE also has led to a new type of CJD, called new variant CJD (vCJD) (Collinge et al., 1996a). The first cases of vCJD were reported in 1995, when two cases of CJD were found in 2 British teenagers (Bateman et al., 1995; Britton et al., 1995). Only 4 cases of sporadic CJD have been reported previously among teenagers; the peak onset of sporadic CJD being between ages 60 to 65 years. In addition to the early age, these cases had distinctive neuropathology that included so-called "florid" amyloid plaques which are reminiscent of kuru associated PrP amyloid plaques (Collee and Bradley, 1997; Will et al., 1997). Since the original reports, there have been 14 cases with these distinctive features; all were in the UK except for one French case. The emergence of vCJD has raised the specter of an epidemic of prion related disease among the British population similar to that of BSE in cattle.

Highly divergent hypotheses have been put forward regarding the etiology of the prionoses, including that they consist of nucleic acid only, protein only, are lacking both protein and nucleic acid or are a polysaccharide. The most widely accepted hypothesis, first put forward by Griffith (Griffith, 1967) and more explicitly by Pruisner is the "protein only" hypothesis (Prusiner et al., 1998). Pruisner introduced the term "prion" to indicate that scrapie is related to a proteinous infectious particle (Prusiner, 1982). This hypothesis was initially greeted with great scepticism in the scientific community; now it represents the current dogma with Dr. Pruisner being honored with the 1998 Noble Prize for Science. This hypothesis suggests that prions contain no nucleic acid and are referred to as $PrP^{Sc}$. The latter represents a conformationally modified form of a normal cellular $PrP^C$, which is a normal host protein found on the surface of many cells, in particular neurons. $PrP^{Sc}$ when introduced into normal, healthy cells causes the conversion of $PrP^C$ into $PrP^{Sc}$, initiating a self-perpetuating vicious cycle (Prusiner et al., 1998).

Other hypotheses for prion have included the "virino hypothesis" (Weissmann, 1996). Here it is suggested that the infectious agent consists of a nucleic acid with host derived $PrP^{Sc}$ serving as a coat. The latter would explain the lack of an immunological and inflammatory response, while the presence of a nucleic acid provides an explanation for the numerous strains of scrapie, each with distinctive features. Other investigators have also suggested that the scrapie agent is a conventional virus with highly atypical properties. However, despite extensive searches, no nucleic acid associated with prion infection has been detected so far. The unusual nature of the scrapie agent first became apparent during the early transmission studies, where it first was found that infectivity was filterable, consistent with the presence of a virus, but differing from viruses in that formalin treatment did not abolish this infectivity (Gordon, 1946). Later Alper et al. showed that the scrapie agent was resistant to inactivation by UV at 254 nm unlike nucleic acid (Alper et al., 1967), but sensitive to irradiation at 237 nm, suggestive of the presence of a protein (Latarjet et al., 1970). The possibility that a protein was involved was furthered by the pioneering work of Pruisner et al. with the biochemical partial purification of infectious activity (Prusiner, 1982). These workers reported a 1000 fold increase in infectivity compared to homogenates of infectious brain by a series of steps involving polyethylene glycol precipitation, nuclease digestion, partial proteinase K (PK) digestion and density gradient centrifugation. The enriched infectious activity was inactivitated or reduced by extensive PK digestion, diethyl pyrocarbonate, urea, chaotropes, phenol and/or SDS. However, it was unaffected by nuclease digestion or UV irradiation. Pruisner et al. identified a protein within this enriched infectious material which they termed PrP that was resistant to partial PK digestion and was found only in infected hamster brains. This protein migrated on SDS-PAGE at 27-30 kDa and ultrastructurally had the appearance of rods, which were first identified by Merz et al. (Merz et al., 1981). Fractions enriched for these rods were found to be highly infectious. This $PrP^{Sc}$ is thought to differ from the normal cellular $PrP^C$ by conformation alone. FT-IR and CD studies have identified that $PrP^C$ is about 40% α-helical with little β-sheet, while $PrP^{Sc}$ is ~30% α-helical and ~45% β-sheet (Pan et al., 1993; Caughey et al., 1997; Safar et al., 1993). So far, no post-translational modifications have been found that distinguish $PrP^{Sc}$ from $PrP^C$ despite numerous studies. However, a remaining major problem is that even with current techniques, the ratio of $PrP^{Sc}$ molecules to infectious units is on the order of 10,000 to one (Horwich and Weismann, 1997). Hence, with such a ratio it is very difficult to completely rule out that other essential components are not part of the infectious agent or that some covalent or other post-translational modifications do not occur as part of the $PrP^C$ to $PrP^{Sc}$ conversion. Indeed, the pattern of glycosylation has been shown to be distinctive among differing human $PrP^{Sc}$ types, indicating that this post-translational modification may influence strain specificity (Collinge et al., 1996b). For the final proof of the "protein only" hypothesis it will be necessary to produce infectious particles in vitro from purified $PrP^C$ or from recombinant protein.

With the purification of PrP27-30 it was possible to obtain its amino terminal sequence and subsequently cDNA clones encoding the PrP protein (Liao et al., 1986; Oesch et al., 1985). The human PrP gene is found on chromosome 20. It spans 20 kb and consists of a short, non-coding first exon, a 10-15 kb intron and a second exon that contains the entire 759 bp open reading frame and 1.64 kb of 3' non-translated sequence, with the translation product being 253 amino acids long. The PrP gene is highly conserved across mammalian species and is constitutively expressed in both neuronal and non-neuronal tissue (Kretzschmar et al., 1986). The highest mRNA levels are found in neurons, in particular in the hippocampus; however, substantial amounts are also found in the heart and skeletal muscle. The primary structure of PrP from normal animals was found to be identical to that found from scrapie infected animals and the levels of mRNA were comparable in both settings (Oesch et al., 1985; Chesebro et al., 1985). Cell culture studies have indicated that $PrP^C$ is transported in secretory vesicles to the external cell surface, where it is anchored via a GPI moiety (Taraboulos et al., 1992). Most of this $PrP^C$ is internalized into an endocytic compartment; however, some can be released into the extracellular space by cleavage of the GPI anchor(Shyng et al., 1993). The endocytic $PrP^C$ is recycled intact to the cell surface or cleaved at the N-terminus and externalized (Harris et al., 1993; Shyng et al., 1993). The identification of the PrP gene, designated PRNP in humans, also allowed for the characterization of numerous mutations associated with familial prionoses (Prusiner et al., 1998). Three mutations in the first putative α-helical domains of PrP at codons 102, 105 and 117, with a fourth at codon 145, which is at the carboxyl end of the second putative helical domain, are associated with a GSS phenotype. The codon 145 mutation produces a stop codon and the synthesis of a truncated PrP (Kitamoto et al., 1993). Other GSS linked mutations occur at codons 198 and 217 (Dlouhy et al., 1992; Hsiao et al., 1992). Interestingly, these two mutations are associated with widespread NFT similar to that seen in AD. Conversely, a familial CJD picture, with little or no amyloid deposition, has been identified among kindreds with insertions of variable octarepeats in the amino terminal domain of PrP and mutations at codons 178, 180, 200, 210 and 232; all these are in the third and fourth putative helical domains of PrP (Prusiner et al., 1998). A particularly interesting mutation occurs at codon 178, resulting in a substitution of Asn for Asp. This point mutation can result in either the clinical picture of CJD or FFI depending on a polymorphism at codon 129 (Medori et al., 1992; Goldfarb et al., 1992). The codon 178 mutation, plus Met at codon 129 results in FFI whereas if there is a Val at codon 129 a CJD picture is seen. This demonstrates the importance of the 129 codon polymorphism on the distribution of disease, since in FFI the neuropathology is largely confined to the thalamus while in CJD there is widespread spongiform change in the cerebral cortex and in subcortical nuclei.

Two critical genetic studies provide strong evidence for the requirement of endogenous $PrP^C$ for $PrP^{Sc}$ infection. The first of these used PrP knockout mice designated $Prnp^{0/0}$. In two such lines of $Prnp^{0/0}$ mice, there were little or no differences found from controls (Bueler et al., 1992; Manson et al., 1994); however, altered sleep-wake cycles and abnormal synaptic behavior in brain slices have been reported (Tobler et al., 1996; Collinge et al., 1994). The synaptic changes could not be confirmed by one other group (Liedo et al., 1996). One line of $Prnp^{0/0}$ mice showed ataxia and Purkinje cell loss at about 70 weeks of age (Sakaguchi et al., 1996). Importantly, during transmission studies all of these different lines of $Prnp^{0/0}$ mice have all been shown to be highly resistant to prion infection (Bueler et al., 1993; Prusiner et al., 1993). $Prnp^{0/0}$ mice sacrificed at 4, 60, 120 and 315 days after inoculation with prions showed no infectivity with the exception of residual infectivity from the inoculum detected at five day following inoculation.

The second set of genetic mouse experiments showing the need for endogenous PrP used mice expressing PrP with a GSS linked mutation. These mice spontaneously express prion disease which could be transferred when inoculated into transgenic mice expressing low levels of the same mutant PrP protein, but which otherwise would not develop disease (Telling et al., 1996; Hsiao et al., 1994). These transgenic mouse experiments combined with the $Prnp^{0/0}$ mice, clearly show the need for endogenous $PrP^C$ for expression of disease.

A ligand which interacts with $PrP^C$ in the production of $PrP^{Sc}$ has also been suggested and has been called "protein X" (Prusiner et al., 1998). The existence of protein X is indicated by a number of transmission studies by Pruisner's team. They found the transmission of human CJD prions to transgenic mice expressing human $PrP^C$, Tg(HuPrP), occurred in only about 10% of inoculated mice, which is similar to the rate seen in wild-type mice (Telling et al., 1994). This situation was very different when transgenic mice were used that express a chimeric human/mouse (Hu/Mo) transgene (MH2M). The $PrP^C$ encoded by MH2M differed from Mo $PrP^C$ by nine amino acids within residues 96 to 167, while there are 28 amino acid differences between the entire mouse and human PrP sequences. All these mice, when inoculated with human $PrP^{Sc}$ become sick with fairly short incubation periods of 202 to 249 days (Telling et al., 1995). The much higher frequency of human CJD $PrP^{Sc}$ transmission to Tg(MHu2M) mice versus the Tg(HuPrP) shows the importance of the mouse PrP sequence and may suggest that participation of a cellular factor that recognizes some epitopes that are specific for mouse PrP versus the human PrP. It is this cellular factor that has been designated protein X.

Given our increasing knowledge of the factors involved in the $PrP^C$ to $PrP^{Sc}$ conversion, its conceivable to design effective therapeutic agents. Currently, no such therapeutic agents exist. So far only a limited number of approaches have been attempted. Experimental treatment approaches that have been reported for prion diseases include the use of amphotericin B (Pocchiari et al., 1987), Congo red (Caughey and Race, 1992), sulphated polyanions (Ladogana et al., 1992), anthracyclines (Tagliavini et al., 1997), β-sheet breaker peptides (Soto et al., 2000), porphyrin and phthalocyanine compounds (Priola et al., 2000). Some of these compounds delay the incubation time of animals infected with $PrP^{Sc}$ but all have limitations in terms of toxicity and/or pharmacokinetics. Other approaches would be the development of agents that either modify the action of protein X or inhibit the conformational change of $PrP^C$ to $PrP^{Sc}$.

Amylin

Type-2 diabetes mellitus is characterized by defects in the action of insulin and/or its secretion (Hoppener et al., 2000). Usually both abnormalities are present but to a varying degree, depending on the patient and the course of the disease. Islet amyloid is found in about 90% of patients with type 2 diabetes, and there is a good correlation between the extent of amyloid deposition and a reduction in insulin-producing β-cells, suggesting that these deposits may lead to β-cell failure (Howard, Jr., 1986). Identical deposits are found in other species that develop this disease (Westermark et al., 1990), but are absent in rodents (Westermark et al., 1990; Johnson et al., 1989; Moriarty and Raleigh, 1999).

The islet amyloid fibrils are composed of a 37 amino acid peptide known as islet amyloid polypeptide or amylin (Johnson et al., 1989). The nucleotide sequence of the amylin gene is identical in normal subjects compared to diabetes patients indicating that a change in amino acid sequence is not the cause of amyloid fibril formation. An amyloidogenic region (amino acids 20-29) has been identified in the human amylin peptide by in viLro studies and by comparing the amino acid sequences of various species in some of which amylin is not deposited, such as rats, mice and hamsters (Westermark et al., 1990; Johnson et al., 1989; Moriarty and Raleigh, 1999).

Amylin fibrils are formed intracellularly and are also found extracellularly. The mechanism of toxicity of these fibrils has not been thoroughly investigated although integration of aggregates into cell membranes, which can then function as calcium permeable ion channels, has been implicated (Mirzabekov et al., 1996). Subsequent increase in intracellular calcium may lead to cytotoxcity. Disruption of intracellular membranes by amyloid fibrils may also have a role in their toxicity (Janson et al., 1999).

Potential therapeutic targets for Type-2 diabetes involve:

A) Reducing the production of amylin or inhibiting fibrillogenesis with: 1) drugs blocking amylin generating enzymes; 2) drugs affecting the interaction between amylin and its chaperones (Kisilevsky, 1996); 3) the use of antibodies against amylin; and 4) compounds that bind to amylin and prevent fibril formation and/or lead to fibril disassembly, an approach used for other amyloid diseases (Soto et al., 1998; Sigurdsson et al., 2000; Soto et al., 2000).

B) Reducing the demand for endogenous insulin by providing insulin therapy early in the course (Lindstrom et al., 1997).

C) Lowering glucose production (Zapecka-Dubno et al., 1999).

D) Increasing peripheral glucose disposal (Inzucchi et al., 1998).

α-Synuclein

Parkinson's disease (PD) is the second most common neurodegenerative disease and the most common movement disorder (Goedert, 2001). It affects 1-2% of the population over 65 years. PD is primarily characterized by muscle rigidity, bradykinesia and resting tremor. Lewy bodies, found to the greatest extent in the substantia nigra, are the defining neuropathological characteristics of all cases of PD and are mainly composed of α-synuclein (Spillantini et al., 1997). The substantia nigra is rich in dopaminergic neuronal cell bodies and is the main site of cell loss in PD. Subsequent effects on the dopaminergic system are primarily responsible for the clinical symptoms. Cell loss is also seen in the motor nucleus of the vagus nerve, the hypothalamus, the nucleus basalis of Meynert, the locus coeruleus, the cerebral cortex, the olfactory bulb and the autonomic nervous system. Most of PD cases are idiopathic although a missense mutation in the α-synuclein gene is a rare genetic cause of PD (Polymeropoulos et al., 1997). Filamentous inclusions of this protein are also found in multiple system atrophy (MSA), such as olivopontocerebellar atropy, striatonigral degeneration, and Shy-Drager syndrome (Goedert, 2001). In MSA, glial cytoplasmic inclusions are observed instead of Lewy bodies. Another disease characterized by Lewy bodies and Lewy neurites is dementia with Lewy bodies (DLB), a common form of late onset dementia that often overlaps with Alzheimer's disease. Unlike PD, DLB has numerous Lewy bodies and Lewy neurites in the cerebral cortex (Kosaka, 1978), although the substantia nigra is also affected as in PD. Lewy bodies are also found in numerous rare diseases (Goedert, 2001).

Synuclein proteins are abundant in the brain although their physiological function is not understood. The family consists of α-, β- and γ-synuclein ranging from 127 to 140 amino acids, which are 55-62% identical in amino acid sequences (Goedert, 2001). Of these three, only α-synuclein is associated with diseases containing Lewy bodies and MSA with pathology primarily in neurons and glia, respectively. Inactivation of the α-synuclein gene does not lead to a severe neurological phenotype, suggesting that loss of function of the protein does not lead to the neurodegeneration observed in PD (Abeliovich et al., 2000).

The accumulation of intracellular aggregates of α-synuclein has been implicated in the pathogenesis of these diseases although the mechanism of toxicity remains to be determined. Assembly of α-synuclein is accompanied by the conversion of a random coil formation to a β-pleated sheet (Serpell et al., 2000; Conway et al., 2000; Biere et al., 2000), and occurs through the repeats in the amino-terminal region, whereas the carboxy-terminal regions inhibits assembly (Goedert, 2001). At least one of the α-synuclein mutations (A53T) leads to generation of an altered α-synuclein with an increased rate of filament formation. Although α-synuclein aggregates do not stain with typical stains used to detect amyloid they have been shown by electron diffraction to have the conformation characteristics of amyloid fibrils (Serpell et al., 2000). β- and γ-synuclein do not assemble into filaments (Serpell et al., 2000; Biere et al., 2000; Giasson et al., 2001), which may explain why these forms have not been implicated in any diseases.

Although various treatment options are available for PD, most of them affect the dopaminergic system or deal with the side effects of those drugs (Hely et al., 2000). This is a symptomatic treatment but does not address the cause of the disease. Presently, there are no reports on experimental α-synuclein based therapy.

Polyglutamine

There are eight neurodegenerative disorders caused by expansion of a CAG trinucleotide repeat coding for polyglutamine (Kaytor and Warren, 1999). These diseases are Spinocerebellar Ataxia Type 1 (39-83 glutamine repeats), Type 3 (55-84 repeats), Type 6 (21-30 repeats), Type 7 (34 to over 200 repeats), Huntington's disease (HD; 38-180 repeats), Spinal and Bulbar Muscular Atrophy (38-65 repeats), and Dentatorubral-Pallidoluysian Atropy (49-88 repeats). Protein aggregates have been found in most of these diseases (Kaytor and Warren, 1999). Their common features are progressive neuronal loss and decline in motor and cognitive functions (Zoghbi and Orr, 2000). The mechanism of pathogenesis has not been elucidated but the polyglutamine repeats are important because longer repeats lead to earlier onset and more severe phenotype (Kaytor and Warren, 1999; Hughes and Olson, 2001).

Huntington's disease has been the most extensively investigated of these diseases. Nuclear inclusions of huntingtin are found both in neurons and in non-neuronal tissue outside the brain (Gutekunst et al., 1999). The striatum is predominantly affected in HD, although it contains far fewer protein aggregates than the cortex (Gutekunst et al., 1999), suggesting that some cell types are more vulnerable to the toxicity of the inclusions. There is a good correlation between the lengths of a truncated hutingtin protein and the size of the CAG repeat with the frequency and localization of aggregates (Rubinsztein et al., 1999). Huntingtin aggregation can be inhibited in vitro by antibodies and with compounds that bind to the β-sheet conformation of amyloid fibrils such as Congo red, thioflavin S, chrysamine G and Direct fast yellow (Heiser et al., 2000). Although HD is not considered an amyloid disease, these findings suggest that a similar therapy approach as is being developed for amyloid diseases may be effective for these diseases as well because the aggregates have a high β-sheet content. Other drug candidates include excitatory amino acid receptor antagonists, glutamate release inhibitors and mitochondrial agents (Hughes and Olson, 2001). Presently, no effective treatments have been developed for HD or the other polyglutamine diseases (Hughes and Olson, 2001).

In these diseases, the aggregates are found intra- and/or extracellularily. Antibody mediated clearance of extracellular Aβ deposits has already been observed by others and us. With regard to the intracellular deposits, there are several reports of cellular uptake of antibodies. It has been demonstrated that a monoclonal antibody markedly inhibits rabies virus RNA transcription following its cellular internalization (Dietzschold et al., 1992). Also, motor neurons of the CNS in rats that project outside the BBB seem capable of picking up IgG from serum by retrograde transport (Fabian and Petroff, 1987). Furthermore, extraction of IgG from the CSF by dendrites of Purkinje cells has been demonstrated both in the rat (Borges et al., 1985) and the guinea pig (Graus et al., 1991). In human necropsy studies normal IgG has been detected in large amounts in the cytoplasm of Purkinje cells (Fishman et al., 1990), and anti-neuronal antibodies have been found in the human dorsal root ganglia and Purkinje cells (Drlicek et al., 1992). Given these reports, the antibodies may gain access into affected cells where they may facilitate disassembly of the aggregates and/or prevent their formation.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides an immunogenic but non-deposit-forming polypeptide or peptide homologous to amyloid β, to prion protein, to amylin, or α-synuclein, or to polyglutamine repeat-containing proteins, which can be used for induction of an immune response thereto and which would overcome or avoid the complications and problems encountered in the prior art.

A synthetic immunogenic but non-amyloidogenic peptide homologous to amyloid β according to the present invention includes the first thirty amino acid residues of Aβ1-42 (SEQ ID NO:1), where zero to five of residues 17-21 is substituted with Lys, Asp, Glu, Pro, Gly, or Ser and preferably further includes an N-terminal and/or C-terminal segment of 4-10 Lys or Asp residues. Preferred peptides according to this embodiment include, but are not limited to, SEQ ID NOS:2-5, 7-10, and 15-20.

A synthetic immunogenic but non-deposit-forming polypeptide or peptide homologous to human (SEQ ID NO:21) or bovine (SEQ ID NO:30) prion protein according to the present invention includes either (1) the full-length prion protein where one to five of residues 121, 122, 128, 129, and 130 of human prion protein (PrP) or of residues 132, 133, 139, 140, and 141 of bovine prion protein is substituted with Pro, Glu, Asp, Lys, Gly, or Ser; (2) a fragment of the modified full-length prion protein of (1) containing at least residues 90-144 of human prion protein or residues 93-136 of bovine prion protein or; (3) a peptide corresponding to residues 90-144 of human prion protein or to residues 93-156 of bovine prion protein in which zero, or one to five of residues 121, 122, 128, 129, 130 or 132, 133, 139, 140, 141, respectively, is substituted with Pro, Glu, Asp, Lys, Gly or Ser and a polylysine or polyaspartate segment of 4 to 10 residues is preferably present at the N-terminus and/or C-terminus. Preferred peptides according to this embodiment include, but are not limited to, SEQ ID NO:32 and SEQ ID NO:34-39, as well as SEQ ID NO:33 and SEQ ID NO:40-45.

A synthetic immunogenic but non-deposit-forming peptide homologous to human amylin according to the present invention includes the sequence of human amylin (SEQ ID NO:46) where zero, one, two, or three of residues 23, 26 and 27 is substituted with Pro, Glu, Asp, Lys, Gly, or Ser and a polylysine or polyaspartate segment of 4 to 10 residues is preferably present at the N-terminus and/or C-terminus. Preferred peptides according to this embodiment include, but are not limited to, SEQ ID NOS:48-53.

An immunogenic but non-deposit forming peptide homologous to human α-synuclein according to the present invention includes the full-length human α-synuclein (SEQ ID NO:54) where one or more of the sets of valine residues, (1) valine residues 37 and 40, (2) valine residues 48, 49, and 52, and (3) residues 70, 71 and 74, is substituted with all Glu, all Asp, all Pro, or all Lys residues, or includes a N-terminal fragment of 30-36 residues in length or a C-terminal fragment of 30-66 residues in length of human α-synuclein either alone or preferably joined at its N-terminus and/or C-terminus to a polylysine or polyaspartate segment of 4-10 residues in length is also provided by the present invention. Preferred peptides according to this embodiment include, but are not limited to, SEQ ID NO:55.

A synthetic immunogenic, preferably non-deposit-forming, polypeptide or peptide which contains a polyglutamine segment of 30-200 glutamine residues in length joined at its N-terminus and/or C-terminus to a polylysine or polyaspartate segment of 4-10 residues in length.

The present invention also provides a conjugate in which a polypeptide or peptide of the present invention is cross-linked to an immunostimulatory polymer molecule.

Another aspect of the present invention is directed to an immunizing composition/vaccine which contains an immunizing effective amount of the immunogenic polypeptide or peptide of the present invention, or a conjugate thereof.

The invention also provides a method of treating or preventing amyloid plaque forming diseases or amyloidosis by the use of a synthetic immunogenic but not deposit forming polypeptide or peptide homologous to the protein which forms the amyloid plaque. In one embodiment, the protein is homologous to the full length protein or peptide, in another embodiment, it includes only a portion of the protein or peptide which forms the amyloid plaque. In one embodiment, at least one residue is substituted with a different amino acid so as to decrease fibrillogenicity and in another embodiment it further includes a polylysine or polyaspartate segment (of 4-10) residues at the N-terminal and or the C-terminal.

In yet another embodiment, the invention provides a method of reducing amyloidosis comprising the step of administering an immunizing composition comprising a synthetic immunogenic but non-amyloidogenic peptide homologous to amyloid β, thereby reducing amyloidosis. In one embodiment, the synthetic peptide includes the first thirty amino acid residues of Aβ1-42 (SEQ ID NO:1), where zero to five of residues 17-21 are substituted with Lys, Asp, Glu, Pro, Gly, or Ser and preferably further includes an N-terminal and/or C-terminal segment of 4-10 Lys or Asp residues.

A further aspect of the present invention provides for a method for immunotherapy to induce an immune response to any one of amyloid β peptides and amyloid deposits, prion protein and prion deposits, amylin and amylin fibrils, α-synuclein and deposits containing α-synuclein, or proteins with polyglutamine repeats that are associated with neurodegenerative movement disorders.

A still further aspect of the invention provides for molecules which include the antigen-binding portion of an antibody specific for the immunogenic polypeptide or peptide of the present invention, as well as for the preparation and use of these molecules. Such molecules include, but are not limited to, antibodies such as monoclonal antibodies, antibody fragments, single chain antibodies, and humanized antibodies. Also provided are pharmaceutical compositions containing such molecules or antibodies together with one or more pharmaceutically acceptable carriers, diluents, excipients or auxiliary agents, as well as methods for reducing the formation of fibrils or deposits of amyloid, prion, amylin, α-synuclein, or a protein with polyglutamine repeats, by administering such compositions to a subject, preferably a human subject, in need thereof.

The invention also provides for the use of an immunogenic but non-deposit-forming polypeptide or peptide homologous to amyloid β, to prion protein, to amylin, or α-synuclein, or to a polyglutamine repeat-containing protein, for the preparation of a medicament for treating amyloidosis or a disease or disorder characterized by deposits, fibrils, or aggregates of on or more of these polypeptides or peptides. In addition, the invention provides for molecules containing the antigen-binding portion of antibodies against an immunogenic but non-deposit-forming polypeptide or peptide of the invention, for use in the preparation of a medicament for treating a disease or disorder characterized by deposits, fibrils, or aggregates of one or more of these polypeptides or peptides. Such diseases and disorders include, but are not limited to, amyloidosis, Alzheimer's Disease, prionoses, type 2 diabetes or islet amyloidosis, Parkinson's Disease, and Huntington's Disease.

BRIEF DESCRIPTION OF THE DRAWINGS

FIGS. 3A-3D show coronal sections (X50; original magnification) stained with 6E10 against Aβ, through the hippocampus and cortex in a Tg control-(FIG. 3A) and K6Aβ1-30-treated (FIG. 3B) Tg mouse. FIGS. 3C and 3D are adjacent sections (X100) double stained for interleukin-1 that recognizes microglia, and Aβ. Note the reduction of amyloid burden in the immunized mouse (FIG. 3B), and the lack of ramified microglia (FIG. 3D) surrounding Aβ plaque in the same mouse, compared to a control mouse (FIG. 3A, 3C). The bars in FIGS. 3A and 3C are 100 μm. Abbreviations: hip=hippocampus; cx=cortex; cc=corpus callosum.

FIG. 10 shows an alignment of amino acid sequences of prion protein (PrP) from human (SEQ ID NO:21), gorilla (SEQ ID NO:22), chimpanzee (SEQ ID NO:23), mouse (SEQ ID NO:24), rat (SEQ ID NO:25), Syrian hamster (SEQ ID NO:26), mink (SEQ ID NO:27), sheep (SEQ ID NO:28), goat (SEQ ID NO:29), cow (SEQ ID NO:30), and greater kudu (SEQ ID NO:31). Amino acid residues that are identical and conserved among the prion proteins of the species presented in this figure are boxed.

FIG. 13A shows the maze design during the adaptation phase, and FIG. 13B during testing. Dotted lines indicate blocked alleys.

DETAILED DESCRIPTION OF THE INVENTION

Figure 1:
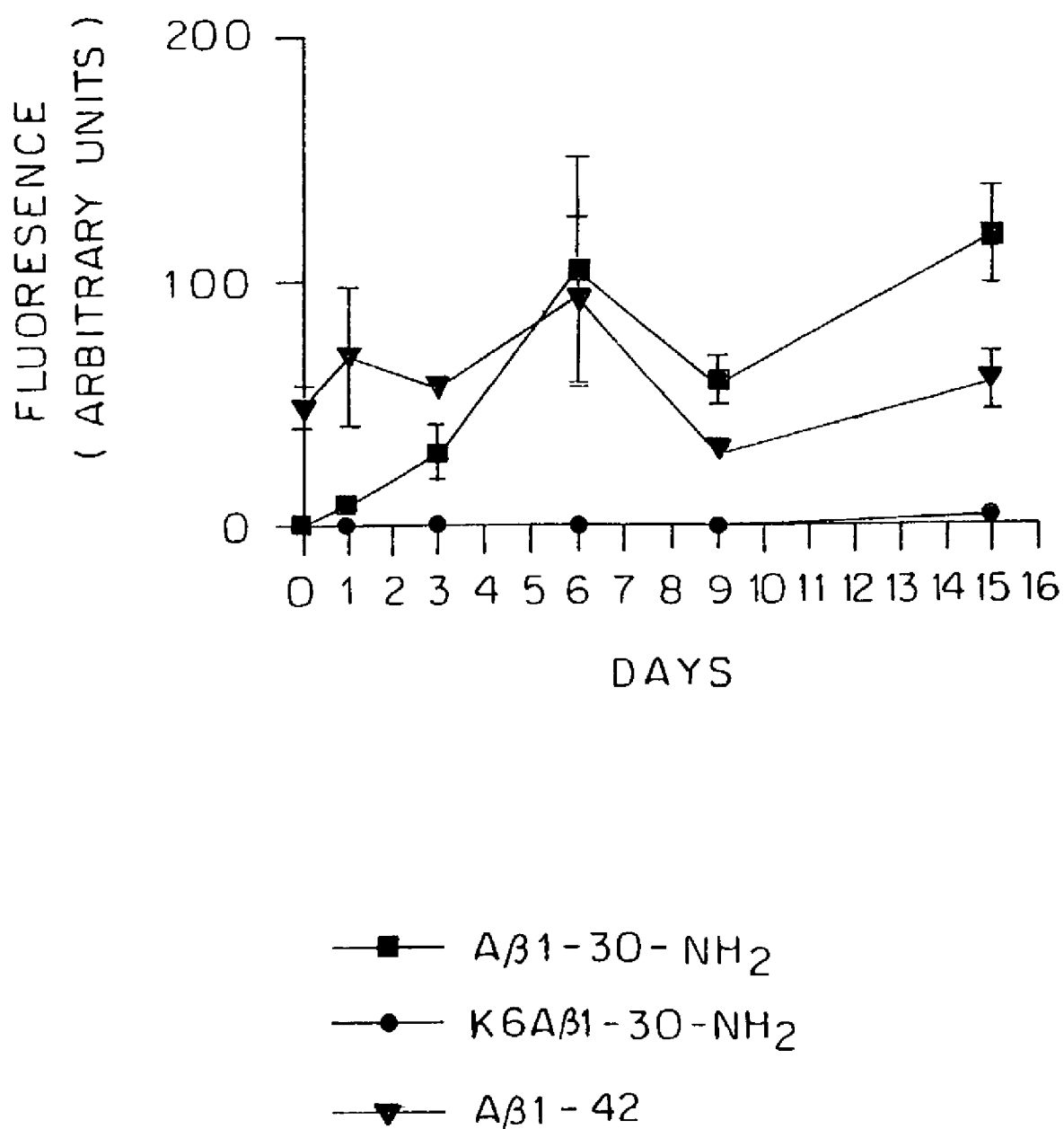
FIG. 1 shows the results of a thioflavin T fluorometric assay. Fibril formation of Aβ1-42, Aβ1-30-NH$_2$, and K6Aβ1-30-NH$_2$ (SEQ ID NO:6) was measured in vitro following incubation at 37° C. K6Aβ1-30-NH$_2$ was the only peptide that did not form fibrils at any of the time points.

The present inventors have designed synthetic non-deposit-forming polypeptides/peptides homologous to amyloid β (Aβ), prion protein (PrP), amylin, α-synuclein, and polyglutamine repeat-containing proteins as an antigenic source. The peptide homologues have a reduced ability to adopt a β-sheet conformation, and have a lower risk of leading to any toxic effects in humans. By using these synthetic non-depositing-forming peptides, antibodies thereto, or conjugates thereof, in an immunizing composition, the present invention provides a means for rendering Aβ peptides and amyloid deposits, prion proteins and deposits, amylin and amylin fibrils, α-synuclein and deposits containing α-synuclein, or polyglutamine repeats and polyglutamine repeat-containing proteins as targets for the immune system. The amino acids in these peptides may be in either L- or D-form. D-form peptides can have a higher stability than L-form peptides in vivo.

An important feature provided by the present invention is a method for immunization which minimizes the toxicity associated with injected polypeptides/peptides, i.e., Aβ or other peptides, while maximizing the immune response to deposits and polypeptides/peptides that make up the deposits, such as amyloid deposits and Aβ peptides, prion deposits and prion protein, etc.

"Amyloidosis" as used herein refers to the deposition of insoluble, fibrous amyloid (or "aggregate") proteins, which are predominantly found extracellularly in organs and tissues. Amyloid fibrils can consist of various amino acid sequences, but, in general, all share β-pleated-sheet (or "β-sheet") secondary structure. Amyloid proteins include, but are not limited to, amyloid-β, amylin, prion protein, α-synuclein, and huntingtin. See, also, Sigurdsson et al. (Trends Mol Med, 2002).

The term "reducing amyloidosis" refers herein after to a decrease in either the amyloid plaques or deposits, number or size, or both, or in another embodiment, a decrease in the symptoms of the disease or another marker of the disease. Such methods are known to those skilled in the art.

Amyloid β Variants

The synthetic non-amyloidogenic but immunogenic peptides homologous to Aβ according to the present invention are designed to have reduced fibrillogenic potential while maintaining the two major immunogenic sites of Aβ peptides, which are residues 1-11 and 22-28 of Aβ1-42 based on the antigenic index of Jameson et al. (1988) and results/observations obtained in the laboratory of the present inventors.

In one embodiment, the non-amyloidogenic peptide comprises the first thirty amino acid residues (SEQ ID NO:1) of Ab1-42, wherein at least one of the hydrophobic residues at positions 17-21 of SEQ ID NO:1 are substituted with charged residues Lys, Asp, or Glu, or with residues Pro, Gly, or Ser.

In another embodiment, the non-amyloidogenic peptide comprises the first thirty amino acid residues (SEQ ID NO:1) of Ab1-42, wherein one of the hydrophobic residues at positions 17-21 of SEQ ID NO:1 is substituted with charged residues Lys, Asp, or Glu, or with residues Pro, Gly, or Ser.

In another embodiment, the non-amyloidogenic peptide comprises the first thirty amino acid residues (SEQ ID NO:1) of Ab1-42, wherein two of the hydrophobic residues at positions 17-21 of SEQ ID NO:1 are substituted with charged residues Lys, Asp, or Glu, or with residues Pro, Gly, or Ser.

In another embodiment, the non-amyloidogenic peptide comprises the first thirty amino acid residues (SEQ ID NO:1) of Ab1-42, wherein three of the hydrophobic residues at positions 17-21 of SEQ ID NO:1 are substituted with charged residues Lys, Asp, or Glu, or with residues Pro, Gly, or Ser.

In another embodiment, the non-amyloidogenic peptide comprises the first thirty amino acid residues (SEQ ID NO:1) of Ab1-42, wherein four of the hydrophobic residues at positions 17-21 of SEQ ID NO:1 are substituted with charged residues Lys, Asp, or Glu, or with residues Pro, Gly, or Ser.

In another embodiment, the non-amyloidogenic peptide comprises the first thirty amino acid residues (SEQ ID NO:1) of Ab1-42, wherein five of the hydrophobic residues at positions 17-21 of SEQ ID NO:1 are substituted with charged residues Lys, Asp, or Glu, or with residues Pro, Gly, or Ser.

By modifying at least one residue at positions 17-21 of Ab1-30 (SEQ ID NO:1) with Lys, Asp, Glu, Pro, Gly, or Ser, which are residues that have a low probability of adopting β-sheet conformation, the fibrillogenic potential of the peptide is greatly reduced. SEQ ID NOs:12 and 13 are examples of such modified Aβ1-30. Furthermore, the presence of a series of Lys or Asp residues at the N-terminus and/or C-terminus of the synthetic peptide of the present invention further enhances immunogenicity (Werdelin, 1981) and reduce the propensity of the synthetic peptide to adopt a β-sheet conformation and form amyloid fibrils/deposits. The coupling of lysine residues to Aβ peptides of 4 to 8 residues in length has recently been proposed by Pailitto et al. (1999) in the design of anti-β-sheet peptides or Aβ fibrillogenesis inhibitors, but the use of Pallitto's peptides as immunogens has never been proposed. Polycationic amino acids have been previously used to enhance protein transport into cells by endocytosis/phagocytosis processes (Martinez-Fong et al., 1994; Wang et al., 1989; Shen et al., 1985; Peterson et al., 1984; Deierkauf et al., 1977; DiNicola et al., 2000). Buschle et al., (1997) reported that polycationic amino acids enhanced uptake of peptides by antigen presenting cells, thereby initiating an immune response. They also reported that, whereas peptide uptake mediated by polylysine appears to be due to an at least transient permeabilization of cell membranes, peptide delivery in the presence of polyarginine may rely on endocytic processes.

The synthetic immunogenic but non-amyloidogenic peptide homologous to Aβ according to the present invention, which is not considered to be a peptide inhibitor of Aβ fibrillogenesis, is represented by the formula $$(A)_m\text{-}(N\text{-}Xaa_1Xaa_2Xaa_3Xaa_4Xaa_5\text{-}C)_n\text{-}(B)_p$$

wherein: m is 0, 4, 5, 6, 7, 8, 9, or 10;
p is 0, 4, 5, 6, 7, 8, 9, or 10;
A is Lys or Asp;
B is Lys or Asp;
n is 1 or 2;
N is residues 1-16 of SEQ ID NO:1;
C is residues 22-30 of SEQ ID NO:1;
$Xaa_1$, $Xaa_2$, $Xaa_3$, $Xaa_4$, and $Xaa_5$ are Leu, Val, Phe, Phe, and Ala, respectively, in which zero, one, two, three, four, or five of residues $Xaa_1$, $Xaa_2$, $Xaa_3$, $Xaa_4$, and $Xaa_5$ is substituted with Lys, Asp, Glu, Pro, Gly, or Ser; and
when zero residues are substituted, then either or both of m or p is not zero.

Some exemplary amino acid sequences of the peptide represented by the above formula are presented and identified as SEQ ID NOs:2-5 and 7-10.

The basic thirty amino acid sequence (Aβ1-30) in which zero or at least one of residues 17-21 are substituted is represented in the above formula by N-$Xaa_1Xaa_2Xaa_3Xaa_4Xaa_5$-C. This thirty amino acid residue segment can be repeated (n is 2) in the synthetic peptide according to the present invention. Preferably, a polylysine or polyaspartate segment of 4 to 10 residues is present at the N-terminus and/or the C-terminus of the peptide. When no residues are substituted in residues 17-21 of Aβ1-30, the peptide has a polylysine or polyaspartate segment of 4 to 10 residues at the N-terminus and/or C-terminus. If a polylysine or polyaspartate segment is not present at the C-terminus, then the C-terminus is preferably amidated, as exemplified by SEQ ID NO:6 as a preferred embodiment. SEQ ID NO:11 is an embodiment of an unsubstituted Aβ1-30 peptide with a polylysine or polyaspartate segment of 4 to 10 residues at the C-terminus.

Furthermore, when m is 0, the N-terminal polylysine or polyaspartate segment of 4 to 10 residues is absent, and it is then preferred that either the C-terminus of the peptide be amidated to reduce the possibility that the C-terminal charge of the peptide would reduce the immunogenicity of the residue 22-28 region of Aβ or that a polylysine or polyaspartate segment of 4 to 10 residue be present at the C-terminus. Another preferred embodiment of the synthetic immunogenic but non-amyloidogenic peptide according to the present invention is as follows:
when m is not zero, p is zero;
when p is not zero, m is zero; and
$Xaa_1$, $Xaa_2$, $Xaa_3$, $Xaa_4$, and $Xaa_5$ are Leu, Val, Phe, Phe, and Ala, respectively, in which at least one residue of $Xaa_1$, $Xaa_2$, $Xaa_3$, $Xaa_4$, and $Xaa_5$ is substituted with Pro, Asp, Glu, Lys, Gly, or Ser (for example, SEQ ID Nos:2-5 and 7-10).
The invention provides for such synthetic immunogenic but non-amyloidogenic peptides where all residues of the peptide are L-amino acids or D-amino acids.

In addition, the invention provides, in one embodiment, a method of reducing amyloidosis comprising the step of administering a composition comprising a synthetic immunogenic but non-amyloidogenic peptide homologous to amyloid β, thereby reducing amyloidosis. In one embodiment, the synthetic peptide includes the first thirty amino acid residues of Aβ1-42 (SEQ ID NO:1), where zero to five of residues 17-21 are substituted with Lys, Asp, Glu, Pro, Gly, or Ser and preferably further includes an N-terminal and/or C-terminal segment of 4-10 Lys or Asp residues.

In another embodiment, this invention provides a method of treating or preventing amyloid plaque forming diseases or amyloidoses by the use of a synthetic immunogenic but not deposit forming polypeptide or peptide homologous to the protein which forms the amyloid plaque. In one embodiment, the protein is homologous to the full length protein or peptide, in another embodiment, it includes only a portion of the protein or peptide which forms the amyloid plaque. In one embodiment, at least one residue is substituted with a different amino acid so as to decrease fibrillogenicity and in another embodiment it further includes a polylysine or polyaspartate segment (of 4-10) residues at the N-terminal and or the C-terminal.

The invention provides, in one embodiment, a method of reducing amyloidosis comprising the step of administering a pharmaceutical composition comprising a synthetic immunogenic but non-amyloidogenic peptide homologous to amyloid β, thereby reducing amyloidosis. In one embodiment, the synthetic peptide includes the first thirty amino acid residues of Aβ1-42 (SEQ ID NO:1), where zero to five of residues 17-21 are substituted with Lys, Asp, Glu, Pro, Gly, or Ser and preferably further includes an N-terminal and/or C-terminal segment of 4-10 Lys or Asp residues.

Prion

The synthetic immunogenic but non-deposit-forming polypeptides or peptides homologous to human or bovine prion protein (PrP) according to the present invention are designed with considerations similar to the synthetic immunogenic but non-amyloidogenic peptide homologous to Aβ according to the present invention. However, one embodiment of the polypeptide or peptide homologous to human or bovine prion protein is directed to a full-length human or bovine prion protein in which one to five residues, preferably four or five residues, of human prion residues 121, 122, 128, 129, and 130, of SEQ ID NO:21 or of bovine prion residues 132, 133, 139, 140, and 141 of SEQ ID NO:30 is substituted with Pro, Glu, Asp, Lys, Gly, or Ser, more preferably Pro, Glu, Asp, or Lys. In addition, when more than one residue is to be substituted, it is preferred that the same amino acid residue is used for all substitutions.

It has been reported that the region of residues 90-144 of human PrP is important for initiating prion disease (Kanecko et al., 2000), whereas residues 23-89 and 141-176 are not required for infectivity. Accordingly, the embodiment of a full-length prion protein with one to five amino acid substitutions retains the epitopes located at approximately residues 93-119 145-174, and 172-201 that were previously reported to be effective in raising antibodies. Any substitutions made in the 90-144 region reported to be important in initiating prion disease in humans, which corresponds to the region of residues 93-156 in bovine PrP, is designed to replace residues that have a high propensity for forming β-sheets, such as Val, Ile, Tyr, Trp, Leu, Thr, Gln, and Met, according to Chou and Fasman with residues that have a low propensity for forming β-sheets, such as Pro, Glu, Asp, Lys, Gly, or Ser. The choice of residues 121, 122, 128, 129, and 130 of SEQ ID NO:21 and residues 132, 133, 139, 140, and 141 of SEQ ID NO:30 for substitution with residues that have a low propensity for forming β-sheets (1) avoids disturbing epitopes identified to be effective in raising antibodies as well as the epitope at residues 132-140 of human PrP to which the binding of an antibody prevents formation of the abnormal scrapie form of prion, protein ($PrP^{Sc}$) in vitro (Peretz et al., 2001) and (2) results in a polypeptide that is immunogenic but has a much reduced propensity for forming toxic prion deposits.

An alternative to the full-length substituted/modified human or bovine PrP for use as a synthetic immunogenic but non-deposit forming polypeptide or peptide homologous to human or bovine PrP, is a segment of the sequence of the full-length unmodified or substituted/modified human (SEQ ID NO:32) or bovine (SEQ ID NO:33) PrP, containing at least residues 90 to 144 of SEQ ID NO:32 or at least residues 93 to 156 of SEQ ID NO:33, alone or joined at its N-terminus and/or C-terminus to a polyaspartate or a polylysine of 4 to 10 residues in length.

Additional preferred embodiments of the synthetic immunogenic but non-deposit-forming peptide homologous to human or bovine PrP include peptides of residues 90 to 144 of SEQ ID NO:21 or of residues 93 to 156 of SEQ ID NO:30 or fragments of the peptides, where one to five residues but preferably four or five residues are substituted, and/or a polylysine or polyaspartate of 4 to 10 residues in length is joined at the N-terminal and/or C-terminal end of the peptide. These additional preferred embodiments are represented by the formula $$(A)_m\text{-}(N\text{-}Xaa_1Xaa_2GlyGlyLeuGlyGlyXaa_3Xaa_4Xaa_5\text{-}C)_n\text{---}(B)_p$$

wherein: m is 0, 4, 5, 6, 7, 8, 9, or 10;
p is 0, 4, 5, 6, 7, 8, 9, or 10;
A is Lys or Asp;
B is Lys or Asp;
n is 1 or 2;
N represents residues 90-120 of SEQ ID NO:21;
C represents residues 131-144 of SEQ ID NO:21;
$Xaa_1$, $Xaa_2$, $Xaa_3$, $Xaa_4$, and $Xaa_5$ are Val, Val, Tyr, Met, and Leu, respectively, in which zero or one to five, preferably four or five, of residues $Xaa_1$, $Xaa_2$, $Xaa_3$, $Xaa_4$, and $Xaa_5$ is substituted with Pro, Glu, Asp, Lys, Gly, or Ser; and
when zero residue is substituted, then either or both m and p is not zero (SEQ ID NOs: 34-39).

Where the peptide homologous to bovine PrP is used for administration in cows, N represents residues 93-131 of SEQ ID NO:30 and C represents residues 142-156 of SEQ ID NO:30 and the peptides have the sequences of SEQ ID NOs: 40-45. The presence or absence of polylysine or polyaspartate at the N-terminus and/or C-terminus thereof or the presence or absence of amidation at the C-terminus is as discussed above for the synthetic immunogenic but non-amyloidogenic peptide homologous to Aβ.

Another embodiment of the synthetic immunogenic but non-deposit-forming polypeptide/peptide homologous to human or bovine PrP is where all residues of the polypeptide/peptide are D-amino acid residues.

Amylin

The synthetic but non-deposit-forming peptide homologous to human amylin is also designed with considerations similar to the synthetic but non-amyloidogenic peptide homologous to Aβ according to the present invention. Human amylin is a 37 amino acid peptide having the amino acid sequence of SEQ ID NO:46 and containing an amyloidogenic region between residues 20 to 29 of SEQ ID NO:46. Mouse amylin is also 37 residues in length but having the amino acid sequence of SEQ ID NO:47, which differs from human amylin at residues 18, 23, 25, 26, 28, and 29. Unlike human amylin, mouse amylin does not form fibril, most likely because three of the residues within the region of residues 20 to 29 differs from human amylin in that they are proline residues.

The same approach that is applied to the peptides homologous to Aβ or prion protein is applied here with respect to human amylin residues 23, 26, and 27 of SEQ ID NO:46, where any one or more of these three residues having a high propensity for forming β-sheets according to Chou and Fasman is substituted with Pro, Glu, Asp, Lys, Gly, or Ser residues which have a low propensity of forming β-sheets. The preferred embodiments of the synthetic immunogenic but non-amyloidogenic (non-deposit-forming) peptide homologous to human amylin according to the present invention are represented by the formula $$(A)_m\text{-}(N\text{-}Xaa_1GlyAlaXaa_2Xaa_3\text{-}C)_n\text{---}(B)_p$$

wherein: m is 0, 4, 5, 6, 7, 8, 9, or 10;
p is 0, 4, 5, 6, 7, 8, 9, or 10;
A is Lys or Asp;
B is Lys or Asp;
n is 1 or 2;
N represents residues 1-22 of SEQ ID NO:46;
C represents residues 28-37 of SEQ ID NO:46;
$Xaa_1$, $Xaa_2$, and $Xaa_3$ are Phe, Ile, and Leu, respectively, in which zero, one, two or three of residues $Xaa_1$, $Xaa_2$, and $Xaa_3$ is substituted with Pro, Asp, Glu, Lys, Gly, or Ser; and
when zero residues is substituted, then either or both m and p is not zero (SEQ ID NOs:48-53).

Similar to the synthetic immunogenic polypeptides/peptides homologous to Aβ or PrP according to the present invention as discussed above, another embodiment of the synthetic immunogenic peptide homologous to human amylin is where all residues are D-amino acids.

α-Synuclein

Human α-synuclein is 140 amino acid residues in length (SEQ ID NO:54). The N-terminus contains imperfect 11-amino-acid repeats with the consensus sequence KTKEGV (corresponding to residues 32-37 of SEQ ID NO:54). Following the repeats is a hydrophobic intermediate region and a negatively charged C-terminus. Full-length α-synuclein is found in the filaments of Lewy bodies, its C-terminal region being exposed, whereas the amino-terminal region is buried and exposed only at one end. Assembly of α-synuclein occurs through the repeats in the amino-terminus, whereas the carboxy-terminal region inhibits assembly. The transformation of soluble α-synuclein to its fibrillar disease-associated form requires a conformational change (increased β-sheet content).

The synthetic immunogenic but non-deposit-forming polypeptide or peptide homologous to human α-synuclein according to the present invention is a polypeptide of SEQ ID NO:55 in which one or more of three sets of valine residues, (1) residues 37 and 40, (2) residues 48, 49, and 52, and (3) residues 70, 71, and 74 is substituted with all Glu, all Asp, all Pro, all Lys, all Gly, or all Ser residues. The substitutions makes the polypeptide still immunogenic but with a low propensity to form toxic protofibrils and/or aggregates.

Alternatively, shorter synthetic peptides which consist of either (1) the first N-terminal 30 to 36 residues of the human α-synuclein of SEQ ID NO:54, alone or joined at its N-terminal and/or C-terminal to a polylysine or polyaspartate segment of 4 to 10 residues in length or (2) the last C-terminal 30 to 66 residues of the human α-synuclein of SEQ ID NO:54, alone or joined at its N-terminus and/or C-terminus to a polylysine or polyaspartate segment of 4 to 10 residues in length can be used as the synthetic immunogenic peptide of the present invention. As an additional embodiment, the residues of the full-length modified α-synuclein or the shorter synthetic peptides of the present invention may all be D-amino acids.

The term "Lewy bodies" as used herein refers to intracytoplasmic, eosinophilic, round to elongated inclusions mainly composed of α-synuclein. Lewy bodies can be found in vacuols of injured or fragmented neurons, and are indicative of Parkinson's Disease (PD), variant of Alzheimer's disease with Lewy bodies, and dementia with Lewy bodies (DLB).

Polyglutamine

According to the present invention, the synthetic immunogenic but non-deposit-forming polypeptide or peptide homologous to polyglutamine repeats in proteins that are associated with neurodegenerative movement disorders has a polyglutamine segment of 30-200 glutamine residues in length joined at its N-terminus and/or C-terminus to a polylysine or polyaspartate segment of 4-10 residues in length.

This aspect of the present invention also encompasses a method for inducing an immune response to a protein with polyglutamine repeats that is associated with neurodegenerative movement disorders, where the method involves administering to a human subject in need thereof an immunizing composition containing a polyglutamine repeat-containing polypeptide or peptide of the present invention.

Peptide Design

Those of skill in the art will also appreciate that peptidomimetics of the synthetic immunogenic but non-deposit-forming polypeptide or peptide of the present invention, where the peptide bonds are replaced with non-peptide bonds, can also be used. Peptidomimetics can have various different structures (Ripka et al., 1998). For example, peptidomimetics can be: (1) peptide analogues containing one or more amide bond replacements (Spatola, 1983); (2) peptide analogues with various conformational restrains (Hart and Rich 1996), (3) novel structures that replace the entire peptide backbone while retaining isosteric topography of the peptide (Farmer, 1980), and (4) various heterocyclic natural products or screening leads that mimic the function of the natural peptide (Fletcher and Campell, 1998). Any suitable peptidomimetic can be used in the context of the present invention.

Antibodies to peptides wherein the amino acids are in D-form (i.e., D-amino acids) recognize also the corresponding L-form peptide, and vice versa (Benkirane et al., 1993). Accordingly, in one embodiment of the synthetic immunogenic but non-amyloidogenic peptide according to the present invention, all residues of the peptide are D-amino acids. The amino acids being in D-form would also have the effect of enhancing the stability of the peptide. These D-amino acids can be in the same order as the L-form of the peptide or assembled in a reverse order from the L-form sequence to maintain the overall topology of the native sequence (Ben-Yedidia et al., 2002).

The reduced fibrillogenic or reduced deposit-forming potential for the synthetic polypeptide or peptide according to the present invention can be readily determined by measuring the β-sheet conformation of the polypeptides/peptides using conventional techniques such as circular dichroism spectra, FT-IR, and electron microscopy of polypeptide or peptide suspensions.

It is also well-known that immunogens must be presented in conjunction with major histocompatibility (MHC) class II antigens to evoke an efficient antibody response. The MHC class II antigens produced by antigen-presenting cells (APCs) bind to T cell epitopes present in the immunogen in a sequence specific manner. This MHC class II-immunogen complex is recognized by $CD4^+$ lymphocytes ($T_h$ cells), which cause the proliferation of specific B cells capable of recognizing a B cell epitope from the presented immunogen and the production of B cell epitope-specific antibodies by such B cells.

Accordingly, in one embodiment, the immunogenicity of the synthetic peptides of the present invention can be increased by forming a conjugate with an immunostimulatory polymer molecule such as mannan (polymer of mannose), glucan (polymer of β1-2 glucose), tripalmitoyl-S-glycerine cysteine, and peptides which are currently approved for use in vaccines in humans. Such peptides, approved for use in vaccines, provide strong T helper cell ($T_h$) epitopes from potent immunogens such as tetanus toxin, pertussis toxin, the measles virus F protein, and the hepatitis B virus surface antigen (HBsAg). The $T_h$ epitopes selected to be conjugated to the synthetic peptide are preferably capable of eliciting T helper cell responses in large numbers of individuals expressing diverse MHC haplotypes. These epitopes function in many different individuals of a heterogeneous population and are considered to be promiscuous $T_h$ epitopes. Promiscuous $T_h$ epitopes provide an advantage of eliciting potent antibody responses in most members of genetically diverse population groups.

Moreover, the T helper cell epitopes conjugated/cross-linked to the synthetic peptide of the present invention are also advantageously selected not only for a capacity to cause immune responses in most members of a given population, but also for a capacity to cause memory/recall responses. When the mammal is human, the vast majority of human subjects/patients receiving immunotherapy with the synthetic peptide of the present invention will most likely already have been immunized with the pediatric vaccines (i.e., measles+mumps+rubella and diphtheria+pertussis+tetanus vaccines) and, possibly, the hepatitis B virus vaccine. These patients have therefore been previously exposed to at least one of the $T_h$ epitopes present in pediatric vaccines. Prior exposure to a $T_h$ epitope through immunization with the standard vaccines should establish $T_h$ cell clones which can immediately proliferate upon administration of the synthetic peptide (i.e., a recall response), thereby stimulating rapid B cell responses to Aβ peptides and amyloid deposits.

While the $T_h$ epitopes that may be used in the conjugate with the synthetic peptide of the invention are promiscuous, they are not universal. This characteristic means that the $T_h$ epitopes are reactive in a large segment of an outbred population expressing different MHC antigens (reactive in 50 to 90% of the population), but not in all members of that population. To provide a comprehensive, approaching universal, immune reactivity for the synthetic non-deposit-forming peptide according to the present invention, a mixture of conjugates with different $T_h$ epitopes cross-linked to a synthetic peptide can be prepared. For example, a combination of four conjugates with promiscuous $T_h$ epitopes from tetanus and pertussis toxins, measles virus F protein and HBsAg may be more effective.

The $T_h$ epitopes in the immunostimulatory peptide cross-linked to the synthetic non-deposit-forming peptide according to the present invention include hepatitis B surface antigen T helper cell epitopes, pertussis toxin T helper cell epitopes, tetanus toxin T helper cell epitopes, measles virus F protein T helper cell epitope, *Chlamydia trachomitis* major outer membrane protein T helper cell epitopes, diphtheria toxin T helper cell epitopes, *Plasmodium falciparum* circumsporozoite T helper cell epitopes, *Schistosoma mansoni* triose phosphate isomerase T helper cell epitopes, *Escherichia coli* TraT T helper cell epitopes and are disclosed in U.S. Pat. No. 5,843,446, the entire disclosure of which is incorporated herein by reference.

Figure 10:
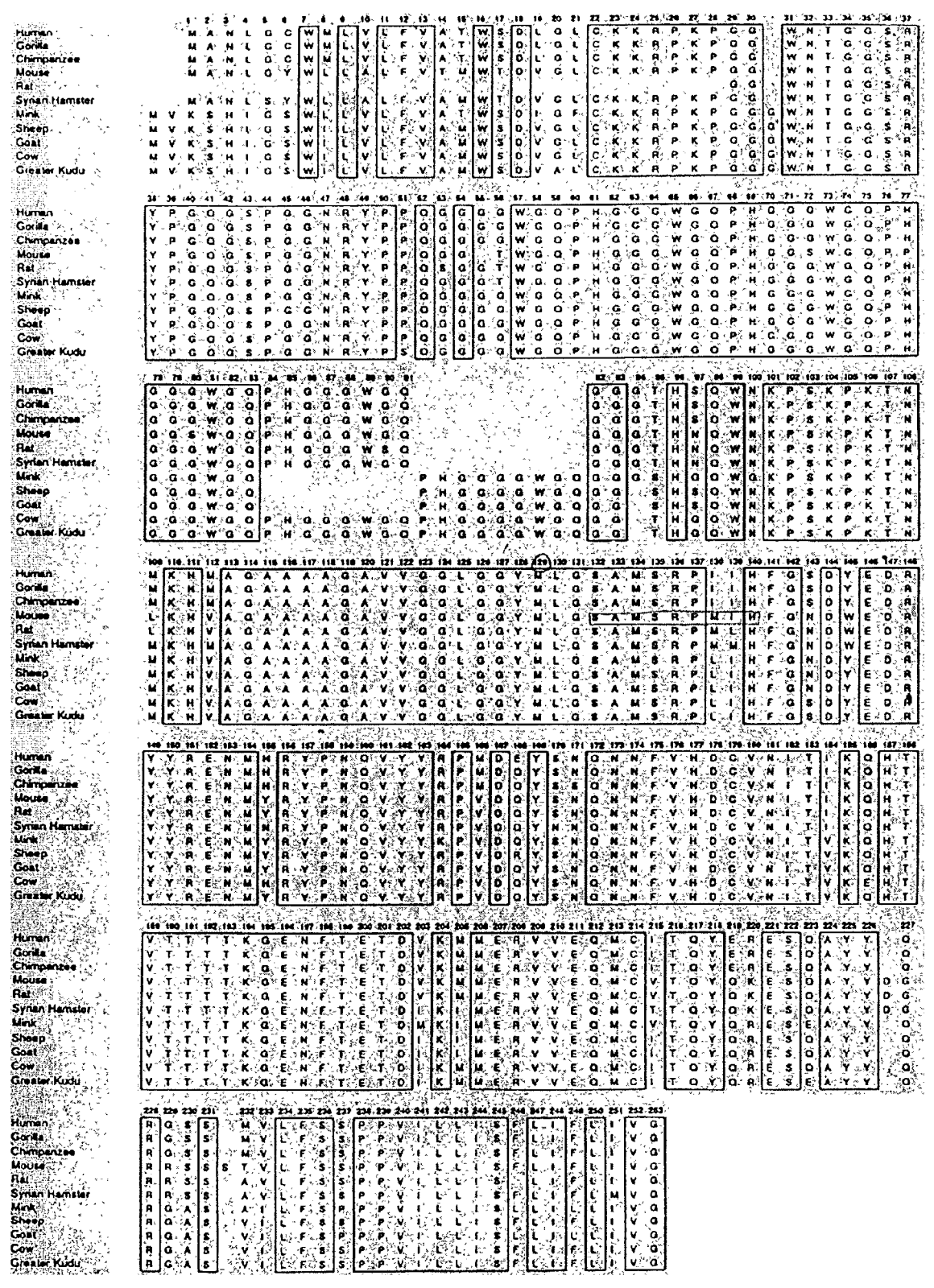

Peptide Orthologues. In a particular embodiment, the invention provides immunizing compositions based on orthologues to amyloid proteins. Because it is expected that mammalian species such mouse, rat, sheep, goat, mink, Syrian hamster, and greater Kudu (an antelope) do not transmit prion disease to humans, an immunizing composition with a prion protein or an immunogenic fragment thereof from such a mammalian species, like an immunizing composition with a synthetic immunogenic but non-deposit forming polypeptide or peptide homologous to human PrP, can be administered to a human subject in need thereof to induce an immune response to prion protein and prion deposits. From the amino acid alignment shown in FIG. 10, it is further expected that a prion protein, where the conserved amino acid residues that correspond to those amino acids substituted in the modified human PrP of SEQ ID NO:32 are likewise substituted, can also be administered to a human subject to induce an immune response to prion protein and prion deposits. For instance, conserved residues 120, 121, 127, 128, and 129 of mouse PrP correspond to residues 121, 122, 128, 129, and 130 of human PrP and can be likewise substituted.

Similarly, in a method for inducing an immune response to PrP and prion deposit in a bovine subject, an immunizing composition with a synthetic immunogenic but non-deposit-forming polypeptide/peptide homologous to bovine PrP according to the present invention or an immunizing composition with a prion protein, or immunogenic fragment thereof, from a mammalian species that does not transmit prion disease to cows can be administered. The prion protein or fragment thereof from a mammalian species that does not transmit prior disease to cows may be modified at either or both termini or at the corresponding conserved amino acid residues according to the synthetic immunogenic but non-depositing forming polypeptide/peptide homologous to bovine PrP.

In a method for inducing an immune response to amylin and amylin fibrils, an immunizing composition with a synthetic immunogenic but non-deposit-forming peptide homologous to human amylin according to the present invention or an immunizing composition with an amylin from a mammalian species that does not form amylin fibrils, such as rodents, is administered to a human subject in need thereof.

With regard to the method for inducing an immune response to α-synuclein and deposits containing α-synuclein such as Lewy bodies, the synthetic immunogenic but non-deposit-forming polypeptide/peptide homologous to human α-synuclein or an α-synuclein from a mammalian species which does not form Lewy bodies, such as rodents (mouse, rat, hamster) is administered in an immunizing composition to a human subject in need thereof.

Peptide Preparation

It will be appreciated by those of skill in the art that the term "synthetic" as used with the peptide of the present invention means that it is either chemically synthesized or is produced in an organism only when the host organism is genetically transformed from its native state to produce the peptide. The synthetic peptides of the present invention can be made by synthetic chemical methods which are well known to the ordinary skilled artisan. Accordingly, the synthetic peptides can be synthesized using the automated Merrifield techniques of solid phase synthesis with either t-Boc or F-moc chemistry on Peptide Synthesizers such as an Applied Biosystems Peptide Synthesizer.

Alternatively, polypeptides or longer peptides can be synthesized by well-known recombinant DNA techniques. Any standard manual on DNA technology provides detailed protocols to produce the synthetic polypeptides/peptides of the invention. To construct a nucleotide sequence encoding a synthetic polypeptide/peptide of the present invention, the amino acid sequence is converted into an encoding nucleic acid sequence, and preferably using optimized codon usage for the organism in which the polypeptide/peptide will be expressed. Next, a synthetic gene is made, typically by synthesizing overlapping oligonucleotides which encode the peptide and any regulatory elements, if necessary. The synthetic gene is inserted in a suitable cloning vector and recombinant clones are obtained and characterized. The synthetic polypeptide/peptide of the present invention is then expressed under suitable conditions appropriate for the selected expression system and host, and the desired polypeptide/peptide is purified and characterized by standard methods.

An immunostimulatory peptide that can be cross-linked to the synthetic non-deposit-forming peptide of the invention is also obtainable from the invasin protein of a *Yersina* species. The invasins of the pathogenic bacteria *Yersina* spp. are outer membrane proteins which mediate entry of the bacteria into mammalian cells (Isberg et al., 1990). Invasion of cultured mammalian cells by the bacterium was demonstrated to require interaction between the *Yersina* invasin molecule and several species of the β1 family of integrins present on the cultured cells (Tran Van Nhieu et al., 1991) Since T lymphocytes are rich in β1 integrins (especially activated immune or memory T cells) the effects of invasin on human T cell have been investigated (Brett et al., 1993). It is thought that integrins facilitate the migration of immune T cells out of the blood vessels and through connective tissues to sites of antigenic challenge through their interaction with extracellular matrix proteins including fibronectin, laminin and collagen. The carboxy-terminus of the invasin molecule was found to be co-stimulatory for naive human $CD4^+$ T in the presence of the non-specific mitogen, anti-CD3 antibody, causing marked proliferation and expression of cytokines. The specific invasin domain which interacts with the β1 integrins to cause this stimulation also was identified (Brett et al., 1993). Because of the demonstrated T cell co-stimulatory properties associated with this domain, it can be cross-linked to the synthetic peptide of the present invention to enhance immunogenicity.

Many of the outer membrane proteins of Gram-negative bacteria are both lipid-modified and very immunogenic. Because of the apparent correlation between covalent lipid linkage and immunogenicity, tripalmitoyl-S-glycerine cysteine ($Pam_3Cys$), a lipid common to bacterial membrane proteins, can be coupled to the synthetic polypeptides/peptides in a conjugate to also enhance immunogenicity.

Adjuvants

Immunogenicity can further be significantly improved if the synthetic polypeptides/peptides are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses, e.g. to vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum as well. Particularly suitable amuminum-based adjuvants include Alhydrogel® and Adju-Phos® (both from Superfos Biosector, Denmark).

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

U.S. Pat. No. 4,855,283 teaches glycolipid analogues including N-glycosylamides, N-glycosylureas and N-glycosylcarbamates, each of which is substituted in the sugar residue by an amino acid, as immuno-modulators or adjuvants. U.S. Pat. No. 4,258,029 teaches that octadecyl tyrosine hydrochloride (OTH) functions as an adjuvant when complexed with tetanus toxoid and formalin inactivated type I, II and III poliomyelitis virus vaccine. Also, Nixon-George et al., 1990, reported that octadecyl esters of aromatic amino acids complexed with a recombinant hepatitis B surface antigen enhanced the host immune responses against hepatitis B virus.

The addition of exogenous adjuvant/emulsion formulations which maximize immune responses to the synthetic non-deposit-forming polypeptides/peptide are preferred. The adjuvants and carriers that are suitable are those: (1) which have been successfully used in Phase I human trials; (2) based upon their lack of reactogenicity in preclinical safety studies, have potential for approval for use in humans; or (3) have been approved for use in food and companion animals. Some of the adjuvants that are currently undergoing clinical tests are reported in Aguado et al., (1999).

Formulation and Administration

Immunotherapy regimens which produce maximal immune responses following the administration of the fewest number of doses, ideally only one dose, are highly desirable. This result can be approached through entrapment of immunogen in microparticles. For example, the absorbable suture material poly(lactide-co-glycolide) co-polymer can be fashioned into microparticles containing immunogen. Following oral or parenteral administration, microparticle hydrolysis in vivo produces the non-toxic byproducts, lactic and glycolic acids, and releases immunogen largely unaltered by the entrapment process. The rate of microparticle degradation and the release of entrapped immunogen can be controlled by several parameters, which include (1) the ratio of polymers used in particle formation (particles with higher co-glycolide concentrations degrade more rapidly); (2) particle size, (smaller particles degrade more rapidly than larger ones); and, (3) entrapment efficiency, (particles with higher concentrations of entrapped antigen degrade more rapidly than particle with lower loads). Microparticle formulations can also provide primary and subsequent booster immunizations in a single administration by mixing immunogen entrapped microparticles with different release rates. Single dose formulations capable of releasing antigen ranging from less than one week to greater than six months can be readily achieved. Moreover, delivery of the synthetic polypeptide/peptide according to the present invention entrapped in microparticles can also provide improved efficacy when the microparticulate immunogen is mixed with an exogenous adjuvant/emulsion formulations.

The efficacy of the synthetic polypeptides/peptides can be established and analyzed by injecting an animal, e.g., mice or rats, with the synthetic polypeptide/peptide formulated in alum and then following the immune response to, e.g., amyloid β peptides, prion protein, amylin, α-synuclein, or polyglutamine, as described below.

Another aspect of the present invention provides an immunizing composition which includes an immunizing effective amount of one or more of the synthetic polypeptides/peptides of the invention, or conjugates thereof, and a pharmaceutically acceptable carrier, excipient, diluent, or auxiliary agent, including adjuvants. Accordingly, the synthetic polypeptides/peptides, or conjugates thereof, can be formulated as an immunizing composition using adjuvants, pharmaceutically-acceptable carriers, excipients, diluents, auxiliary agents or other ingredients routinely provided in immunizing compositions. Such formulations are readily determined by one of ordinary skill in the art and include formulations for immediate release and for sustained release, e.g., microencapsulation. The present immunizing compositions can be administered by any convenient route including subcutaneous, oral, intramuscular, or other parenteral or internal route. Similarly the vaccines can be administered as a single dose or divided into multiple doses for administration. Immunization schedules are readily determined by the ordinary skilled artisan. For example, the adjuvants or emulsifiers that can be used in this invention include alum, incomplete Freund's adjuvant, liposyn, saponin, squalene, L121, emulsigen and ISA720. In preferred embodiments, the adjuvants/emulsifiers are alum, incomplete Freund's adjuvant, a combination of liposyn and saponin, a combination of squalene and L121 or a combination of emulsigen and saponin.

The immunizing compositions of the present invention contain an immunoeffective amount of one or more of the synthetic polypeptides/peptides or conjugates thereof and a pharmaceutically acceptable carrier. Such compositions in dosage unit form can contain about 0.5 µg to about 1 mg of each peptide or conjugate per kg body weight. When delivered in multiple doses, the dosage unit form is conveniently divided into the appropriate amounts per dosage.

Immunizing compositions which contain cocktails of two or more of the synthetic polypeptides/peptides, or conjugates thereof, of the present invention enhance immunoefficacy in a broader population and thus provide a better immune response to amyloid β peptides and amyloid fibrils, to prion proteins and prion deposits, to amylin and amylin deposits, or to α-synuclein and deposits containing α-synuclein. Other immunostimulatory synthetic polypeptide/peptide immunogens are arrived at through modification into lipopeptides so as to provide built-in adjuvanticity for potent vaccines. The immune response to synthetic polypeptide/peptide immunogens of the present invention can be improved by delivery through entrapment in or on biodegradable microparticles of the type described by O'Hagan et al (1991). The immunogens can be encapsulated with or without adjuvant, including covalently attached lipid moiety such as Pam$_3$Cys, and such microparticles can be administered with an immunostimulatory adjuvant such as Freund's Incomplete Adjuvant or alum. The microparticles function to potentiate immune responses to an immunogen and to provide time-controlled release for sustained or periodic responses, for oral administration, and for topical administration (O'Hagan et al., 1991).

A further aspect of the present invention is a method for immunization with the synthetic polypeptide/peptide or conjugate thereof of the present invention. This method according to the present invention involves administering to a mammal in need thereof, preferably human, an immunizing composition containing the synthetic polypeptide(s)/peptide (s) or conjugates thereof. With respect to induction of an immune response to amyloid β and amyloid β deposits, efficacy will be tested first in transgenic mouse models of AD such as the mouse model used in Schenk et al. (1999) or other publicly or commercially available AD transgenic mouse model.

Anti-Peptide Antibodies

Yet another aspect of the present invention provides for antibodies raised against the immunogenic polypeptides/peptides of the present invention and molecules which includes the antigen-binding portion of such antibodies.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al., (1990) and Gross et al., (1989)). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$-$V_L$ or single chain $F_v$). Both $V_H$ and $V_L$ may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al., (1975); U.S. Pat. No. 4,376, 110; Harlow et al., (1988); and Colligan et al., (1993), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al., 1984; Morrison et al., 1984; Boulianne et al., 1984; Cabilly et al., 1984; Neuberger et al., 1985; Taniguchi et al., 1985; Morrison et al., 1986; Neuberger et al., 1986; Kudo et al., 1986; Morrison et al., 1986; Sahagan et al., 1986; Robinson et al., 1987; Liu et al., 1987; Sun et al., 1987; Better et al., 1988; and Harlow et al., 1988. These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

The present invention also provides a pharmaceutical composition containing a molecule which includes the antigen-binding portion of an antibody raised against a polypeptide/peptide of the present invention, and a pharmaceutically acceptable, carrier, diluent, excipient or auxiliary agent. The formulation of pharmaceutical compositions, which formulation is conventionally used in a highly skilled art and which compositions are suitable for its intended use as a therapeutic for reducing the formation of amyloid fibrils and deposits, prion deposits, amylin deposits, deposits containing α-synuclein, or deposits of proteins with polyglutamine repeats, can be developed with only routine experimentation by those of skill in the art.

According to the present invention, the molecule which includes the antigen-binding portion of an antibody raised against the immunogenic polypeptides/peptides of the present invention can be administered to a subject in need thereof to reduce the formation of amyloid fibrils and deposits, prion deposits, amylin deposits, deposits containing α-synuclein, or deposits of proteins containing polyglutamine repeats. The site of administration, the dosage, and the schedule of administration are determined according to well-established procedures used by those of skill in the art.

As shown in Example 5, in the case of antibodies against prions, those that have a $K_D$ for $PrP^{Sc}$ lower than 2, preferably lower than 0.5, even more preferably lower than 0.1 nM; a $K_D$ for $PrP^C$ lower than 20, preferably lower than 5, even more preferably lower than 1 nM; and/or a $K_D$ for recPrP lower than 0.5, preferably lower than 0.2, even more preferably lower than 0.1 nM; are particularly preferred for vaccination or post-exposure prophylaxis against prion disease.

Testing of Peptides or Antibodies

The peptides and antibodies designed according to the present invention can be tested for various properties, including their secondary structure and their efficacy in reducing aggregation of, and eliciting immune responses directed against, peptides associated with the conformational disorders described herein. Exemplary techniques for testing are described below and in Example 1.

Secondary Structure. In one embodiment, a peptide preparation of the invention contains a relatively lower portion of β-sheets than a preparation of the disease-associated peptide. The proportion of β-sheets in a preparation can, as described in Example 1, be determined by known techniques such as circular dichroism (CD; Soto et al., 1998 and 1996, Golabek et al., 1996), or Fourier Transform InfraRed spectroscopy (FTIR; Aucouturier et al., 1999).

Aggregation, fibril formation, and/or amyloid formation. To study the tendency of a peptide preparation to aggregate or form fibrils, various established methods can be employed. For example, various concentrations of a peptide preparation can be incubated in an aqueous solution, preferably a buffer, for a predetermined time, and fibril formation thereafter measured by a Thioflavine T fluorescent assay. Thioflavine T binds specifically to amyloid and this binding produces a shift in its emission spectrum and a fluorescent enhancement proportional to the amount of amyloid formed (LeVine et al. 1993, Castaño et al., 1995; Wisniewski et al., 1991; Wisniewski et al., 1993 and 1994).

Alternative methods include spectrophotometric assays based on the specific interaction of Congo red with amyloid fibrils (Castaño et al., 1986), optionally in conjunction with electron microscopic examination after negative staining (Castaño et al., 1995; Wisniewsi et al., 1991; Wisniewski et al., 1993 and Wisniewski et al., 1994), or sedimentation assays in which soluble and aggregated peptide are separated by centrifugation, and the concentration of peptide in solution analyzed by electrophoresis or chromatography (Soto et al., 1995). The application of these and other methods for the study of fibril formation of Aβ-peptides are described in Example 1. By routine experimentation, however, these and similar methods can be modified to study fibril formation or aggregation of peptides or variants of prion proteins, amylin, α-synuclein, and polyglutamine repeats.

Neurotoxicity. Neurotoxicity of peptides and antibodies can be evaluated by use of, for example, a standard MTT assay as described by the manufacturer (Roche Molecular Biochemicals, Indianapolis, Ind.) and a human neuroblastoma cell line such as SK-N-SH). In addition, the MTT protocol described in Example 1 for evaluation of Aβ peptides can be modified to study neurotoxicity of variants of prion proteins, amylin, α-synuclein, and polyglutamine repeats.

Vaccine efficacy. Evaluation or pre-clinical optimization of peptide or antibody vaccines in eliciting an immune response preventing, delaying, or reducing the formation of the aggregates, deposits, or fibrils involving the peptides associated with confirmational disorders can advantageously be made in animal models. The animal studies can be designed to evaluate preventive or prophylactic vaccination (i.e., peptide administration before any symptom of disease) or treatment of an already existing condition (i.e., peptide administration after a disease symptom). Preferred, although nonlimiting, animal models are transgenic or non-transgenic mice and rats, as well as monkeys, dogs, cats, sheep and cattle. Preferably, the animals develop a conformational disease spontaneously, or the development of a conformational disease can be triggered, i.e., by administration of a disease agent (e.g., scrapie to induce prion disease).

Several animal models have been established for the study of conformational diseases and their progression. For example, Example 1 describes the use of the transgenic mouse model Tg2576 (Hsiao et al., 1996) to study vaccination against amyloid deposits. These animals can develop Aβ plaques at 11-13 months of age. Prophylactic vaccination is preferably initiated before any substantial amyloid burden has developed, and typically repeated weekly, biweekly, or monthly, or a combination thereof, with or without adjuvant. Other animal models for AD include the double transgenic APP/PS1 model (Holcomb et al., 1998).

Examples 3-5 describe the use of a CD-1 mouse model, which is a strain of a wild-type mouse, for investigating the delay of onset of prion disease when administering a recombinant prion peptide or anti-prion antibodies before or after injection of scrapie-infected mouse brain tissue. In this model, a preparation of prion peptides or peptide variants, or anti-prion antibodies, can be administered either before exposure to scrapie for the study of immunization, after exposure to scrapie but before onset of prion disease to study prophylactic capabilities (i.e., to delay onset of disease), and after the onset of prion disease to evalue treatment potential. Several other mouse strains that are useful for the study of prion disease are known in the art.

As for the study of amylin peptide or antibody vaccines, older cats and monkeys spontaneously develop diabetes-associated islet amyloidosis (Howard,1978; de Koning, 1993; Yano et al., 1981; and O'Brien, 1986), and at least three transgenic mouse models have been developed (Couce et al., 1996; Fox et al., 1993; D'Allessiò., 1994, and Höppener et al., 1993). These mice express the human gene for islet amyloid polypeptide (IAPP) but do not develop diabetes, and islet amyloidosis is rare (Höppener et al., 1993; Verchere et al., 1997). However, amylin deposition and diabetes can be induced in these mice by making them obese and by increasing insulin resistance by various approaches, such as by adding dietary fat (Verchere et al., 1996), by administering steroids or hormones (Couce et al., 1996), or by co-expression of obesity genes (Soeller et al., 1998; Vroom et al., 1999). These models can be used to determine if vaccination with amylin-derivatives prevents and/or reverses amylin deposition. See also Jaikaran and Clark, 2001.

Several transgenic mouse models overexpressing human α-synuclein have been developed. Although none of these models have all the features of Parkinson's disease (PD), many exhibit synucleinopathy-induced neurodegeneration. The model that most closely recapitulates the α-synuclein pathology observed in PD, expresses human α-synuclein with the mutation A53T under the mouse prion promoter (Giasson et al., 2002; Lee et al., 2002). This is the only transgenic mouse model in which α-synuclein fibrils are observed, and it is also the only mammalian PD model that develops progressive neurodegeneration resulting in cell death. Other PD models containing Lewy body-like inclusions (fibrillar α-synuclein) include rats that have received the pesticide rotenone intravenously (Betarbet et al., 2002), and drosophila expressing human α-synuclein (Feany and Bender, 2000). Various other models that develop non-fibrillar or atypical α-synuclein inclusions can also be useful to test α-synclein derived immunization approaches. See, also Dawson et al. (2002).

For the study of immunization approaches to polyglutamine repeats, an animal model of Huntington's Disease (HD) can be employed. Two types of transgenic mouse models have been developed for HD (Rubinsztein, 2002): (1) transgenics in which the mutant human gene is randomly inserted into the mouse genome; and (2) 'knock-ins' in which the mutant gene is inserted into the mouse huntingtin gene. The first mouse model of HD was developed by overexpression of exon 1 of the human huntingtin gene with long CAG-repeat expansions (Mangiarini et al., 1996). Several mouse models that recapitulate many aspects of HD, including the presence of huntingtin aggregates in the brain, have also been described (Hodgson et al., 1999; Schilling et al., 1999; Reddy et al., 1998; Yamamoto et al., 2000; Laforet et al., 2001; White et al., 1997; Shelbourne et al., 1999; Lin et al., 2001). In addition to these mouse models, drosophila models of polyglutamine expansion diseases have been developed (Kazemi-Esfarjani et al., 2000; Fernandez-Funez et al., 2000; Marsh et al., 2000; Warrick et al., 1999). See, also Rubinsztein D C, 2002.

Specific protocols for each type of peptide or antibody preparation and disease type can be designed using no more than routine experimentation combined with general knowledge in the art and the present disclosure. For example, Example 1 describes a vaccination protocol using 100 μg Aβ peptide variant per administration with or without Freund's complete or incomplete adjuvant, and Example 3 describes vaccination using bi-weekly injections of 50 μg recombinant PrP, administering Freund's complete adjuvant in conjunction with the first administration and Freund's incomplete for the subsequent ones. Typical vaccination protocols are also provided in Sigurdsson et al., (2001, Am J Pathol 2002, and 2002 (in press)). Similar experimental protocols can be used for immunizations in animal models for vaccination of diseases associated with amylin fibrils, α-synuclein fibrils and filaments, and protein aggregates containing polyglutamine repeats, e.g., huntingtin, although the adjuvant and dosages can be varied or optimized as appropriate.

Assessment of vaccination efficacy is conducted using standard methods such as histological examination using, for example, examination of sectioned tissues of interest, antibody staining techniques to visualize the extent of deposits or fibrils in selected tissues, ELISA methods for estimating plasma or tissue concentrations of the disease-associated peptide or endogenous antibodies directed to the disease-associated peptide, or testing whether deposits or aggregates of the disease-associated peptide are resistant to proteinase digestion.

Vaccine efficacy in preventing or delaying a neurodegenerative conformational disorder can also be evaluated by testing for motor coordination and/or cognitive capabilities at appropriate intervals during disease progression.

For example, locomotor activity of a vaccinated or control animal can be tested by putting the animal, typically a rodent, into a closed activity box for 5 minutes. The animal's activity in the box is detected by photoreceptors in the box, so that whenever an animal crosses the receptor, an activity count is recorded. The activity box can record activity counts per minute. See, also, Sobotka et al., 1978.

Alternatively, the ability of the animal to cross a traverse beam can be evaluated. The animal is given 1 unscored training trial, preventing injury from falling by placing a soft cover underneath the beam. An animal that falls off is placed back into the position they maintained prior to the fall. After training, each animal is tested twice. Errors are defined as footslips and recorded both numerically and using Feeney scores. See, also, Quartermain et al., 2000.

Motor coordination can also be studied using a rotarod. The animal is placed onto a clean rod (diameter 3.6 cm) for 30 seconds. With each 30-sec interval, the rotation speed is increased incrementally. Total time (including the 30-sec on the quiescent rod) and RPM when the animal fell down is recorded. A soft cover is placed beneath the apparatus to prevent potential injury from falling. Each animal is tested thrice with an intertrial interval of fifteen minutes. See, also, Quartermain et al., 2000.

As for cognitive tests, animals can be randomly split into equivalent groups and then run on a series of cognitive tests such all groups receive each test in a different sequential order. Cognitive testing can be made in various settings known in the art, e.g., radial arm mazes, linear mazes, water mazes, and goal boxes. For example, in a maze experiment, each animal can undergo a predetermined time of adaptation, consisting of 15 minutes free moving in the maze, with pieces of fruit loops in each (open) arm of the maze. Subjects are then exposed to doors. Animals are food deprived before the first adaptation with, for example, approximately ten percent body weight loss. Fruit loops are added to normal diet before deprivation schedule starts. Testing include recording correct and incorrect arms entered. Animals are placed in the center of the maze and all doors are opened. After entry into an arm, the animal must find and eat the reinforcer before the door in opened to re-enter the center of the maze. Testing ends when all arms are entered and reinforcers found. Re-entry into an arm constitutes an error. Total number of errors and time to enter all arms are recorded. Access to food is given for 3-4 hours (depending on age, body weight loss) daily. Radial arms mazes and other types of cognitive tests are described in Ammassari-Teule et al. (1985), Roullet et al. (1998), and Roullet et al. (1995).

Having now generally described the invention, the same will be more readily understood through reference to the following examples which are provided by way of illustration and is not intended to be limiting of the present invention.

EXAMPLE 1

The experiments in this example demonstrate that immunization in transgenic APP mice (Tg2576) for 7 months with a non-amyloidogenic, non-toxic Aβ homologous peptide reduced cortical and hippocampal brain amyloid burden by 89% ($p=0.0002$) and 81% ($p=0.0001$), respectively. Concurrently, brain levels of soluble Aβ1-42 were reduced by 57% ($p=0.0019$). Ramified microglia expressing interleukin-1β associated with the Aβ plaques were absent in the immunized mice indicating reduced inflammation in these animals. The materials and methods used in the experiments in this example and the experimental results are presented below.

Materials and Methods

Peptides

The peptides used (Aβ1-40, Aβ1-42, Aβ1-30-NH$_2$ (SEQ ID NO:1), and K6Aβ1-30-NH$_2$ (SEQ ID NO NO:6)) were synthesized at the Keck Foundation (Yale University, New Haven, Conn.), as described previously (Sigurdsson et al., 2000). Non-amyloidogenic peptides according to the present invention are synthesized using solid-phase tBOC (N-tert-butyloxycarbonyl) chemistry, purified by HPLC, and characterized by HPLC and laser desorption mass spectroscopy.

The peptide used for the immunizations, K6Aβ1-30-NH$_2$, maintains the two major immunogenic sites of Aβ peptides, which are residues 1-11 and 22-28 of Aβ1-42 based on the antigenic index of Jameson et al. (1998), and on preliminary results obtained in the laboratory of the present inventors. The Aβ1-30-NH$_2$ and K6Aβ1-30-NH$_2$ peptides were amidated at the C-terminus to further preserve their antigenicity.

Secondary Structure Studies

Secondary structure (α-helix, β-sheet, and random coil) of the peptides was evaluated by circular dichroism (CD) as described previously (Soto et al., 1998 and Soto et al., 1996). Results are expressed as molar ellipticity in units of deg cm$^2$ dmol$^{-1}$, and the data was analyzed by the Lincomb and CCA algorithms (Perczel et al., 1992) to obtain the percentages of different types of secondary structure.

While the secondary structure of the synthesized peptides was evaluated by circular dichroism (CD), it can also be evaluated by Fourier-Transform InfraRed spectroscopy (FTIR), using published protocols from Aucouturier et al. (1999). Although CD is sensitive to backbone conformation and FTIR is sensitive to the degree and strength of hydrogen bonding of amide groups (which is dependent of the structure), these two techniques ultimately give similar information: the percentages of different secondary structure motifs, i.e., α-helix, β-sheet, β-turn and random coil (Surewicz et al., 1993). CD is a very well-established technique for studying the secondary structure of proteins and peptides in solution, giving fairly accurate estimations of the content of different structural motifs. A major advantage of FTIR spectroscopy for structural characterization is the lack of dependence on the physical state of the sample. Samples may be examined as aqueous or organic solutions, hydrated films, inhomogeneous dispersions, aggregated materials or even proteins in solid state. Therefore, CD and FTIR are complementary for studying the secondary structure of peptides.

The experimental procedure for circular dichroism (CD) is performed according to Golabek et al., (1996) and Soto et al. (1996 and 1998) as follows: CD spectra of solutions containing synthetic peptides (1-5 μM in 300 μl of 10 mM sodium phosphate, pH 7.2) is recorded in a Jasco J-720 spectropolarimeter at 25° C. using a 0.1 cm path-length cell with double distilled, deionized water and TFE (spectroscopy grade) being used as solvents. Calibration of the instrument is performed with an aqueous solution of d-(+)-10-camphorsulfonic acid. Spectra is recorded at 1 nm intervals over the wavelength range 180 to 260 nm and buffer spectra obtained under identical conditions is subtracted.

The experimental procedure for Fourier-Transform Infra-Red Spectroscopy according to Aucouturier et al. (1999) is as follows: Solutions or suspensions containing soluble or aggregated synthetic peptides (5-10 mg/ml) will be prepared in H$_2$O and D$_2$O buffers at neutral pH, and 10 μl will be loaded into an infrared cell with CaF$_2$ plates and 6 μm path-length spacer. Spectra will be recorded with a Perkin Elmer model 2000 FTIR spectrophotometer at 25° C., as described (Aucouturier et al., 1999; Soto et al., 1995). For each spectrum, 1000 scans will be collected in the single-beam mode with 2 cm$^{-1}$ resolution and a 1 cm$^{-1}$ interval from 4000 to 1000 cm$^{-1}$. Smoothing and Fourier self-deconvolution will be applied to increase the spectral resolution in the amide I region (1700-1600 cm$^{-1}$) and the iterative fitting to Lorentzian line shapes will be carried out to estimate the proportion of each secondary structural element.

Studies of Amyloid Fibril Formation in vitro

Studies of amyloid fibril formation in vitro can be performed using published protocols from the laboratory of the present inventors (Castaño et al., 1995; Wisniewski et al., 1991; Wisniewski et al., 1993 and Wisniewski et al., 1994). Aliquots of the synthetic peptides at a concentration ranging between 25-250 μM, prepared in 0.1 M Tris, pH 7.4, can be incubated for different times, and their fibril formation compared to that of Aβ1-28, Aβ1-40 and Aβ1-42. In this example, aliquots of the peptides prepared in 0.1 M Tris, pH 7.4, were incubated for different times, and their fibril formation compared to that of Aβ1-30-NH$_2$ and Aβ1-42. In vitro fibrillogenesis was evaluated by a fluorometric assay based on the fluorescence emission by thioflavine T, as previously described by the laboratory of the present inventors (Soto et al., 1998 and Jameson et al., 1998). Thioflavine T binds specifically to amyloid and this binding procedures a shift in its emission spectrum and a fluorescent enhancement proportional to the amount of amyloid formed (LeVine et al. 1993).

Although not performed in this example, in vitro fibrillogenesis can also be evaluated by three other different methods:

(A) A spectrophotometric assay based on the specific interaction of Congo red with amyloid fibrils. After the incubation period, 2 μl of Congo red (1.5 mg/ml) will be added to each sample and incubated in the dark for 1 h. The samples will then be centrifuged at 15,000 rpm for 10 min and the absorbance of the supernatant measured at 490 nm. The amount of amyloid formed is directly proportional to the decrease in the supernatant absorbance (Castaño et al., 1986).

(B) A sedimentation assay will be used as described (Soto et al., 1995). Briefly, samples will be centrifuged at 15,000 rpm for 10 min to separate the soluble and aggregated peptide. The amount of material in solution will be analyzed by microbore HPLC using a reverse phase Vydac C4 column and a linear gradient of 3-70% acetonitrile. The percentage of aggregated peptide will be estimated by comparing the area of the peak corresponding to the soluble peptide in each incubated sample with an identical control of non-incubated sample.

(C) Additional characterization of fibrillogenesis will be performed by Congo red staining and electron microscopic examination after negative staining (Castaño et al., 1995; Wisniewsi et al., 1991; Wisniewski et al., 1993 and Wisniewski et al., 1994). For electron microscopy, the incubated samples of peptides will be placed on carbon formar-coated 300-mesh nickel grids and stained for 60 seconds with 2% uranyl acetate under a vapor of 2% glutaraldehyde. Grids will be visualized on a Zeiss EM 10 electron microscope at 80 kV. For Congo red staining, the incubated peptides will be placed onto gelatin-coated glass microscope slides and air-dried at 37° C. The slices will then be immersed in 0.2% Congo red dissolved in 80% aqueous ethanol saturated with NaCl for 60 min at room temperature, washed three times with water and visualized by polarized light microscopy.

Neurotoxicity

The potential neurotoxicity of K6Aβ1-30-NH$_2$ (1-100 µM) was evaluated at 2 and 6 days in a human neuroblastoma cell line (SK-N-SH) using the standard MTT assay as described by the manufacturer (Roche Molecular Biochemicals, Indianapolis, Ind.). Aβ 1-30-NH$_2$, Aβ1-40 and Aβ1-42 were used as control peptides. Briefly, cells were plated at 10,000 cells/100 µl culture medium per well in flat bottom, 96 well microtiter plates. The cells were allowed to attach to the plate overnight in an incubator (37° C., 5.0% CO$_2$), and then 10 µl of freshly prepared peptide solution (in nanopure H$_2$O) was added. Aβ1-42 was only partially soluble at,100 µM and was, therefore, added as a suspension at that concentration. Subsequent steps were as described in the assay protocol.

Animals

The vaccination was performed in the Tg2576 APP mouse model developed by Karen Hsiao et al. (1996). These mice develop Aβ plaques as early as at 11-13 months of age. This model was chosen over the double Tg APP/PS1 model (Holcomb et al., 1998) because the age of onset and progression of Aβ deposition in the single Tg APP mice more closely resembles that of AD. Age-matched vehicle-treated Tg mice and non-Tg littermates receiving K6Aβ1-30-NH2 were used as controls, and the animals received their first injection at 11-13 months, at which time few plaques should already be present. Four mice were in each group. The animals were maintained on a 12 h light-dark cycle, and had access to food and water ad libitum. The animal care was in accordance with institutional guidelines.

Vaccine Administration: K6Aβ1-30-NH$_2$ was supplied as trifluoroacetic acid (TFA) salt. The immunization procedure was performed as previously described by Schenk et al. (1999) except that the peptide was not incubated overnight at 37° C. before injection. Briefly, the peptide was dissolved in PBS at a concentration of 2 mg/ml and then mixed 1:1 (v/v) with the adjuvant or PBS. Complete Freund's adjuvant was used for the first injection, incomplete Freund's adjuvant for the next 3 injections, and PBS from the 5$^{th}$ injection forward. The mice received a subcutaneous injection of 100 µl of the mixture (i.e., 100 µg/100 µl) followed by a second injection two weeks later, and then monthly thereafter.

Antibody Titers: Antibody titers were determined by serial dilutions of sera using an ELISA assay as described previously (Jimenez-Huete et al., 1998), where Aβ or its derivative is coated onto microtiter wells. The titer, defined as the dilution yielding 50% of the maximum signal, was detected by a goat anti-mouse IgG linked to a horseradish peroxidase (Amersham Pharmacia Biotech, Piscataway, N.J.), and tetramethyl benzidine (Pierce, Rockford, Ill.) was the substrate.

Histology: Mice were anesthetized with sodium pentobarbital (150 mg/kg, i.p.), perfused transaortically with phosphate buffer and the brains processed as previously described (Sigurdsson et al., 1996). The right hemisphere was immersion fixed in periodate-lysine-paraformaldehyde, whereas the left hemisphere was snap frozen for measurements of Aβ levels using established ELISA methods (Mehta et al., 1998 and Mehta et al., 2000). Serial coronal sections (40 µm) were cut and five series of sections at 0.2 mm intervals were saved for histological analysis of 1) 6E10, 2) Congo red, 3) Interleukin-1β/OX42/tomato lectin, 4) GFAP, and 5) cresyl violet stained sections. 6E10 recognizes Aβ and stains both pre-amyloid and Aβ plaques (Kim et al., 1990). Congo red staining was performed to identify amyloid lesions in these animals. GFAP is a component of the glial intermediate filaments that form part of the cytoskeleton and is found predominantly in astrocytes. Microglia appear to be the major source of interleukin-1 (IL-1) within the CNS (Schobitz et al., 1994), and OX-42 recognizes CD11b on microglia, a rat equivalent of the human C3bi receptor (Robinson et al., 1986). Tomato lectin binds to poly-N acetyl lactosamine residues and has in neural tissue specific affinity for microglial cells (Acarin et al., 1994). Both astrocytes and microglia are associated with Aβ deposits. Staining with cresyl violet was performed to determine if the immunization was causing neuronal shrinkage and/or cell loss in these animals. Following sectioning, the series were placed in ethylene glycol cryoprotectant and stored at −20° C. until used.

Cresyl violet and Congo red: Mounted sections were defatted in xylene and hydrated in a gradient of ethyl alcohol and water series. Staining was performed as previously described (Sigurdsson et al., 1996 and 1997 and Soto et al., 1998)

6E10, GFAP, IL-1β and OX-42: Staining was performed as previously described (Sigurdsson et al., 1996 and Soto et al., 1998). Briefly, sections were incubated in 6E10 (kindly provided by Richard Kascsak, Institute for Basic Research) primary antibody that selectively binds to human Aβ at a 1:1000 dilution. A mouse on mouse immunodetection kit (Vector Laboratories, Burlingame, Calif.) was used where the anti-mouse IgG secondary antibody was used at a 1:2000 dilution. GFAP (1:500; Dako, Denmark), IL-1β (1:250; Endogen, Rockford, Ill.) and OX-42 (1:250; Biosource Int., Camarillo, Calif.) staining was performed the same way as the 6E10 staining, except the secondary antibody was diluted 1:1300. The sections were reacted in 3,3'-diaminobenzidine tetrahydrochloride (DAB) with or without nickel ammonium sulfate (Ni) intensification. For double labeling of IL-1β and Aβ plaques, sections were first stained for IL-1β (DAB/Ni; black) where peroxidase was the enzyme. The plaques (6E10) were then stained using the Vector Red Alkaline Phosphatase Substrate Kit I (Vector).

Tomato Lectin: Sections removed from the cryoprotectant were washed in PBS, 0.3% Triton-X-100 in PBS (PBS-Tx) and then incubated for 30 minutes in 0.3% hydrogen peroxide in PBS to quench endogenous peroxidase activity. Following 2 hours incubation with tomato lectin (10 µg/ml PBS; Vector), sections were washed in PBS-Tx and then reacted with avidin-horseradish peroxidase (Vector) for one hour. Subsequent steps were as those used for the antibody staining.

Image Analysis: Immunohistochemistry of tissue sections was quantified with a Bioquant image analysis system, and unbiased sampling was used (West et al., 1999). All procedures were performed by an individual blind to the experimental condition of the study. Cortical area analyzed was dorsomedially from the cingulate cortex and extended ventrolaterally to the rhinal fissure within the right hemisphere. The area of the grid was 800×800 µm$^2$ and amyloid load was measured in 10 frames per mouse (each: 640×480 µm$^2$), chosen randomly. Hippocampal measurements were performed on the entire hippocampus in a similar manner as the cortical analysis. The Aβ burden is defined as the percent of area in the measurement field occupied by reaction product.

Sandwich ELISA Assay for Soluble Aβ Levels: Prior to extraction of Aβ from brain tissue, 10% (w/v) homogenates were prepared in tissue homogenization buffer (20 mM Tris pH 7.4, 250 mM sucrose, 1 mM EDTA, 1 mM EGTA). Immediately before use, 1/100 volume of 100 mM phenylmethylsulfonyl fluoride stock solution (in ethanol) and 1/1000 volume of LAP (5 mg each of leupeptin, antipain and pepstatin Aβ per ml of N-N-dimethylformamide) were added to the homogenization buffer. The homogenate was then thoroughly mixed with an equal volume of 0.4% diethylamine/100 mM NaCl, then spun at 135,000×g for one hour at 4° C., and subsequently neutralized with 1/10 volume 0.5 M Tris, pH 6.8. The samples were then aliquoted, flash frozen on dry ice, and stored at −80° C. until loaded onto plates. Soluble Aβ levels were measured in the left hemisphere using monoclonal antibody 6E10 (specific to an epitope present on 1-16 amino acid residues of Aβ), rabbit antiserum R162 (specific for Aβ40) and rabbit antiserum 165 (specific for Aβ42) in a double antibody sandwich ELISA as described previously (Mehta et al., 1998 and 2000). The optical density (OD) was measured at 450 nm in a microELISA reader. The relationship between OD and Aβ40 or Aβ42 concentrations was determined by a four-parameter logistic log function. Nonlinear curve fitting was performed with KlinetiCalc program (Biotek Instruments, Inc. Winooski, Vt.) to convert OD of plasma to estimated concentrations. All samples were coded, and the investigators were blinded to group assignment until levels were measured and recorded. The detection limit of the assay is 10 pg/ml for Aβ40 and Aβ42. The percent coefficient of variation normally ranges from 8 to 14% (inter-assay) and 10 to 18% (intra-assay).

Data Analysis: The cell culture data was analyzed by one-way ANOVA, followed by a Dunnett's test for post hoc analysis (GraphPad Prism 3.0). An unbiased stereological image analysis system (Bioquant, R&M Biometrics Inc., Nashville, Tenn.) was used to determine the amyloid burden in 6E10 stained brain sections. The data for the amyloid burden and the levels of soluble Aβ within the brain were analyzed by a Student's t-test, two-tailed.

Results

Before conducting the vaccination study it was necessary to confirm that the prototype peptide, KKKKKK-Aβ1-30-NH2, had indeed less β-sheet structure, reduced fibrillogenicity compared to Aβ1-42, and that it was non-toxic in neuronal culture. The secondary structure of these peptides was determined by circular dichroism (CD), and their ability to form amyloid fibrils by a thioflavin-T fluorometric assay. An additional control peptide was Aβ1-30-NH2.

CD Assay: Compounds with high β-sheet content are more toxic and more likely to form fibrils than compounds with low β-sheet content (Pike et al., 1991). The peptide with the polylysine at the N-terminus had much less β-sheet content that the amidated Aβ1-30 or Aβ1-42 (Table 1).

The $(K)_6$-Aβ1-30-NH$_2$ peptide also does not form fibrils following incubation at 37° C. for at least 15 days. This data clearly shows that the addition of polylysine at the N-terminus alters the peptide so that the β-sheet content is much lower then either Aβ1-42 or Aβ1-30. In addition, the β-sheet content of the $(K)_6$-Aβ1-30-NH$_2$ peptide does not increase with time. The β-sheet content of Aβ1-42 increased to 55% after 96 hr., while that of $(K)_6$-Aβ1-30-NH$_2$ stayed at 16-18%.

formation by the Aβ1-42 with prolonged incubation. K6Aβ1-30-NH$_2$ did not form fibrils following incubation at 37° C. for at least 15 days.

Figure 2A:
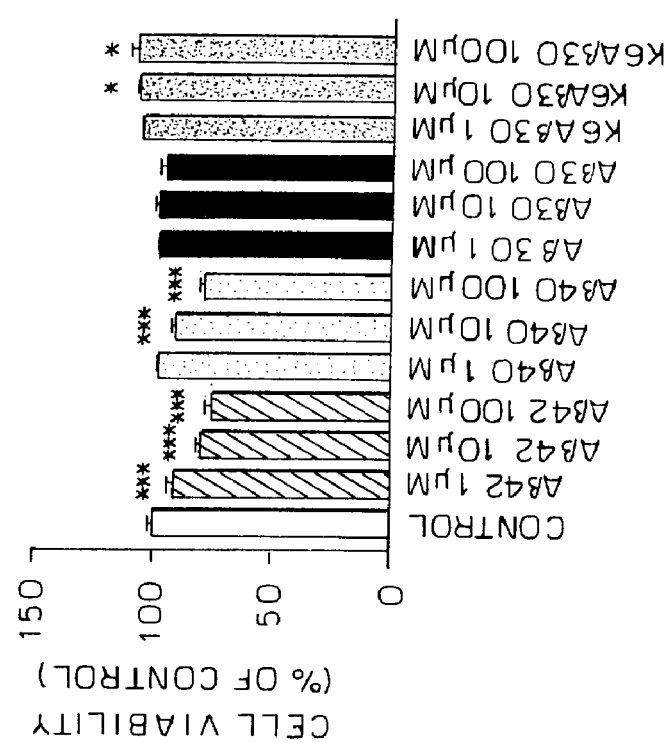
FIGS. 2A and 2B show that Aβ40 and Aβ42 are toxic to human neuroblastoma cells (SK-N-SH) in culture as determined by the MTT assay, whereas K6Aβ30-NH$_2$ has no effect at 2 days (FIG. 2A) and is slightly trophic at 6 days (FIG. 2B). *p<0.05; p<0.01; *p<0.001 compared to VEH group (one-way ANOVA).

Neurotoxicity: To further assess the safety of this vaccination approach the neurotoxicity of K6Aβ1-30-NH$_2$ was determined. K6Aβ1-30-NH$_2$ had no effect on cell viability at 2 days and was slightly trophic at 6 days (p<0.05), whereas Aβ1-40 and Aβ1-42 were toxic (p<0.05-0.001) to the human neuroblastoma cells (SK-N-SH), compared to vehicle group, as determined by the MTT assay (FIG. 2A and B). During the incubation period, aggregates were visible under the microscope only in culture wells containing Aβ1-42 (10-100 μM).

Antibody Titer: Tg2576 and their non-Tg littermates were vaccinated with K6Aβ1-30-NH$_2$ or vehicle. Almost all the mice developed antibodies against the immunogen (K6Aβ1-30-NH$_2$), that cross-reacted with Aβ1-40 and Aβ1-42. The titer, defined as the dilution yielding 50% of the maximum signal, ranged from a few hundreds to several thousands. Vehicle treated animals injected with the adjuvant and PBS did not develop antibodies against these three peptides. Non-transgenic mice had generally higher titer against all 3 peptides, and the polyclonal antibodies had higher avidity for the immunogen compared to Aβ1-40 and Aβ1-42. These findings are as expected because the immunogen is based on the human sequence of Aβ which differs in 3 amino acids from the mouse Aβ (Johnstone et al., 1991), and K6Aβ1-30-NH$_2$ that elicited the immune response should have more binding motifs for antibodies than the intact Aβ peptides.

Amyloid Burden and Associated Histopathology: The mice were killed at 18-20 months of age after 7 months treatment, and their right hemisphere was processed for histology as described (Sigurdsson et al., 1996). The brain sections were stained with cresyl violet, Congo red, tomato lectin and with antibodies against: 1) human Aβ (6E10); microglia (OX-42; IL-1β); and GFAP (anti-GFAP). Following K6Aβ1-30-NH$_2$ vaccination, cortical and hippocampal amyloid burden in the Tg mice was reduced by 89% and 81%, respectively (FIGS. 3A, 3B; 4A, 4B), as determined by stereological techniques. The total number of Congo red positive amyloid deposits was reduced in the immunized animals; however, the percentage of Aβ-immunoreactive lesions that were Congo red positive appeared to remain the same as in the non-immunized Tg mice. The clearance of the amyloid deposits appeared to be similar in other brain regions. Selected brain sections from a control mouse with high amyloid burden and an immunized mouse with reduced amyloid burden were stained with sera from several immunized and control mice, whose antibody titer ranged from zero to three thousand. As expected, with increasing titer more plaques were stained and

TABLE 1

| Time | Aβ1-42 | | | Aβ1-30-NH$_2$ | | | $(K)_6$-Aβ1-30-NH$_2$ | | |
|---|---|---|---|---|---|---|---|---|---|
| (hr) | alpha | beta-sheet | random | Alpha | beta-sheet | random | alpha | beta-sheet | random |
| 0 | 9 | 36 | 55 | 5 | 37 | 58 | 2 | 18 | 79 |
| 24 | 9 | 40 | 51 | 8 | 36 | 56 | 5 | 16 | 78 |
| 96 | 5 | 55 | 40 | 7 | 49 | 44 | 34 | 16 | 50 |

Thioflavin T assay: Aβ1-42 was already fibrillar at t=0, whereas Aβ1-30-NH$_2$ gradually formed fibrils over time (FIG. 1). The relatively high degree of thioflavin T staining of the Aβ1-30-NH$_2$ versus Aβ1-42 after 6 days reflects the known batch-to-batch variability of Aβ peptide fibril formation (Soto et al., 1995), as well as some degree of pellet the pattern was similar in both mice. There was no obvious difference between the Tg treatment groups in cresyl violet staining. Reactive astrocytes were observed associated with all amyloid plaques. Since the vehicle-treated Tg mice had a higher plaque burden, they had more clusters of astrocytes than immunized Tg mice. OX-42 staining of ramified rather than phagocytic (ameboid) microglia was predominantly observed associated with plaques. To verify that this lack of microglial phagocytes was not due to downregulation of the CD11b receptor, the binding motif of OX-42 (Robinson et al., 1986), sections from all treatment groups were stained with tomato lectin. This particular lectin binds to poly-N-acetyl lactosamine residues found predominantly in ramified and phagocytic microglial cells, in addition to endothelial- and ependymal cells (Acarin et al., 1994). These two latter cell types were stained in all the mice. The microglial lectin staining resembled the OX-42 staining. In other words, in both immunized and control Tg groups, the microglia did not have phagocytic morphology and number of ramified microglial processes per plaque appeared to be similar between immunized and non-immunized mice. On the other hand, IL-1β staining of ramified microglial cells was prominent surrounding the Aβ plaques in the control Tg mice (FIG. 3C), whereas virtually no IL-1β staining was observed in the immunized mice (FIG. 3D). Significantly, there was no indication of glomerulonephritis in hemotoxylin/eosin stained kidney sections from the K6Aβ1-30-NH$_2$ treated mice, suggesting that the mice had not developed an autoimmune disorder.

Figure 4A:
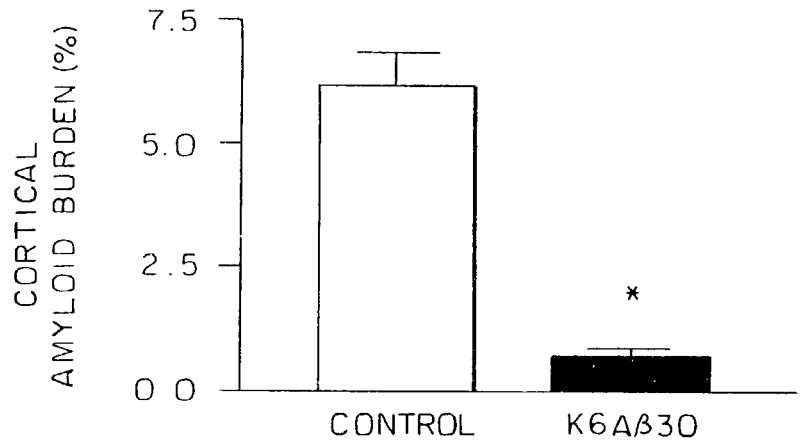
FIGS. 4A-4C show the reduction in cortical (FIG. 4A) and hippocampal (FIG. 4B) amyloid burden (6E10) following 7 months treatment with K6Aβ1-30-NH$_2$. There is an 89% reduction in cortical amyloid burden (*p=0.0002; t-test; n=4 per group) and an 81% reduction in hippocampal amyloid burden (*p=0.0001). Soluble Aβ1-42 levels (FIG. 4C) are reduced by 57% within the brains of the vaccinated mice (*p=0.0019).
Figure 4B:
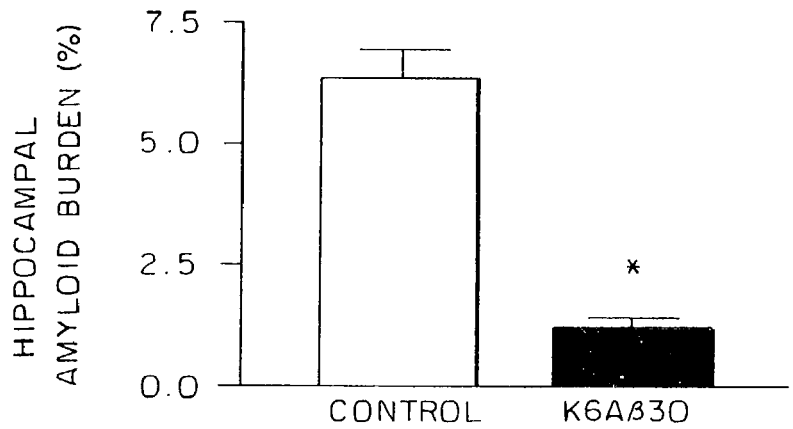
Figure 4C:
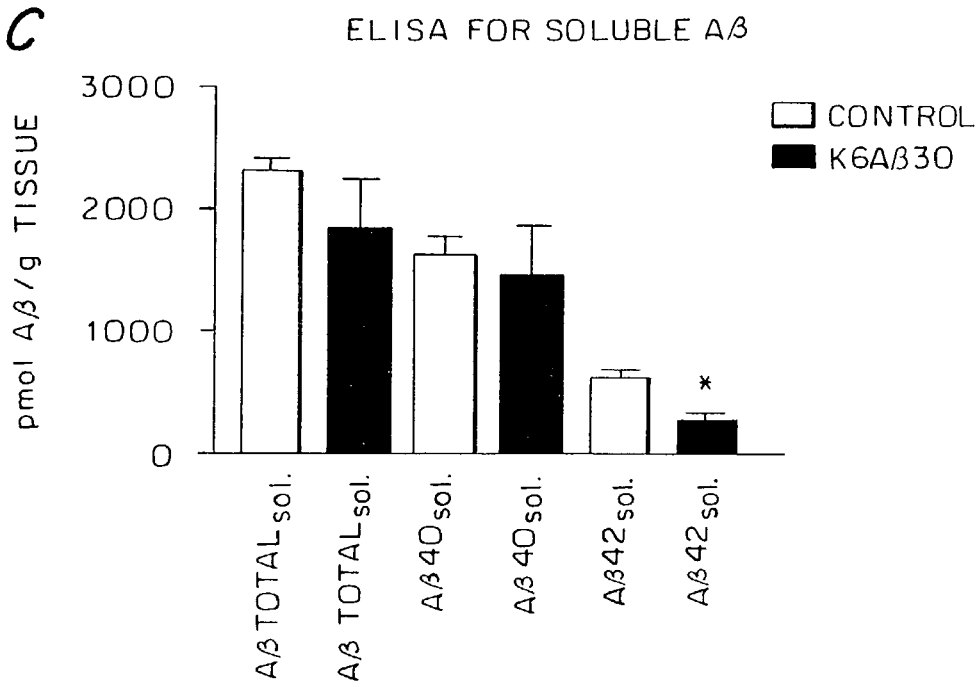

Soluble Aβ by ELISA: Measurements of soluble AD levels were performed on the left hemisphere of the mice whose right hemisphere was used for histology. Soluble Aβ1-42 was reduced by 57% following vaccination with K6Aβ1-30-NH$_2$ for 7 months (p=0.0019), compared to control group (FIG. 4C). Although there was a trend for reduced levels of soluble total Aβ and Aβ1-40 in the K6Aβ1-30 treated group, the values were not significantly different from the vehicle group.

Overall, immunization in Tg APP mice with non-amyloidogenic/non toxic (low β-sheet content) Aβ homologous peptide results in a similar reduction of amyloid burden as observed by Schenk et al. (1999) where they used a fibrillar/toxic (high β-sheet content) Aβ1-42.

Discussion

These findings demonstrate that Aβ aggregates/fibrils are not necessary to elicit a sufficient immune response that results in clearance of Aβ plaques. The use of non-fibrillar/non-toxic Aβ homologous peptides, such as K6Aβ1-30-NH$_2$, is a safer vaccination approach for humans.

The mechanism of the vaccination-induced reduction in cerebral amyloid burden is not fully understood. However, based on the passive vaccination study by Bard et al. (2000) it is likely that antibodies have a pivotal role. Interestingly, they demonstrated that there was no correlation between antibody efficacy and affinity for soluble Aβ or binding to aggregated synthetic Aβ peptide. Effective antibodies were, however, able to bind to plaques in unfixed brain sections. Janus et al. (2000), using the same protocol as Schenk et al. (1999) observed that the sera from Aβ-immunized mice preferentially stained dense core plaques rather than diffuse Aβ deposits suggesting that the antibodies may have a higher affinity for β-sheet Aβ. Based on these somewhat contradictory findings, more studies are needed on Aβ-antibody interactions that may give insight into the mechanism of antibody-mediated Aβ clearance. It is unlikely that these antibodies are affecting the production of Aβ because they do not recognize APP (Weiner et al., 2000). It is more probable that the antibodies enhance clearance of Aβ through microglial activation following antibody binding to Aβ plaques (Schenk et al., 1999 and Bard et al., 2000). Their effect may also in part be due to binding to soluble Aβ within the brain, that alters the equilibrium between deposited Aβ vs. soluble Aβ. Given the numerous reports that show that Aβ can bi-directionally cross the blood brain barrier (Zlokovic et al., 1993; Maness et al., 1994; Martel et al., 1996; Poduslo et al., 1997 and 1999; Mackic et al., 1998; Shibata et al., 2000 and Ji et al., 2001) the vaccination effect may be in part mediated through binding of the antibodies to soluble Aβ in peripheral fluids. Subsequent reduction in peripheral Aβ levels may alter the equilibrium between Aβ found within and outside the CNS that may result in efflux of Aβ out of the CNS. A recent report shows that in the Tg2576 mice, plasma levels of Aβ decrease as cerebral plaque burden increases (Kawarabayashi et al., 2001). This suggests an interaction between these two compartments that can be manipulated.

Interestingly, in the behavioral vaccination study by Morgan et al. (2000), they observed a partial reversal in cognitive deficits in APP/PS1 mice although cerebral amyloid burden as measured by immunohistochemistry was not significantly reduced. As pointed out by Morgan et al. (2000), soluble Aβ has been proposed to cause synapse loss in APP Tg mice, as some Tg lines have reduced synaptophysin staining in the dentate gyrus without Aβ deposits (Mucke et al., 2000). Therefore, a possible explanation for the cognitive improvement in the immunized mice in the absence of reduced plaque burden, was a decrease in soluble Aβ, although this potential connection was not measured in their study (Morgan et al., 2000). The results obtained in the laboratory of the present inventors show that following 7 months treatment, the 81-89% reduction in amyloid plaque burden is associated with a 57% reduction in soluble Aβ1-42 within the brain, whereas the reduction in soluble total Aβ and Aβ1-40 was not significantly different from the control group. In other words, soluble Aβ is reduced less than plaque Aβ. However, detailed time course studies must be performed to determine further any changes in the equilibrium between soluble- and plaque Aβ. These findings indirectly demonstrate the importance of Aβ1-42 for plaque maintenance. Overall, it is likely that several different mechanisms may result in reduction of cerebral amyloid burden, depending on the animal model and the properties of the peptide used for immunization.

Numerous studies have suggested that amyloid deposition can activate inflammatory cascades in the brain, such as increased IL-1 production associated with neuronal injury and death (Sigurdsson et al., 1996 and Akiyama et al., 2000). It is possible that our immunization with Aβ homologous peptides could also stimulate such negative inflammatory pathways, along with amyloid reduction. However, few phagocytic microglia were observed in our immunized animals, as identified by OX-42 immunoreactivity or tomato lectin binding. This is not surprising because after 7 months treatment most of the plaques have been cleared. Furthermore, in the immunized group of mice microglial IL-1β staining was virtually absent, whereas numerous ramified IL-1β positive microglia were associated with the plaques in the control Tg group. The laboratory of the present inventors have previously reported a similar lack of IL-1β staining in a rat model of cerebral amyloidosis following treatment with a β-sheet breaker peptide (Sigurdssone et al., 2000). However, in that acute study (16 days) this effect was associated with extensive increase in phagocytic OX-42 staining, indicating that phagocytes do not express IL-1β. The current observations from the experiments in this example may suggest that an important effect of the immunization is reduced inflammation within the brain.

EXAMPLE 2

Materials and Methods

Peptides

The peptides used (Aβ1-40, Aβ1-42, Aβ1-30-NH$_2$, K6Aβ1-30-NH$_2$, Aβ1-30-K6 (SEQ ID NO:11), Aβ1-30-NH$_2$ (EE$_{18,19}$) (SEQ ID NO:12), Aβ1-30-NH$_2$(DD$_{18,19}$) (SEQ ID NO:13) were synthesized at the Keck Foundation (Yale University, New Haven, Conn.), as described previously (Sigurdsson et al., 2000). The Aβ homologous peptides maintain the two major immunogenic sites of Aβ peptides (residues 1-11 and 22-28 of Aβ1-42 based on the antigenic index of Jameson et al. (1998) and on preliminary results obtained in the laboratory of the present inventors), while being non-fibrillar and non-toxic.

Study of Amyloid Fibril Formation in vitro and Neurotoxicity

The experiments were performed as described in Example 1.

Data Analysis: The cell culture data was analyzed by one-way ANOVA, followed by a Newman Keuls' test for post hoc analysis (GraphPad Prism 3.0).

Results

Figure 5:
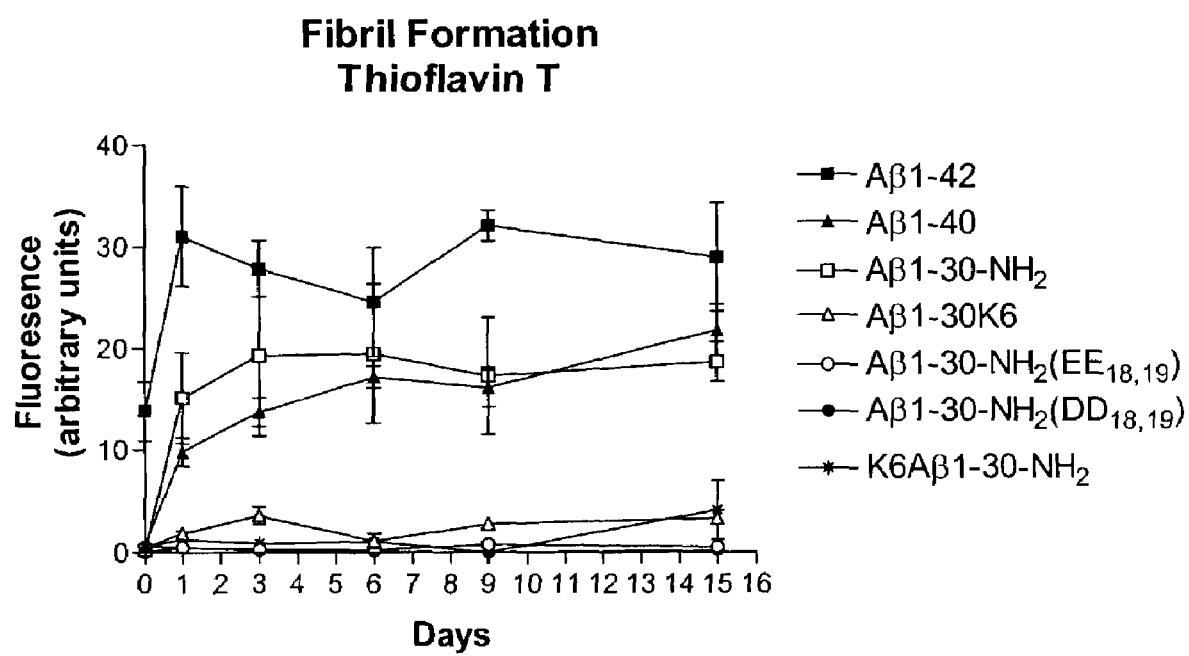
FIG. 5 shows the results of a thioflavin T fluorometric assay. Fibril formation of Aβ1-42, Aβ1-40, Aβ1-30-NH$_2$, Aβ1-30K6, Aβ1-30-NH$_2$(EE$_{18, 19}$) and Aβ1-30-NH$_2$(DDL$_{18,19}$) was measured in vitro following incubation at 37° C. for 15 days. Within this period, no fibril formation of the Aβ derivatives containing a polylysine segment or an amino acid substitution within the hydrophobic region was detected.

Thioflavin T assay: Aβ1-42 was already fibrillar at t=0, whereas Aβ1-30-NH$_2$ and Aβ1-40 gradually formed fibrils over time (FIG. 5). Aβ1-30K6 was slightly fibrillogenic but Aβ1-30-NH$_2$(EE$_{18,19}$) and Aβ1-30-NH$_2$(DD$_{18,19}$) did not form fibrils following incubation at 37° C. for at least 15 days.

Figure 6A:
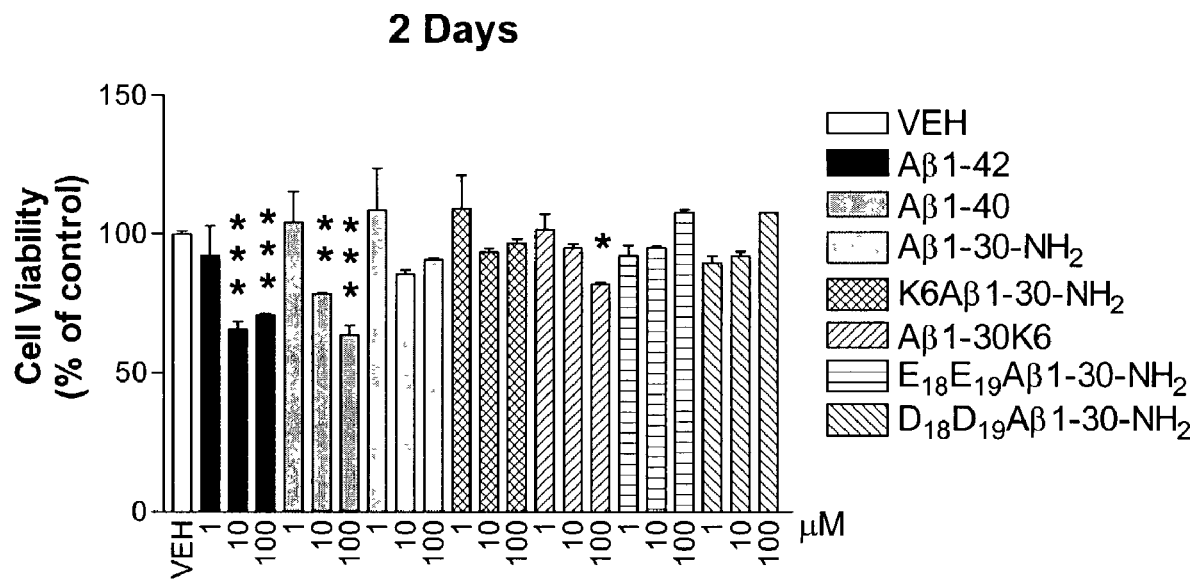
FIGS. 6A and 6B show the results of MTT cell toxicity assay. Neurotoxicity of Aβ1-42, Aβ1-40, Aβ1-30-NH$_2$, K6Aβ1-30-NH$_2$, Aβ1-30K6, Aβ1-30-NH$_2$(EE,$_{18,19}$) and Aβ1-30-NH$_2$(DD,$_{18,19}$) was determined following treatment of human neuroblastoma cells (SK-N-SH) for 2 (FIG. 6A) and 6 (FIG. 6B) days. *p<0.05; p<0.01; *p<0.001 compared to VEH group (one-way ANOVA). In this assay, Aβ1-40 and Aβ1-42 were toxic to human neuroblastoma cells (SK-N-SH) in culture. Of the Aβ derivatives, even at the highest concentration (100 μM), only Aβ1-30K6 displayed a slight toxicity and only on day 2 of the test. Several of the peptides were neurotrophic following 6 days incubation. *p<0.05; p<0.01; *p<0.001 (One-way Anova; Neuman Keuls' posthoc test).
Figure 6B:
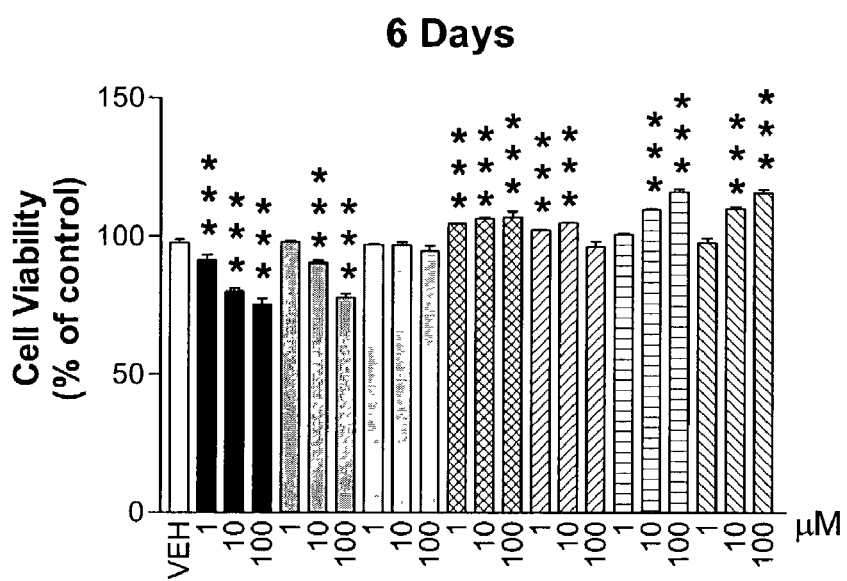

Neurotoxicity: To further assess the safety of this vaccination approach the neurotoxicity of the peptides was determined (FIGS. 6A and 6B). Treatment effect was observed both at 2 and 6 days (p<0.0001). The control peptides Aβ1-40 and Aβ1-42 were toxic (p<0.01-0.001) to the human neuroblastoma cells (SK-N-SH), compared to vehicle group, as determined by the MTT assay. K6Aβ-30-NH$_2$ had no effect on cell viability at 2 days and was slightly trophic at 6 days (p<0.001), and the highest dose (100 gM) of Aβ1-30K6 was slightly toxic following 2 days treatment but not at 6 days. During the incubation period, aggregates were visible under the microscope only in culture wells containing Aβ1-42 (10-100 μM). These Aβ homologous peptides according to the present invention do not form fibrils and are non-toxic in human neuronal culture. Overall, this approach has a much lower risk of leading to toxic effects in humans, than the use of Aβ1-40/42.

EXAMPLE 3

Prion infections do not illicit a classical immune response; however, transport of prions from the periphery to the central nervous system is critically dependent on the lymphoreticular system. In this example, the present inventors sought to determine how active immunity against PrP would influence progression of disease. The experiments described herein show that vaccination with recombinant mouse prion protein (recPrP) delays the onset of prion disease in mice.

Methods

Figure 7:
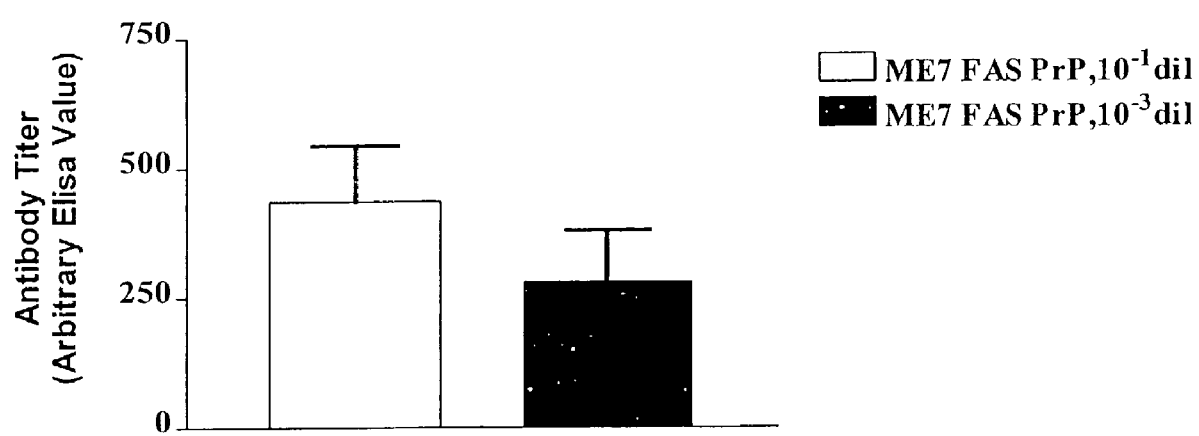
FIG. 7 shows the antibody titer determined by ELISA in mice 14 weeks after vaccination with mouse recPrP.
Figure 8A:
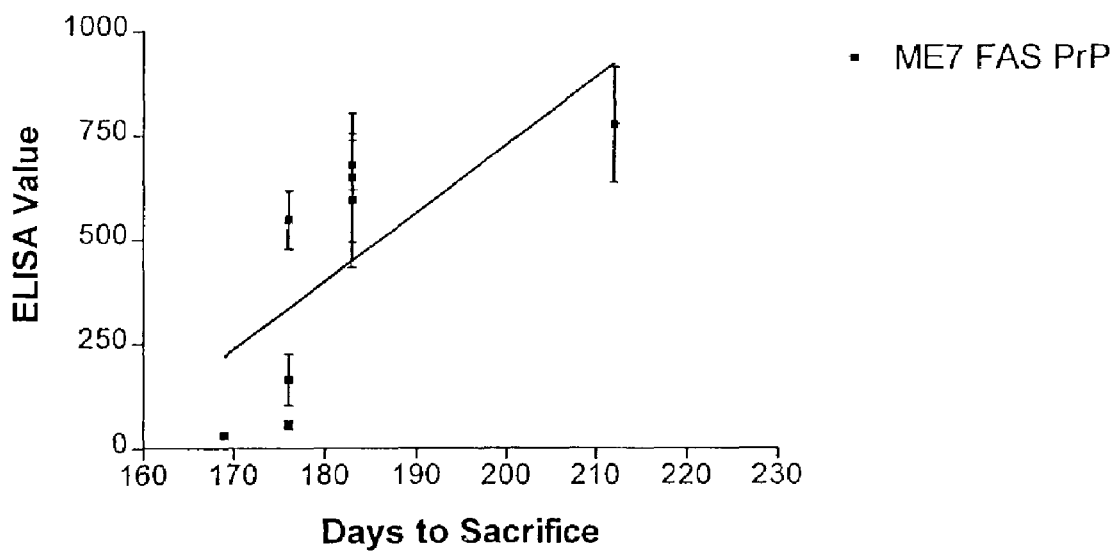
FIGS. 8A and 8B show that a higher anti-PrP$^C$ (ME7 FAS PrP) antibody titer in vaccinated mice, as presented in FIG. 7, correlates with a longer incubation time in both PrP$^{Sc}$ inoculated mouse groups at lower dilution (FIG. 8A; r$^2$=0.4389, p=0.0052) and at higher dilution (FIG. 8B; r$^2$=0.6786, p<0.0001).
Figure 8B:
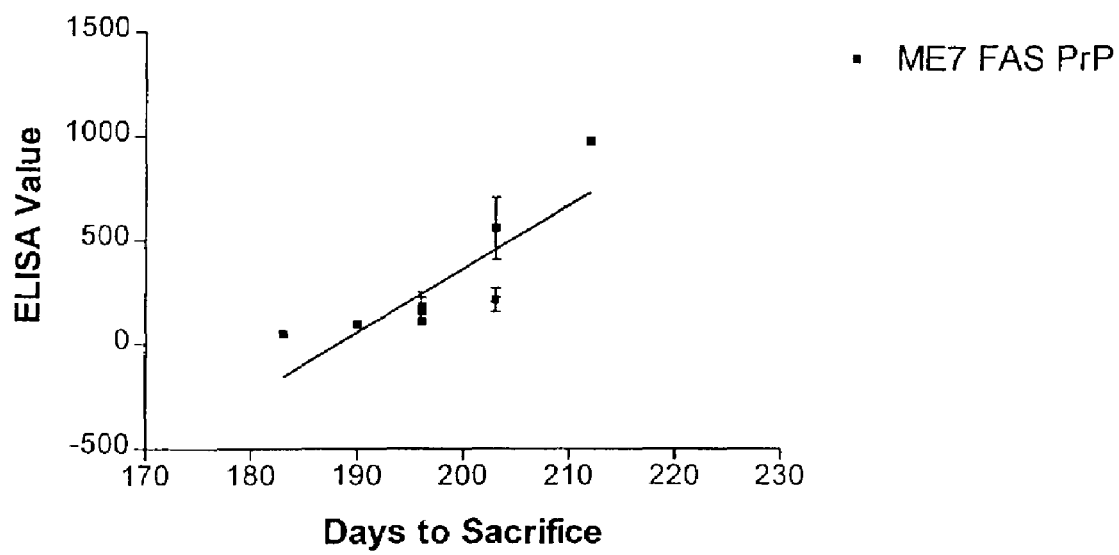

Twenty female CD-1 mice, 2-3 months of age, were immunized with mouse recPrP. For the first injection, the recPrP (Brown et al., 1999) (1 mg/ml in 0.5 M urea) was mixed with an equal volume of complete Freund's adjuvant immediately before subcutaneous administration (50 μg recPrP/100 μl). Twenty control mice received the adjuvant plus vehicle. Subsequent immunizations were performed at 2 weeks intervals in incomplete Freund's adjuvant. Fourteen weeks following the first vaccination the mice were bled and the PrP antibody titer was determined by ELISA (FIG. 7). The mice were subsequently divided into two groups matched for their titer to recPrP and were inoculated intraperitoneally with a brain homogenate of the mouse-adapted scrapie strain 139A at a 10-fold (FIG. 8A) and a 1000-fold (FIG. 8B) dilution. The control mice were also divided into two groups that received either the 10-or 1000-fold dilution of same 139A inoculum. The immunization was continued thereafter at monthly intervals until the first mice showed clinical symptoms of scrapie. The mice were sacrificed when they scored positive by observers blinded to the experimental status of the animals for three consecutive weeks (Soto et al., 2000). The diagnosis of prion disease was confirmed by staining brain sections with a polyclonal anti-PrP antibody (anti-PrP 78295) and by the detection of proteinase K resistant PrP on Western blots (Kascsak et al., 1997).

Results

Figure 9:
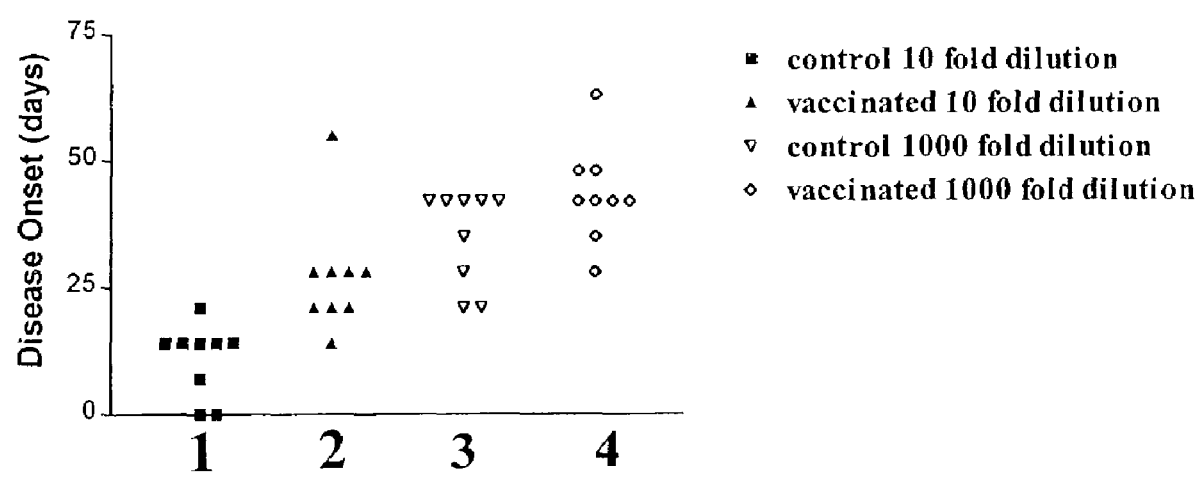
FIG. 9 is a graph showing the effect of recPrP vaccination on disease onset, with day 0 being the first day an animal scored positive for disease. Group 1 mice were controls inoculated with PrP$^{Sc}$ at a 10 fold dilution, while group 2 was inoculated at the same dilution but also received recPrP vaccination. Group 3 mice were controls inoculated with PrP$^{Sc}$ at a 1000 fold dilution, while Group 4 received the same dilution of PrP$^{Sc}$ along with recPrP vaccination. The two control groups received adjuvant and vehicle injections. Two way ANOVA shows a significant effect for vaccination (p=0.0005) and PrP$^{Sc}$ dilution (p<0.000001). The Newman-Keuls post-hoc test showed vaccination to have a stronger effect in the 10 fold dilution group (Group 1 versus 2, p=0.001 two-tailed; Group 3 versus 4, p=0.036 one-tailed).

As depicted in FIG. 9, the mice immunized with the recPrP had a delayed onset of scrapie symptoms (two-way ANOVA, p=0.0005 for vaccination effect). The Newman-Keuls post hoc test revealed a more pronounced effect at the 10 fold dilution (p=0.001, two-tailed). This is most likely related to a significantly higher average titer of anti-PrP antibodies at the time of sacrifice in the group receiving a lower dilution of PrP$^{Sc}$ (p<0.05). A higher anti-PrP$^C$ antibody titer, in vaccinated animals, correlated with a longer incubation time in both the PrP$^{Sc}$ inoculated mouse groups (lower dilution group: r$^2$=0.4389, p=0.0052; higher dilution group: r$^2$=0.6786, p<0.0001).

While not being limited to any particular theory, it is possible that antibody binding to PrP$^C$ and/or PrP$^{Sc}$ may interfere with PrP$^{Sc}$ mediated conversion of PrP$^C$ to PrP$^{Sc}$ and thereby delay the onset of clinical symptoms. Recent in vitro studies support this view (Enari et al., 2001; Peretz et al., 2001).

Furthermore, overexpression of recPrP in E. coli leads to the formation of inclusion bodies that stain positive for Congo red, indicating a potential toxic property. This toxic property would not be exhibited by a PrP peptide substituted according to the invention.

EXAMPLE 4

This example describes the application of recPrP as a rescue treatment, i.e., administration of recPrP after exposure to scrapie. See, also, Sigurdsson et al. (Am J Pathol 2002).

Methods

The experiment was performed similarly to the prophylactic treatment mouse group described in Example 3, except for immunization with recPrP being started 24 hours after intraperitoneal inoculation with mouse-adapted scrapie strain 139A. As before, there were two groups of 10 female CD-1 mice each at 2 to 3 months of age, which received either a 10-fold or 1000-fold dilution of the 139A brain homogenate inoculum intraperitoneally, followed in this case by the first recPrP injection in complete Freund's adjuvant 24 hours later. There were also two control groups of 10 CD-1 mice, which received either the 10-fold or 1000-fold dilution of the same 139A brain homogenate inoculum intraperitoneally, but followed by injection of adjuvant plus vehicle (0.5 mol/L urea). The rest of the protocol was identical to the prophylactic treatment mouse group in the 10-fold PrP$^{Sc}$ dilution group (see above)

Results

Figure 2B:

As expected, the effects of the treatment were somewhat less pronounced in the rescue mouse group, compared to the prophylactically treated mice (see, FIG. 2A in Sigurdsson et al., Am J Pathol 2002). No significant group difference was observed in disease onset in mice receiving the 10-fold dilution of the brain inoculum (days to sacrifice, 192±5 days (control) versus 190±5 days), although the levels of antibodies against PrP$^C$ correlated with disease onset ($r^2$=0.279, P<0.017). However, at the 1000-fold dilution, a delay in symptoms was observed in the vaccinated mice (days to sacrifice, 210±3 days (control) versus 222±4 days; P<0.018, t-test, one-tailed). As with the prophylactic treatment, the anti-PrP C antibody levels in the immunized mice correlated with a longer incubation time (see, FIG. 2B in Sigurdsson et al. (Am J Pathol 2002); $r^2$=0.772, P<0.0001). Histological and Western blot evaluations of all of the brains of the treated and control groups did not reveal any apparent differences in the degree of spongiform change or PrP$^{Sc}$ levels at the time of sacrifice in either the prophylactic or rescue treatment mouse experiments. Hence, immunization delayed PrP$^{Sc}$ propagation, but ultimately similar pathology and levels of PrP$^{Sc}$ were obtained in treatment and control groups.

EXAMPLE 5

This example describes the application of anti-PrP antibodies for prophylaxis following prion exposure in a mouse model.

One hundred female CD-1 mice, 2 months of age, were inoculated intraperitoneally (i.p.) with a brain homogenate of the mouse-adapted scrapie strain 139A at a 10-fold or a 1000-fold dilution. This represents a well established model of prion disease in mice, which leads to CNS scrapie infection and death in all cases, if the disease is allowed to progress (Sigurdsson et al., Am J Pathol 2002; Soto et al., 2000).

Immediately following inoculation, the mice received i.p. injection (50 μg/500 μl phosphate buffered saline) of monoclonal anti-PrP antibodies (8F9, 8B4 or 8H4; ten mice per group at each dilution of scrapie) (Liu et al., 2001). Twenty mice received pooled mouse IgG (Sigma, St. Louis, Mo.) and a further 20 received no injections. Subsequent passive immunizations were continued on a weekly basis until the week of sacrifice, which occurred when the mice scored positive for three consecutive weeks on a behavioral test for prion disease. The symptoms of scrapie were determined by a test of motor coordination, performed by observers blinded to the experimental status of the animals, using an established protocol (Sigurdsson et al., Am J Pathol 2002; Soto et al., 2000). The diagnosis of prion disease was confirmed by staining brain sections with cresyl violet, immunostaining with a polyclonal anti-PrP antibody (anti-PrP 78295) and by the detection of proteinase K resistant PrP from brain and spleen on Western blots as previously described (Sigurdsson et al., Am J Pathol 2002; Soto et al., 2000).

The epitopes of the antibodies are as follows: 8B4 (residues 34-52), 8H4 (175-185) and 8F9(205-233) (Liu et al., (2001)). The affinity of the antibodies was determined by ELISA against mouse recombinant PrP, mouse PrP$^C$ and mouse PrP$^{Sc}$. The PrP$^{Sc}$ was prepared from ME7 infected mouse brains using an established protocol (Diedrich et al., (1991)). The PrP$^C$ was prepared by treating the purified PrP$^{Sc}$ with formic acid so that it reverted to proteinase K digestion sensitivity (Kascak et al., (1997)). Under these ELISA conditions, the KD of binding of 8F9 was lower compared to 8H4 or 8B4 (2.10 versus 0.04 and 0.05 nM, respectively for PrP$^{Sc}$; 43 versus 0.09 and 6.5 nM for PrP$^C$, respectively; 0.7 versus 0.07 and 0.08 nM, respectively for recPrP). The duration the anti-PrP antibodies were present in the serum following i.p. injection was assessed by bleeding the mice and testing the serum by ELISA for reactivity against recombinant PrP. Ten minutes following i.p. injection of the monoclonal antibody, its concentration in the serum was 20 μg/ml (±4 μg/ml); 4 h following i.p. injection the antibodies were no longer detectable in the serum by ELISA.

Two-way analysis of variance revealed a significant treatment-(P<0.0001) and dilution effect (P<0.000001). The 8B4 and 8H4 antibodies were more effective than the 8F9 antibody; this is probably related to the higher affinities of these antibodies to PrP$^C$ and PrP$^{Sc}$. Within the 10-fold PrPSc dilution group, Newman-Keuls post hoc analysis showed that the incubation times for both the non-injected and the IgG control groups was significantly different from the 8B4 (P<0.05) and the 8H4 group (P<0.05). Within the 1000-fold PrP$^{Sc}$ dilution group, the IgG and non-injected control groups significantly differed from the 8B4 group (P<0.001 and P<0.05, respectively, one-tailed). Ten percent of the 8B4-injected animals did not develop disease. As anticipated, no apparent differences were observed in the animals that became ill, between the treatment and control groups in terms of the scrapie associated pathology and the PrP$^{Sc}$ levels as they were sacrificed at equivalent time points after becoming clinically ill.

These findings demonstrate the therapeutic effect of anti-prion antibodies for post-exposure prophylaxis for prion infection.

EXAMPLE 6

This example describes vaccination of Tg2576 APP mice (see Example 1) with K6Aβ1-30-NH2 and Aβ1-42 using aluminum adjuvants, and behavioral analysis of vaccinated animals.

Testing of Aluminum Adjuvants

In general, the type of aluminum adjuvant chosen is the one that allows the greatest adsorption of the antigen onto the adjuvant. The pI (isoelectric point) for Aβ1-42 is 5.42 and the peptide has a negative charge at physiological pH, whereas the pI for K6Aβ1-30-NH2 is 9.9 and the peptide has a positive charge at physiological pH. Alhydrogel® (Superfos Biosector, Denmark) has a positive charge under biological conditions and was therefore selected for testing with Aβ1-42. Adju-Phos® (Superfos Biosector) has a negative charge under the same conditions, and was therefore selected for K6Aβ1-30-NH2.

Briefly, 30 μl of Alhydrogel® or Adju-Phos® were added to 30 μg of peptide, the mixture was vortexed and then rotated overnight at 4° C. Following centrifugation, the peptide concentration in the supernatant was determined by a Comassie Plus® (Pierce) protein assay according to the manfacturer's instructions. Table 2 shows the adsorption of peptides onto the adjuvants, verifying that Alhydrogel® and Adju-Phos® successfully adsorb Aβ1-42 and K6Aβ1-30-NH2, respectively.

TABLE 2

|  | Adsorbed K6Aβ1-30-NH$_2$ | Adsorbed Aβ1-42 |
|---|---|---|
| Alhydrogel ® | 82.7% | 98.1% |
| Adju-Phos ® | 97.5% | Not-tested |

Animal Vaccination

Tg2576 mice, 3.5 to 4 months old, were injected subcutaneously with either 100 μg K6Aβ1-30-NH2 in 100 βl Adju- Phos® ("tg-k6" group); 100 μg Aβ1-42 in 100 μl Alhydrogel® ("tg-ab42" group); or Adju-Phos® or Alhydrogel® alone (100 μl, "tg-ah" or "tg-ap" group, respectively). Non-transgenic littermate mice injected with 100 μg K6Aβ1-30-NH2 in 100 μl Adju-Phos® were used as a control ("ntg-k6" group). All animals received the first 5 injections at 2-week intervals, with monthly injections thereafter.

Antibody Titers

Figure 11A:
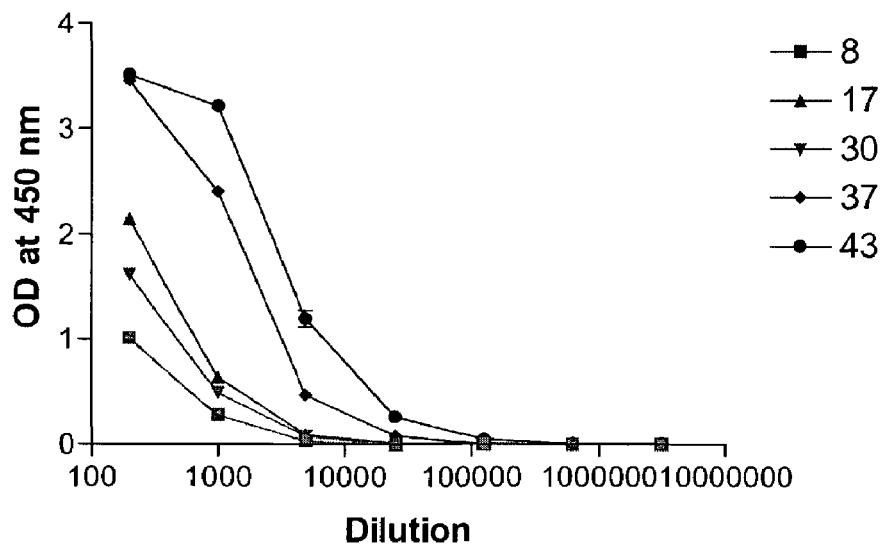
FIGS. 11A-C show ELISA evaluation of sera from individual animals vaccinated with K6Aβ1-30-NH2 and alum adjuvant, testing for antibody titer against antigen (FIG. 11A), Aβ1-42 (FIG. 11B) and Aβ1-40 (FIG. 11C).
Figure 11B:
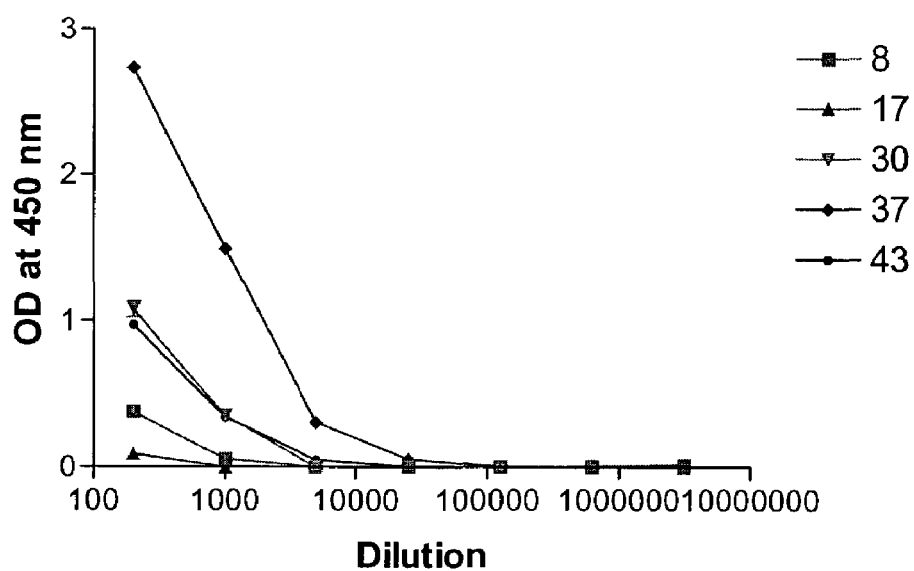
Figure 11C:
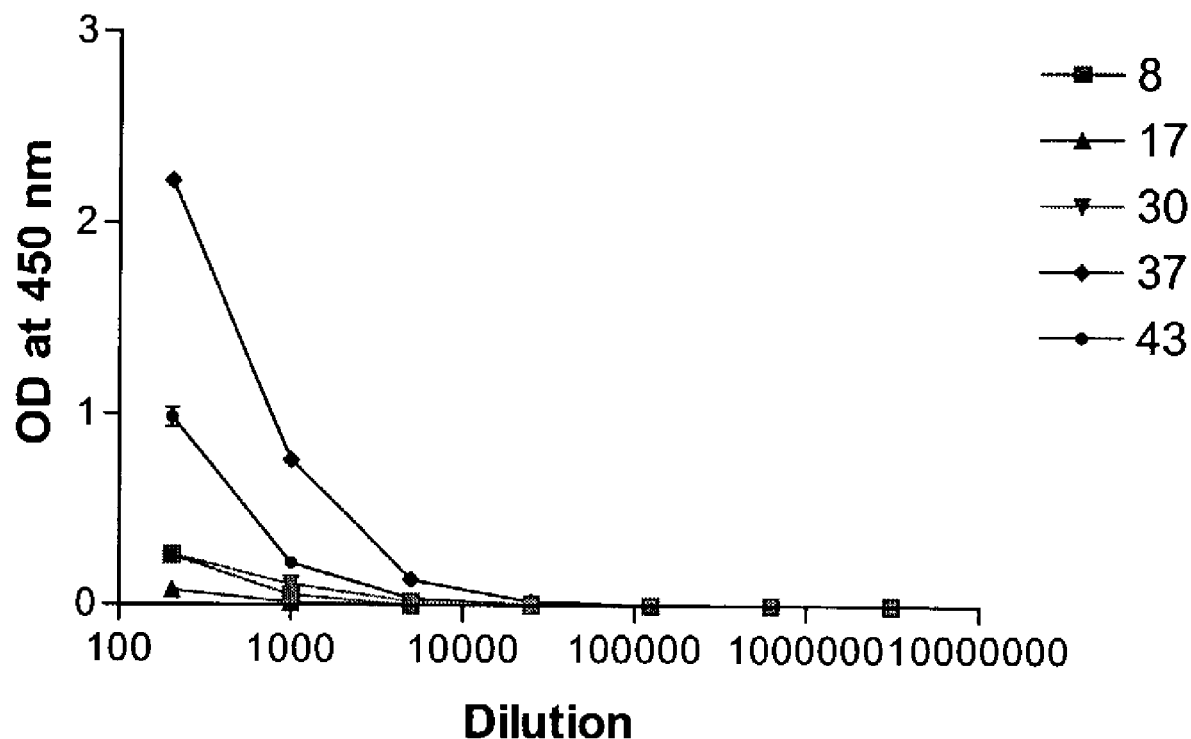
Figure 12A:
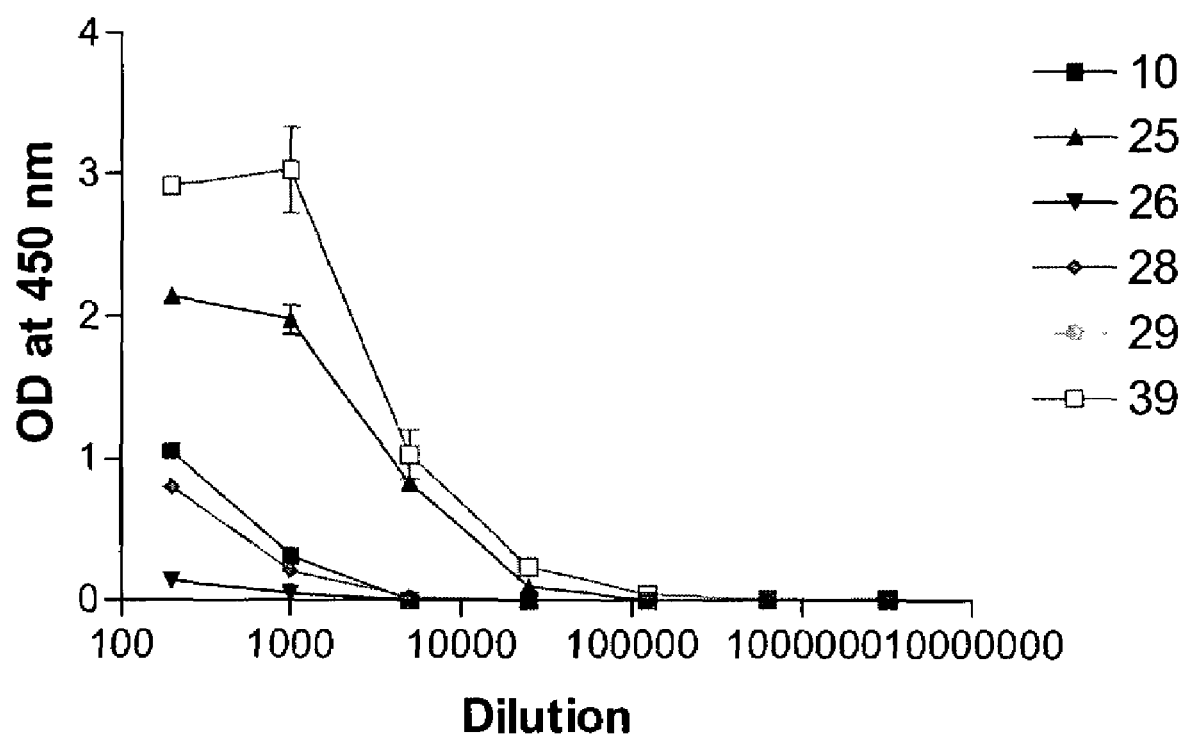
FIGS. 12A-C show ELISA evaluation of sera from individual animals immunized with Aβ1-42 and alum adjuvant, testing for antibody titer against antigen (FIG. 12A), K6Aβ1-30-NH2 (FIG. 12B) and Aβ1-40 (FIG. 12C).
Figure 12B:
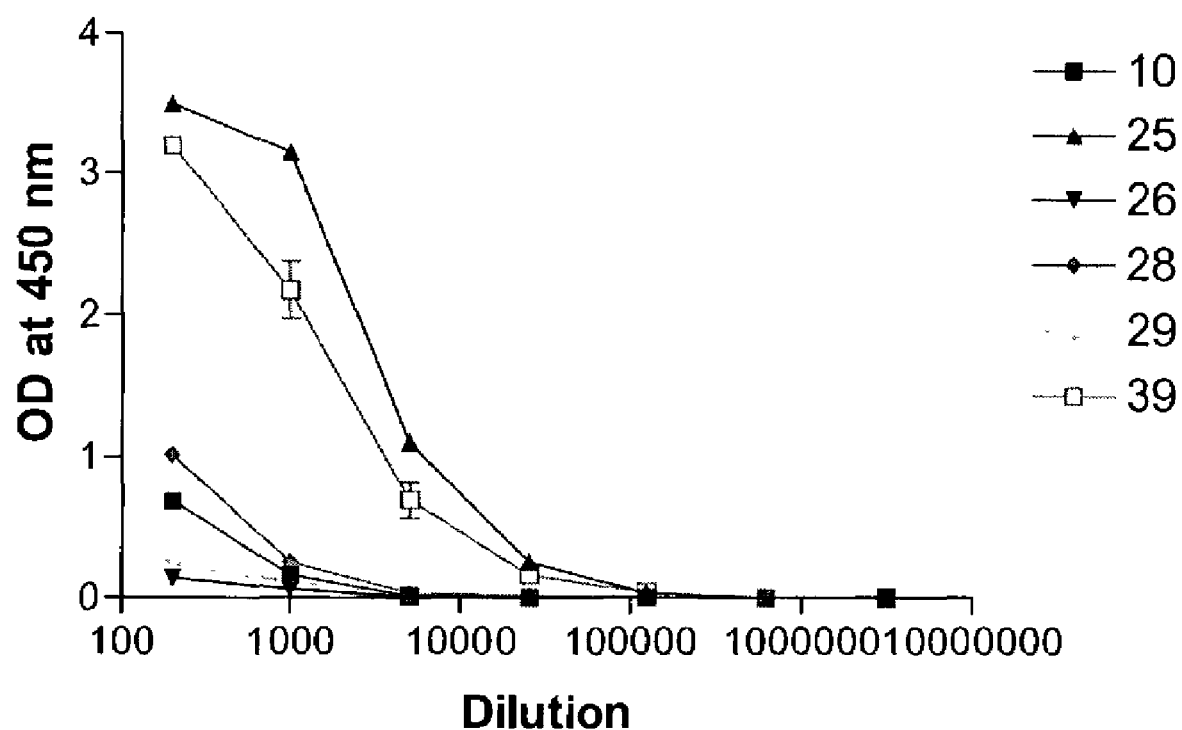
Figure 12C:
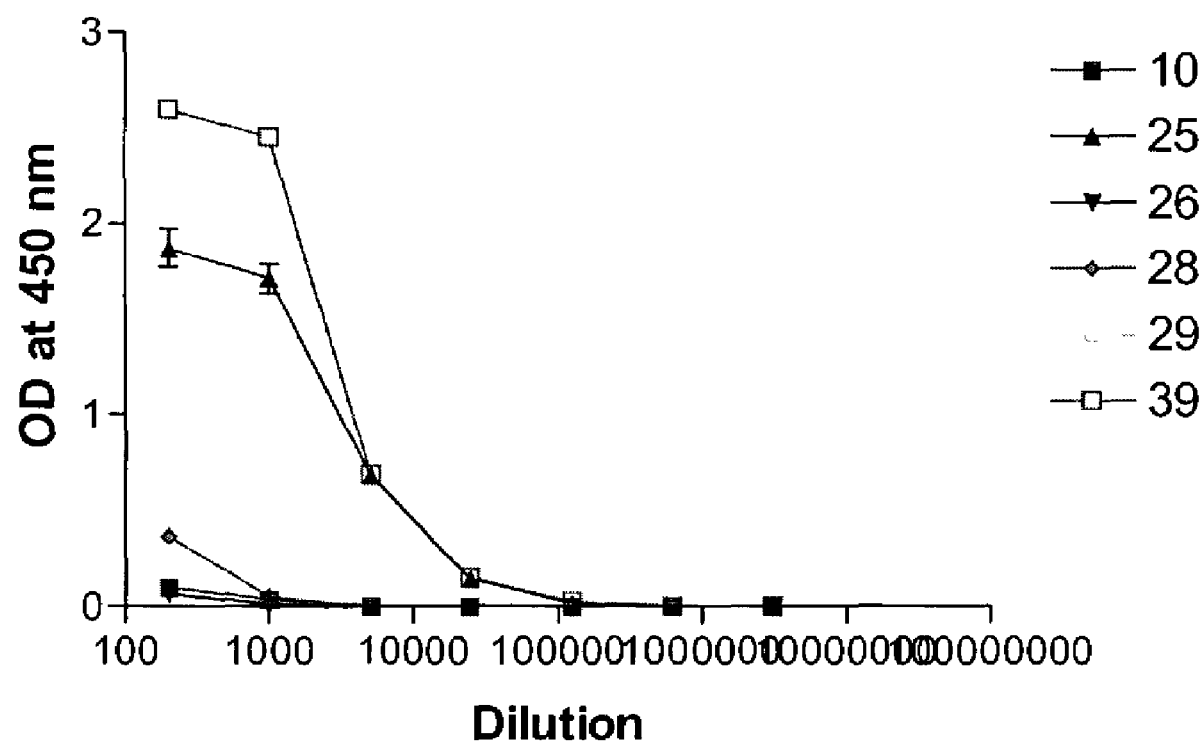

The first group of mice were bled two weeks after the 5$^{th}$ injection, and the antibody titer to K6Aβ1-30, Aβ1-42, and Aβ1-40 determined by ELISA (see Example 1 for assay description). A sample of the results are visualized in FIG. 11. FIG. 11A-C shows that sera from animals vaccinated with K6Aβ1-30-NH2 contain antibodies which bind to antigen (FIG. 11A), as well as crossreacting antibodies binding to Aβ1-42 (FIG. 11B) and Aβ1-40 (FIG. 11C). The titers in mice injected with K6Aβ1-30-NH2 were reasonably high and in a similar range as in mice injected with the same peptide together with Freund's adjuvant (see Example 1). FIG. 12 shows that sera from animals immunized with Aβ1-42 contain antibodies which bind to antigen (FIG. 12A), as well as crossreacting antibodies binding to K6Aβ1-30-NH2 (FIG. 12B) and Aβ1-40 (FIG. 12C). In general, the mice injected with Aβ1-42 had similar titers as the mice injected with the Aβ derivative. Table 3 shows titer data (EC50 values) for individual mice (one per row) in this group.

TABLE 3

| Group | Aβ1-40 Titer | Aβ1-42 Titer | K6Aβ1-30 Titer |
|---|---|---|---|
| ntg-k6 | 9949 | 9951 | 7356 |
| ntg-k6 | 74 | 86 | 120 |
| ntg-k6 | 2 | 121 | 91 |
| ntg-k6 | 5480 | 4333 | 5839 |
| ntg-k6 | 124 | 35 | 166 |
| ntg-k6 | 166 | 223 | ND |
| ntg-k6 | 65 | 41 | ND |
| tg-k6 | 14 | 1 | 104 |
| tg-k6 | 2 | 1 | 131 |
| tg-k6 | 327 | 171 | 146 |
| tg-k6 | 215 | 694 | 1174 |
| tg-k6 | 33 | 228 | 2816 |
| tg-ab42 | 237 | 128 | 52 |
| tg-ab42 | 3033 | 3187 | 2614 |
| tg-ab42 | 6 | 275 | 443 |
| tg-ab42 | 0 | 80 | 68 |
| tg-ab42 | 38 | 130 | 562 |
| tg-ab42 | 2427 | 3240 | 1341 |
| tg-ah | 208 | 289 | 508 |
| tg-ap | 283 | 587 | 395 |
| tg-ah | 89 | 76 | 80 |
| tg-ah | 103 | 102 | 351 |
| tg-ap | 388 | 671 | 528 |

ND = Not Done

A second group of animals was bled 2 weeks after the 5$^{th}$ injection and 28 weeks after the 5$^{th}$ injection (i.e., about four months after the first blood samples). Table 4 shows titer data (EC50 values) for individual mice in this group.

TABLE 4

| Group | Aβ1-40 Titer | | Aβ1-42 Titer | | K6Aβ1-30 Titer | |
|---|---|---|---|---|---|---|
|  | 2w | 28w | 2w | 28w | 2w | 28w |
| tg-k6 | 171 | 1 | 401 | ND | 732 | ND |
| tg-k6 | 1 | 2 | 8 | 1 | 324 | 2118 |
| tg-k6 | 112 | 431 | 113 | 1 | 279 | 1387 |
| tg-k6 | 302 | 48 | 237 | 78 | 159 | 30 |
| tg-k6 | 6 | 162 | 145 | 151 | 151 | 1378 |
| tg-k6 | 121 | ND | 347 | ND | 730 | ND |
| tg-k6 | 9 | 632 | 87 | 1398 | 180 | 4341 |
| tg-k6 | 17 | 1 | 1 | 104 | 48 | 90 |
| tg-k6 | 0 | 11 | 0 | 61 | 3 | 117 |
| tg-ah | 1 | 1 | 0 | ND | 1122 | 10 |
| tg-ah | ND | 7 | ND | 3 | ND | 148 |
| tg-ah | 977 | 3 | 9 | 1 | 1473 | 1227 |
| tg-ah | 7 | ND | 270 | 1 | 841 | 150 |
| tg-ah | 1 | ND | 2 | ND | 2 | ND |
| tg-ah | 5 | 8 | 1 | 1 | 3 | 271 |
| tg-ah | 4 | 1 | 0 | 139 | 1 | 209 |
| tg-ah | 1 | 1158 | 4 | 130 | 1 | 464 |
| tg-ap | ND | 3 | ND | 1 | ND | 3 |
| tg-ap | 0 | 4 | 0 | 3 | 4 | 4 |
| tg-ap | 4 | 3 | 1 | 252 | 2 | 505 |
| tg-k6 | 0 | 3 | 0 | 3 | 205 | 1564 |

ND = Not Done

In these experiments, it was found that non-transgenic mice had higher titer against the antigen than transgenic mice. This was expected because the antigen contains the human sequence of Aβ which is foreign to the non-transgenic mice. It was also expected that the mice generally had higher titer against the antigen compared to related peptides. Moreover, analysis of the distribution of titer levels showed that about ⅓ of the mice had high titers, ⅓ had medium titers and ⅓ had low titers. This is similar to what has been observed in rabbits used for polyclonal antibody production.

Determination of the amyloid burden in these animals and correlation between amyloid burden and titers will show the level of titer necessary to result in amyloid clearance.

Behavioral Studies—Methods

The following behavioral tests were performed when the animals were 3-4 months and 11 months of age. For statistical analysis of the results, ANOVA followed by Newman-Keuls post hoc test was applied.

Motor Coordination Tests

Locomotor Activity. After 15 minutes of room adaptation, animals were put into closed activity box for 5 minutes. Main room light was turned on throughout the adaptation and the test. The box consists of photoreceptors and whenever an animal crosses the receptor, an activity count is recorded. The activity box records activity counts per minute.

Traverse Beam. After 15 minutes room adaptation, with the big room light on, all animals were given 1 unscored training trial (animals were put into closed goal box for 1 minute and put on the opposite end of the beam thereafter, facing the cardboard wall). Training trial ended when the animal entered the goal box. To prevent injury from falling, a soft yellow colored cover was put underneath the beam. Animals that fell off were placed back into the position they maintained prior to the fall. After training, each animal was tested twice. Errors were defined as footslips and recorded both numerically and using Feeney scores.

Rotarod. Following 15 min room adaptation (lights on), the animal was placed onto the rod (diameter 3.6 cm) for 30 seconds. With each 30-sec interval, the rotation speed was increased by ¼ grade on the machine's scale. Total time (including the 30-sec on the quiescent rod) and RPM when the animal fell down were recorded. The rod was cleaned with a dry cloth before each animal started its trial. A soft yellow cover was placed beneath the apparatus to prevent potential injury from falling. Each animal was tested thrice with an intertrial interval of fifteen minutes.

Cognitive Tests

Animals were randomly split into three equivalent groups and then run on each test such that all three groups received each test in a different sequential order.

Radial Arm Maze. Animals were kept in the test room throughout the experiment, behind a cover to prevent view of the apparatus and room. Each animal underwent 2 days of adaptation, consisting of 15 minutes exploration in the maze (2 subjects at a time), with 3 pieces of fruit loops in each arm. Subjects were exposed to doors only on day 2. Animals, having approximately ten percent body weight loss, were food deprived 1 day before adaptation session I. Fruit loops were added to normal diet 5 days before deprivation schedule started. Animals entered and exited the maze through the center. Testing included recording correct and incorrect arms entered. Animals were placed in the center of the maze and all doors were opened. After entry into an arm, the animal had to find and eat the reinforcer before the door was opened for the animal to re-enter the center of the maze. Testing ended when all eight arms had been entered and reinforecers found. Re-entry into an arm constituted an error. Total number of errors and time to enter all eight arms were recorded. Access to food was given for 3-4 hours (depending on age, body weight loss) daily, and the apparatus was cleaned with 95% ethanol after each animal. Arms were cleaned with dry cloth after each cage.

Morris Water Maze. Apparatus: A round, white plastic pool (d=75 cm, h=14.5 cm) was filled with water 5 cm below the top edge. The water was rendered opaque adding 120 ml of white finger paint (Rich Art, Northvale, N.J.). Water was kept at 30 degree Celsius.

For straight alley swimming, animals were placed into one end of a straight alley constructed from wood and had to find the hidden platform placed at the other end. After finding the platform the animals were allowed to sit there for 15 s. There was an inter-trial interval of 7 to 8 minutes upon which the animal was given the subsequent trial. This was repeated for 6 trials. Animals were removed from the platform using a wooden plank to avoid handling and extraneous stress.

For visual platform testing, on the second day, animals had to locate a visible platform (salient cue on top, platform 0.5 cm above water line). The location of each platform was varied five times. Animals were started at random points in the maze (maximum latency 60 s). If the animal could not find the platform within 60 seconds, it was gently led to it. After locating the platform, the animal was allowed to remain on the platform for 15 seconds. Furthermore, the pool was shunted in order to avoid any extra-maze cues.

For acquisition in invisible platform testing, animals had to locate the invisible platform (1.0 cm below waterline). Three daily trials (different start positions) were administered for a total of six days. Each animal received three trials with an inter-trial interval of 7 to 8 minutes. If the animal could not locate the platform within sixty seconds, it was led to it and allowed to remain there for 15 seconds. After each trial, the animal was placed under a heating lamp until the next trial.

Finally, a probe trial procedure was carried out in order to assess retention of the location of the platform. Animal was placed into the center of the pool (no platform) and allowed to swim for 60 s. % distance scores for each quadrant were obtained and compared across groups.

Figure 13:
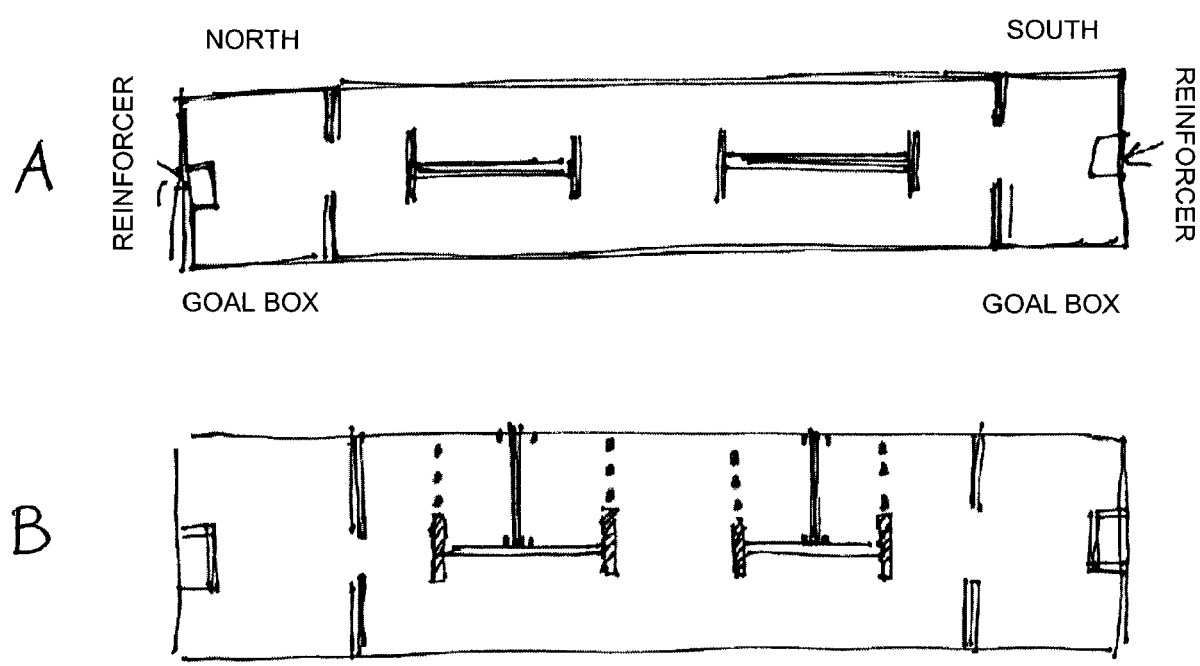
FIGS. 13A and 13B depict a linear maze used to evaluate cognitive capabilities of animals vaccinated with Aβ1-30-NH$_2$ and K6Aβ1-30-NH$_2$ together with alum adjuvants, as well as controls.

Linear maze. An outline of the maze is shown in FIG. 13. Briefly, in the maze of FIG. 13, during adaptation, the alleys are unblocked, and the animal must run from north goal box to south and back and learn to drink the reinforcer; sucrose solution. During testing, the west alleys are blocked, and the animal must learn to use the east alleys. Error zones are dotted. Testing begins in the south goal box, and the animal must go to the north goal box (returning to the goal box of origin is also an error). Time and error is recorded. The criterion is shuttling with zero errors in 4 out of 5 trials. For reversal, after having reached the criterion, the alleys that are blocked are reversed (i.e., animals having learned the east route must now learn the west route).

Animals were water deprived throughout the experiment and kept at a body weight loss of 12±2% (=40 min/day access to $H_2O$). A 4% sucrose solution (dissolved in regular tap $H_2O$ and dyed with non-toxic food coloring to increase contrast) was used as a reinforcer (made freshly 1/week). Floor and walls of the maze were cleaned using 50% ethanol before each trial. Valves were rinsed with 12 cc 95% ethanol, followed by 48° C. distilled $H_2O$ whenever the reinforcer was changed.

For step 1, adaptation, following 24 hours of water deprivation, animals were individually adapted to the maze for 8 min and trained to shuttle between the goal boxes. Animals were placed in the goal box and allowed time to explore the maze. None of the alleys were blocked. Adaptation procedure was repeated for two days to ensure that animals shuttled from the north end to south end as well as drank the sucrose solution.

For step 2, acquisition, alleys located on the same side of the maze (E or W) were randomly blocked for each animal during acquisition. Mice were given a maximum of daily 20 trials until they reached a criterion of 4/5 errorless trials. An error was recorded when the animal looked into a blocked alley or changed direction. Maximum interval/session: 20 min.

For step 3, reversal, when an animal reached criterion (4/5 errorless), the session was finished. The next day, for animals who successfully had reached criterion, the blocked alleys were reversed (i.e., from E to W or vice versa). The reversal procedure was repeated twice, so that in total each animal had 1 acquisition and 2 reversals scores.

Behavioral Studies—Results

Figure 14A:
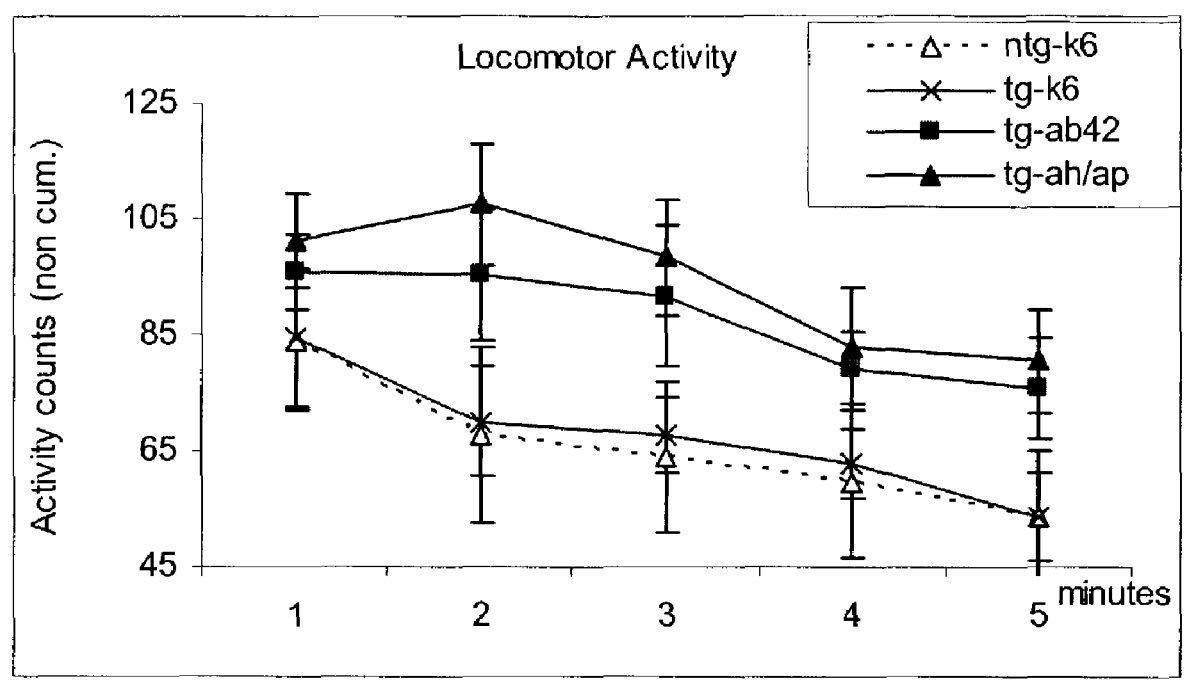
FIGS. 14A-C depict results obtained from behavioral studies of animals of about 3-4 months of age, after vaccination with Aβ1-30-NH$_2$ and K6Aβ1-30-NH$_2$ together with alum adjuvants, as well as controls. The studies included testing of locomotor activity (FIG. 14A), spontaneous avoidance (FIG. 14B), and passive avoidance (FIG. 14C). See Example 6.
Figure 14B:
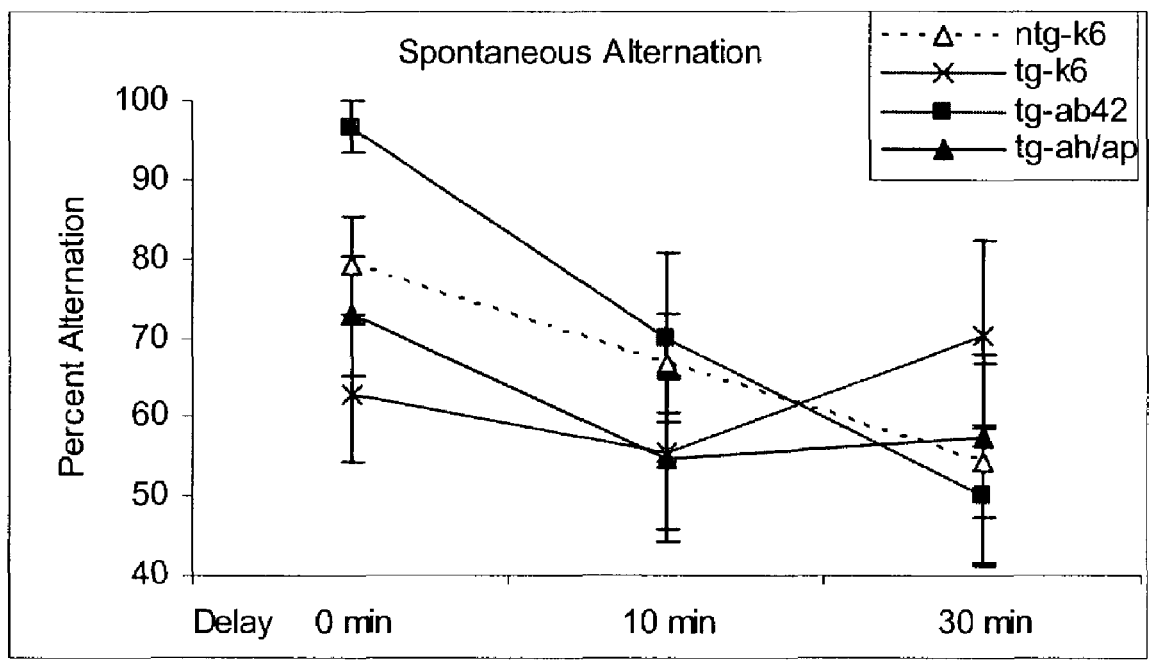
Figure 14C:
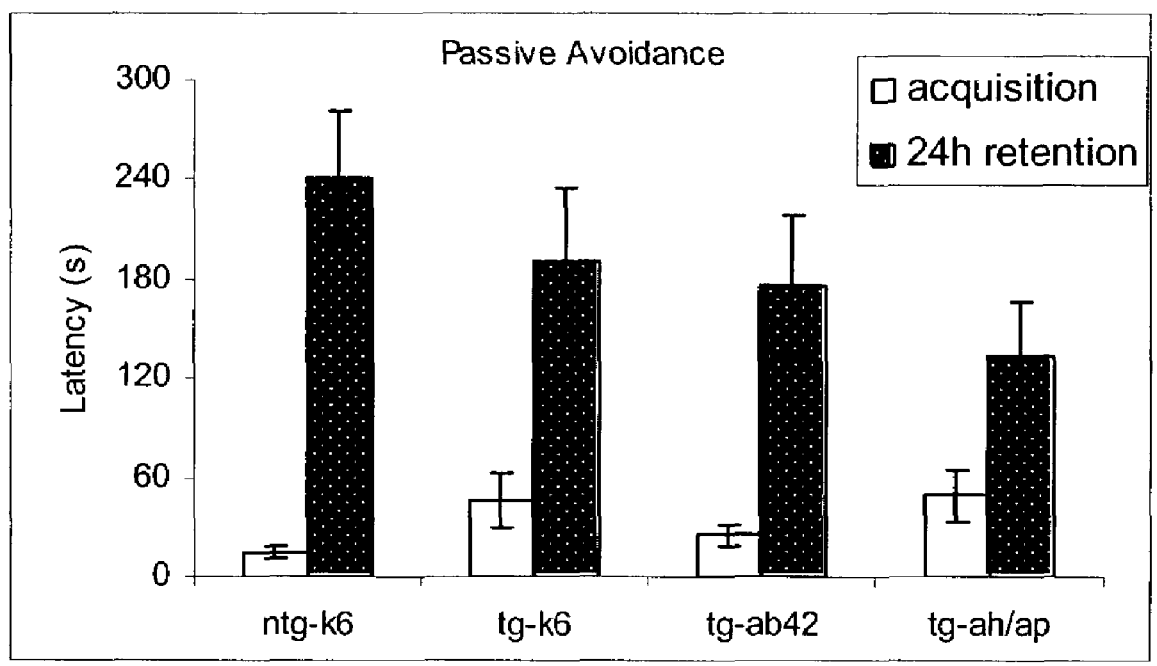

FIGS. 14A, 14B, and 14C show the results obtained in the respective groups when the animals were about 3-4 months of age. The figures show the results from locomotor activity, spontaneous avoidance, and passive avoidance, FIGS. 14A-C, respectively. Significant differences were observed between the groups in locomotor activity (Two-way ANOVA: treatment; p=0.046, time; p<0.0001). Neuman Keuls post hoc analysis revealed significant differences between tg-ah/ap vs. nontg-k6 (p=0.022) and tg-k6 (p=0.027). These results suggest that K6Aβ1-30-NH2 has an acute effect, reducing the locomotor activity of tg mice to that of their non-tg littermates.

Figure 15A:
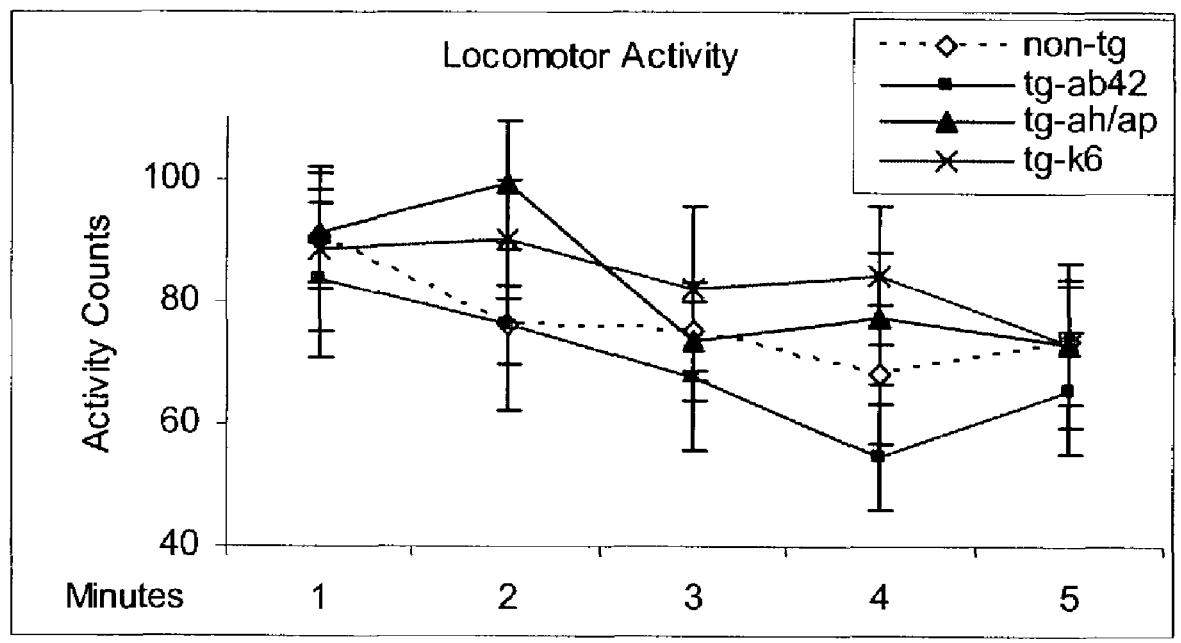
FIGS. 15A-N depict results obtained from behavioral studies of animals of about 11 months of age, after vaccination with Aβ1-30-NH$_2$ and K6Aβ1-30-NH$_2$ together with alum adjuvants, as well as controls. The studies included testing of locomotor activity (FIG. 15A), and cognitive testing using traverse beam (FIGS. 15B and 15C), rotarod (FIG. 15D), radial arm maze (FIGS. 15E and 15F), straight alley channel (FIG. 15G), visible platform (FIGS. 15H and 15I), Morris water maze (FIGS. 15J and 15K), probe trial (FIGS. 15L and 15M), and linear maze (FIG. 15N). See Example 6.
Figure 15B:
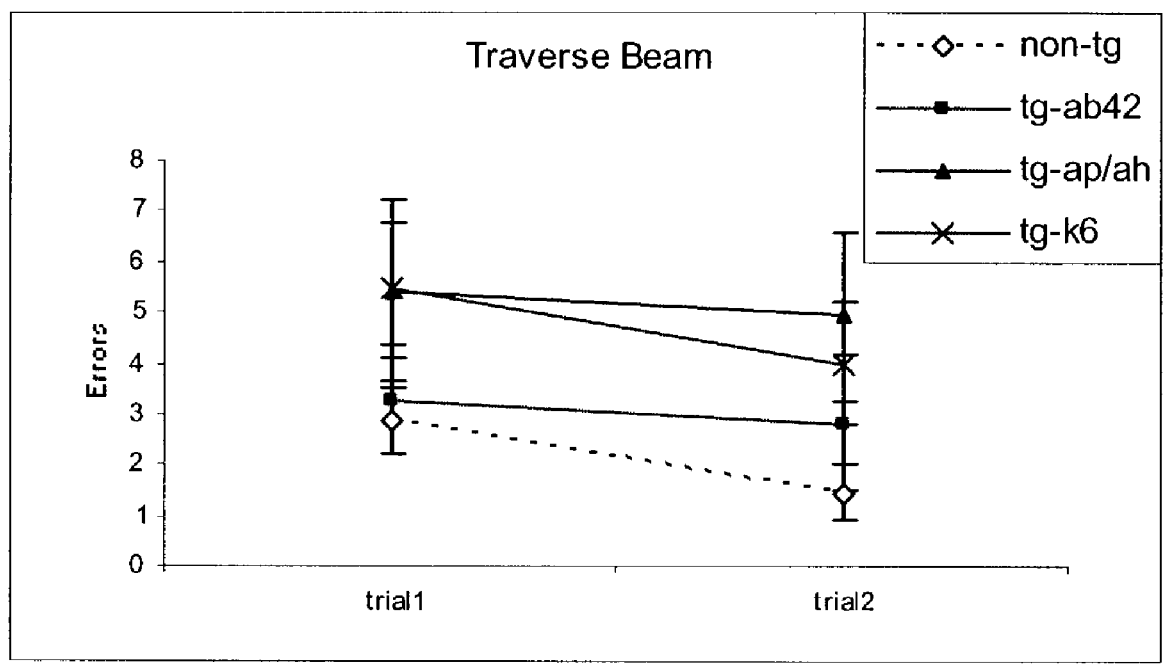
Figure 15C:
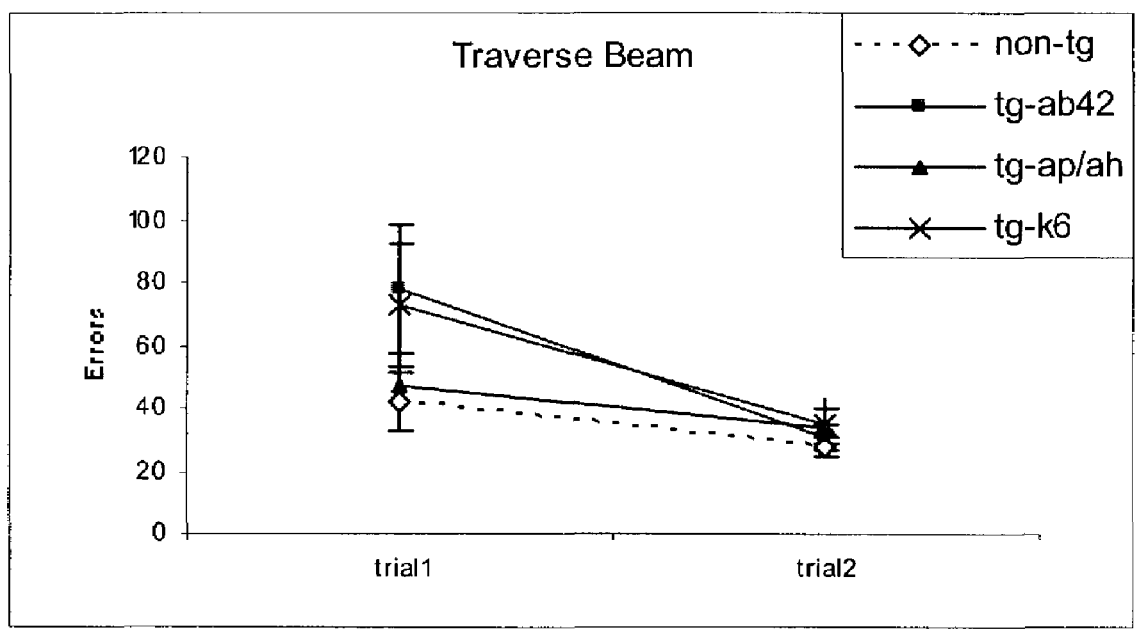
Figure 15D:
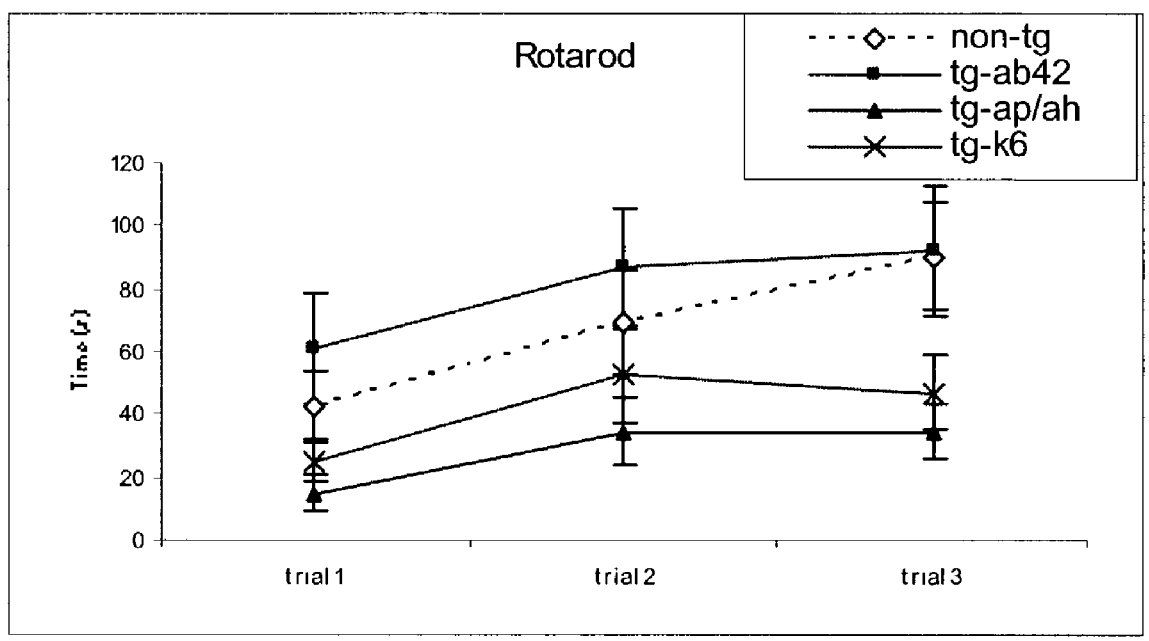
Figure 15E:
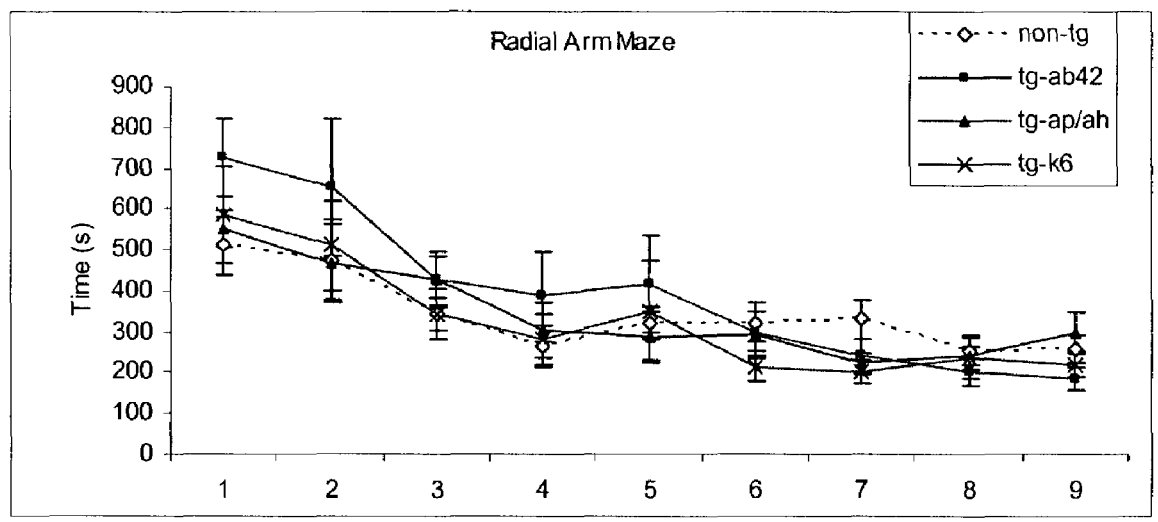
Figure 15F:
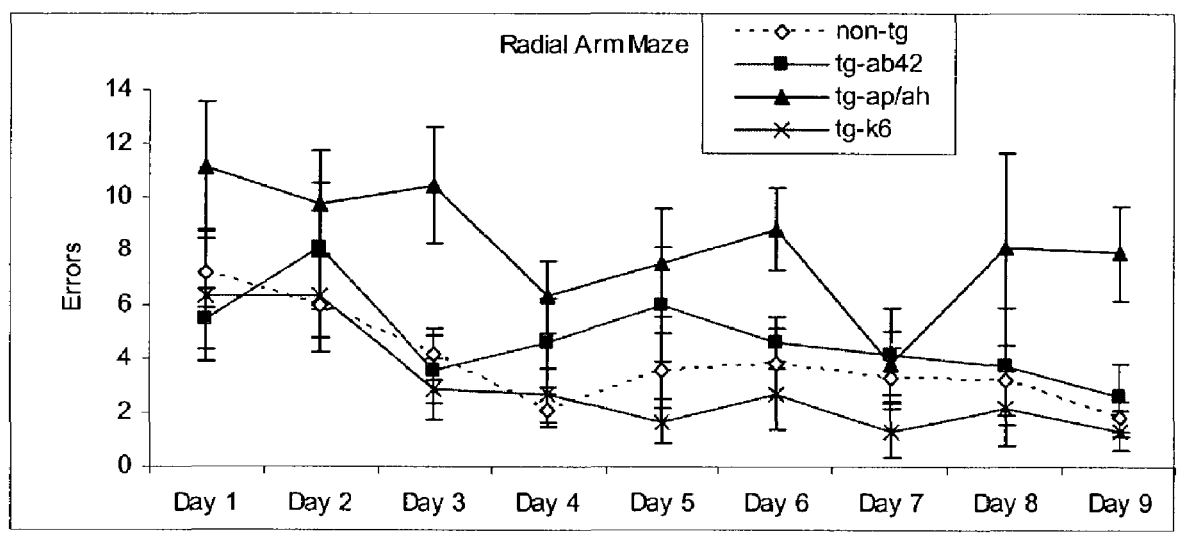
Figure 15G:
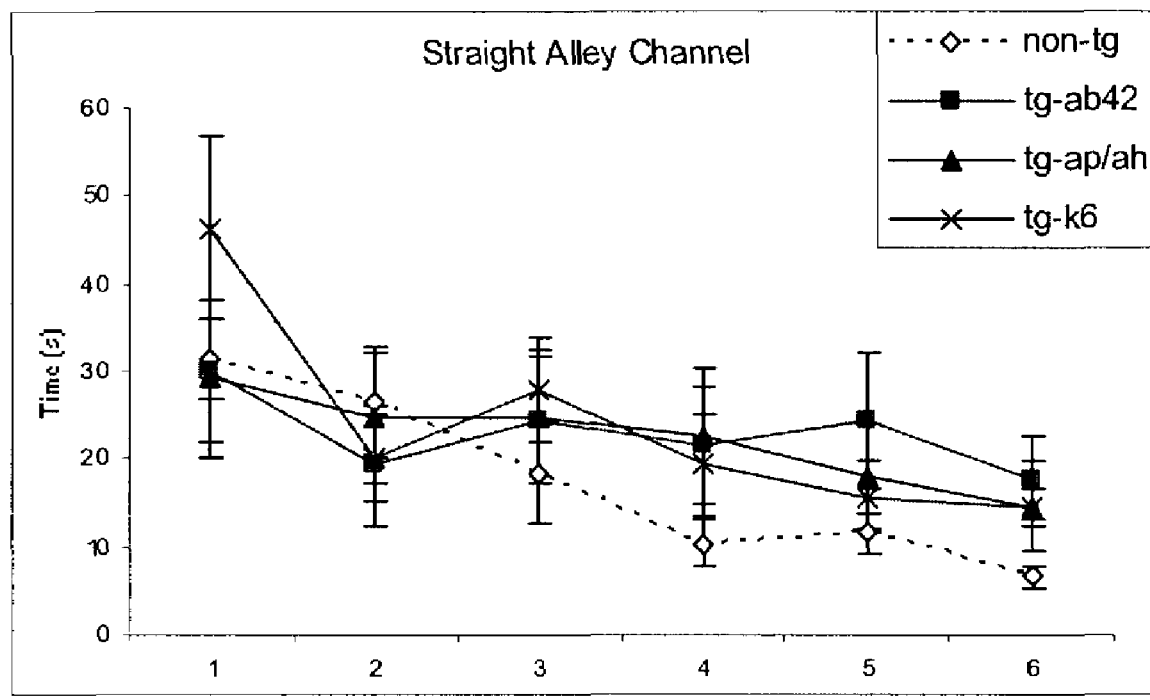
Figure 15H:
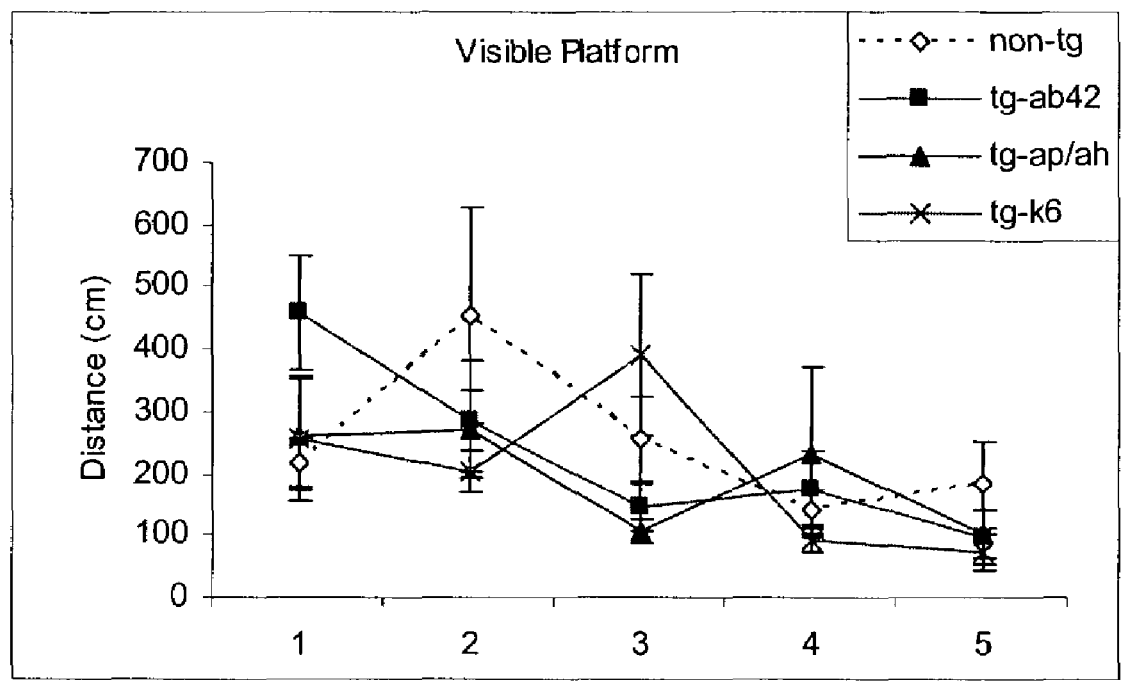
Figure 15I:
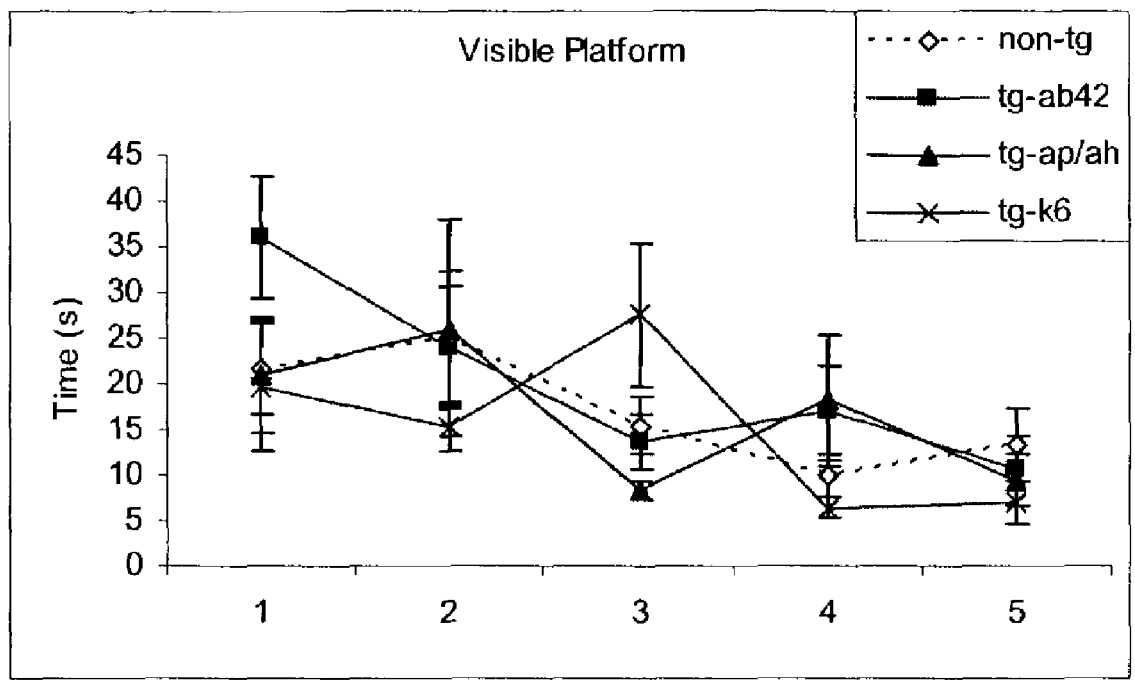
Figure 15J:
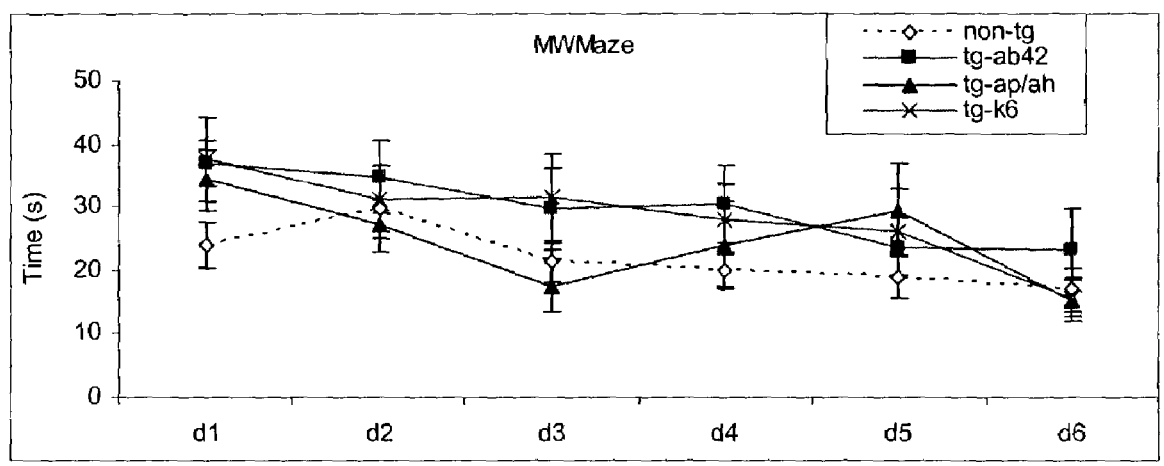
Figure 15K:
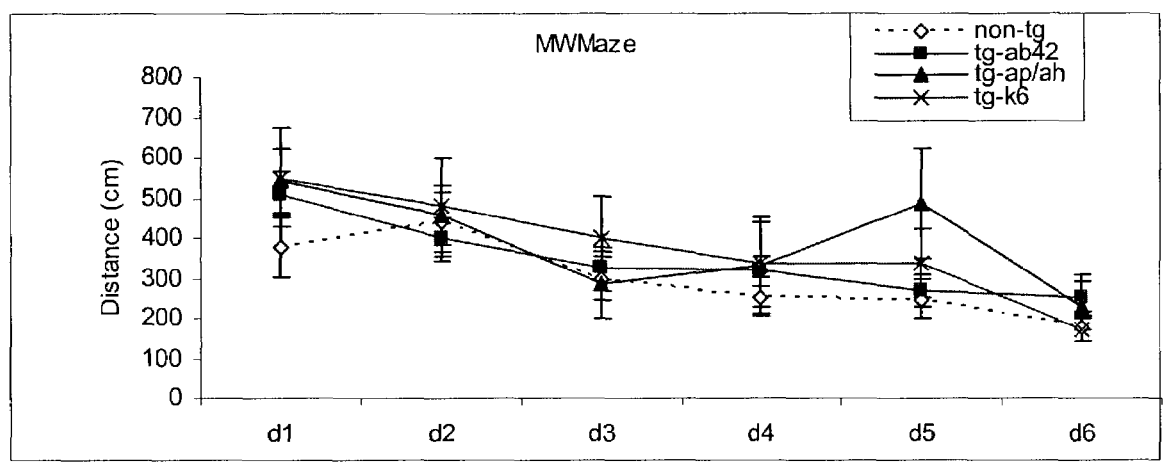
Figure 15L:
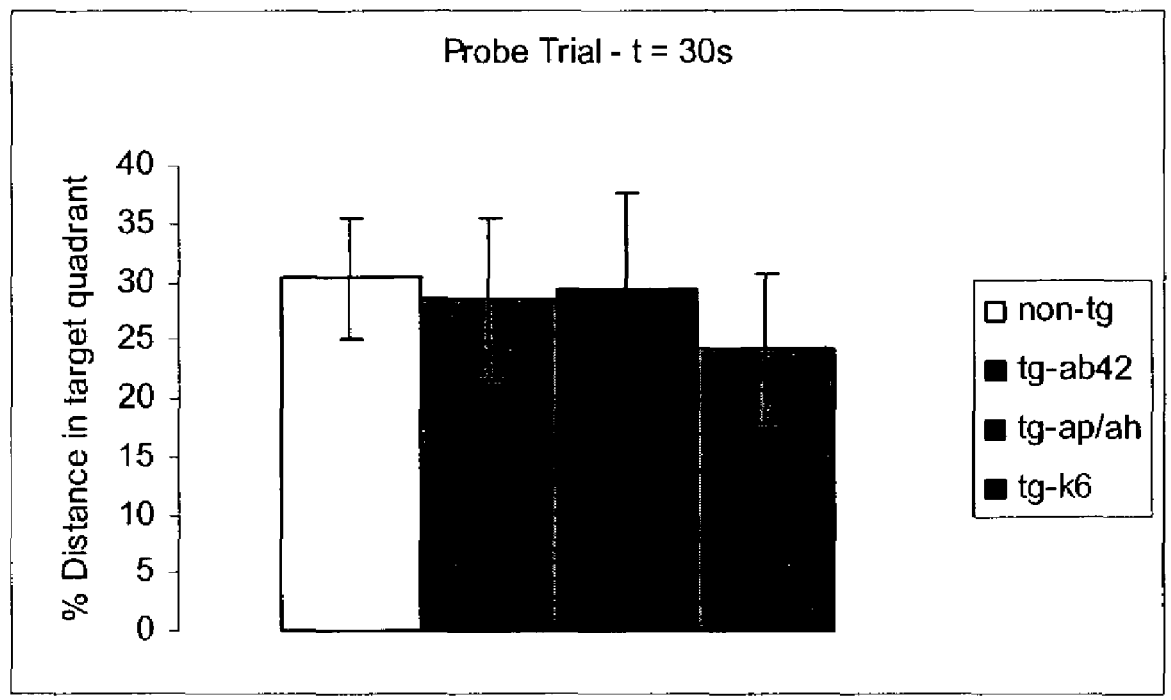
Figure 15M:
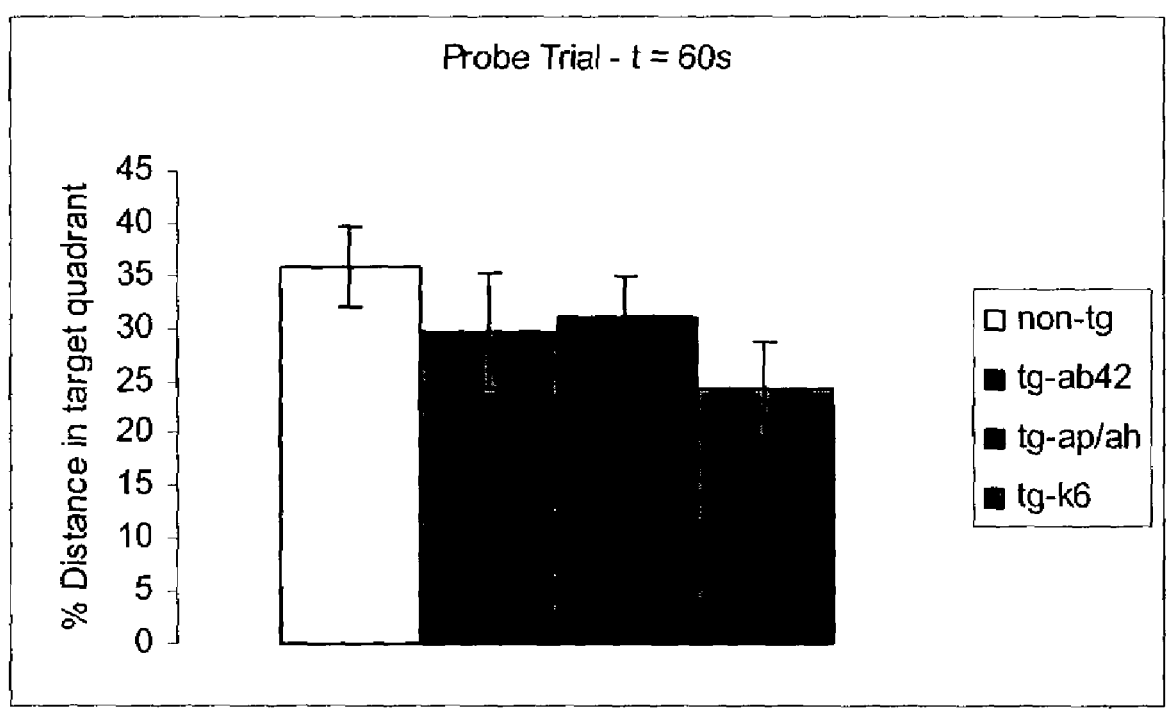
Figure 15N:
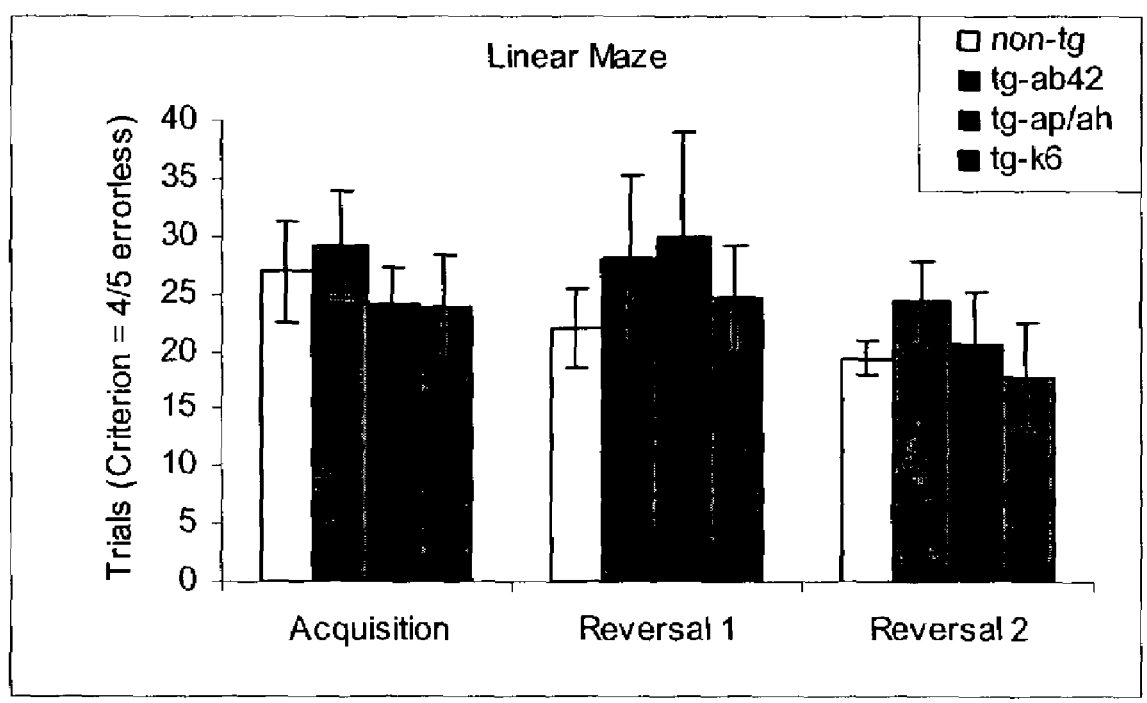

FIGS. 15A-N show the results obtained in the respective animal groups at 11 months of age. The figures show the results from testing of locomotor activity (FIG. 15A), and traverse beam (FIGS. 15B and 15C), rotarod (FIG. 15D), radial arm maze (FIGS. 15E and 15F), straight alley channel (FIG. 15G), visible platform (FIGS. 15H and 15I), Morris water maze (hidden platform) (FIGS. 15J and 15K), probe trial (FIGS. 15L and 15M), and linear maze (FIG. 15N) skills. The β-axis in FIGS. 15B and 15C represents Feeney scores and the total number of footslips, respectively.

In the radial arm maze test (FIG. 15F), signficant differences were found between the ntg-k6 versus tg-ah/ap groups (p=0.04), tg-ab42 versus tg-ah/ap (p=0.03), and tg-k6 versus tg-ah/ap (p=0.01), showing that animals vaccinated with tg-ab42 or tg-k6 had the radial arm maze skills of the positive control, i.e., the non-transgenic animals. Significant treatment effects were also observed in the rotarod (Two-way ANOVA: treatment; p=0.025; trials; p<0.0001). Neuman Keuls post hoc analysis revealed a significant difference between tg-42 and tg-ap/ah groups (p=0.035).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

References

Abeliovich et al., Mice lacking alpha-synuclein display functional deficits in the nigrostriatal dopamine system. Neuron 25: 239-252 (2000)
Aguado et al., Vaccine 17:2321-2328 (1999)
Alper et al., Does the agent of scrapie replicate without nucleic acid? Nature 214: 764-766 (1967)
Ammassari-Teule et al., Spatial learning and memory, maze running strategies and cholinergic mechanisms in two inbred strains of mice. Behav Brain Res 17:9-16 (1985)
Aucouturier et al., Biochemical and conformational variability of human prion strains in sporadic Creutzfeldt-Jakob disease, Neurosci. Lett. 274:33-36 (1999)
Barrow et al., J. Mol. Biol. 225:1075-1093 (1992)
Bateman et al., Sporadic Creutzfeldt-Jakob disease in a 18-year old in the UK. Lancet 346: 1155-1156 (1995)
Benkirane et al., Antigenicity and immunogenicity of modified synthetic peptides containing D-amino acid residues. J Biol Chem 268:26279-85 (1993)
Ben-Yedidia et al., A retro-inverso peptide analogue of influenza virus hemagglutinin B-cell epitope 91-108 induces a strong mucosal and systemic immune response and confers protection in mice after intranasal immunization. Mol Immunol 39:323 (2002)
Betarbet, Nat. Neurosci., 3:1301-1306 (2000)
Better et al., Science 240:1041-1043, (1988)
Biere et al., Parkinson's disease-associated alpha-synuclein is more fibrillogenic than . . . . J Biol Chem 275: 34574-34579 (2000)
Borges et al., Selective extraction of small and large molecules from the cerebrospinal fluid by Purkinje neurons. Science 228: 346-348 (1985)
Boulianne et al., Production of functional chimaeric mouse/human antibody, Nature 312:643-646, (1984)
Brett et al., Eur. J. Immunol. 23:1608 (1993)
Britton et al., Sporadic Creutzfeldt-Jakob disease in a 16-year old in the UK. Lancet 346: 1155 (1995)
Brown et al., Normal prion protein has an activity like that of superoxide dismutase, Bichem. 344:1-57 (1999)
Bueler et al., Mice devoid of PrP are resistant to scrapie. Cell 73: 1339-1347 (1993)
Bueler et al., Normal development and behaviour of mice lacking the neuronal cell-surface PrP protein. Nature 356: 577-582 (1992)
Burdick et al., J. Biol. Chem. 267:546-554 (1992)
Bush et al., Science 265:1464-1467 (1994)
Bushchle et al., Transloading of tumor antigen-derived peptides into antigen-presenting cells, Proc Natl Acad Sci USA, 94:(7)3256-61 (1997)
Cabilly et al., European Patent Application 125.023 (published Nov. 14, 1984)
Cabilly et al., Proc. Natl. Acad. Sci. USA 81:3273-3277, (1984)
Castaño et al., Fibrillogenesis in Alzheimer's disease of amyloid beta peptides and apolipoprotein E, Biochem. J. 306: 599-604 (1995)
Castaño et al., In vitro formation of amyloid fibrils from two synthetic peptides of different lengths homologous to Alzheimer's disease beta-protein, Biochem. Biophys. Res. Commun 141:782-789 (1986)
Caughey et al., Potent inhibition of scrapie-associated PrP accumulation by congo red. J Neurochem 59: 768-771 (1992)
Caughey et al., Scrapie infectivity correlates with converting activity, protease resistance, and aggregation of scrapie-associated prion protein in guanidine denaturation studies. J Virol 71: 4107-4110 (1997)
Chesebro et al., Identification of scrapie prion protein-specific mRNA in scrapie infected and uninfected brain. Nature 315: 331-333 (1995)
Collee et al., BSE: a decade on. Lancet 349: 636-641 (1997)
Colligan et al., Current Protocols in Immunology, Green Publishing Assoc., and Wiley Interscience, New York, (1993)
Collinge et al., Molecular analysis of prion strain variation and the aetiology of 'new variant' CJD. Nature 383: 685-690 (1996)
Collinge et al., Prion protein is necessary for normal synaptic function. Nature 370: 295-297 (1994)

Collinge, Human prion diseases and bovine spongiform encephalopathy (BSE). Hum Mol Genet 6: 1699-1705 (1997)

Conway et al., Fibrils formed in vitro from alpha-synuclein and two mutant forms linked to Parkinson's disease are typical amyloid. Biochemistry 39: 2552-2563 (2000)

Couce et al., Treatment with growth hormone and dexamethasone in mice transgenic for human islet amyloid polypeptide causes islet amyloidosis and beta-cell dysfunction. Diabetes 45:1094-1101 (1996).

D'Alessio et al., Pancreatic expression and secretion of human islet amyloid polypeptide in a transgenic mouse. Diabetes 43:1457-1461 (1994).

Dawson et al., Neuron 35:219-222 (2002)

de Koning et al., Diabetes mellitus in Macaca mulatta monkeys is characterised by islet amyloidosis and reduction in beta-cell population. Diabetologia 36:378-384 (1993)

Deidrich et al., Proc Nat'l Acad Sci USA 88:375-379 (1991)

Deierkauf et al., Phygocytosis by rabbit polymorphonuclear leukocytes: the effect of albumin and polyamine acids on latex uptake, J Cell Physiol, 92(2):169-75 (1977)

Dietzschold et al., Delineation of putative mechanisms involved in antibody-mediated clearance of rabies virus from the central nervous system (published erratum appears in Proc Natl Acad Sci U S A 1992 Oct 1;89(19): 9365). Proc Natl Acad Sci U S A 89: 7252-7256 (1992)

DiNicola et al., Large-scale feasibility of gene transduction into human cd34+cell-derived dendritic cells by adenoviral/polycation complex, Br J Haematol, 111(1):344-50 (2000)

Dlouhy et al., Linkage of the Indiana kindred of Gertmann-Straussler Scheinker disease to the prion protein gene. Nat Genet 1: 64-67 (2000)

Drlicek et al., Circulating antineuronal antibodies reach neurons in vivo: an autopsy study. J Neurol 239: 407-410 (1992)

Enari et al., Scrapie prion protein accumulation by scrapie-infected neuroblastoma cells abrogated by exposure to a prion protein antibody, Proc. Natl. Acad. Sci. U.S.A. 98:9295-9299 (2001)

Eshhar et al., Br. J. Cancer Suppl., 10:27-9 (1990)

Exley et al., FEBS Lett. 324:293-295 (1993)

Fabian et al., Intraneuronal IgG in the central nervous system: uptake by retrograde axonal transport. Neurology 37: 1780-1784 (1987)

Farmer, Bridging the gap between bioactive peptides and nonpeptides: some perspectives in design. In: Drug Design; Ariens, E. J., Ed.; Academic Press: New York; Vol. 10, pp 119-143 (1980)

Feany et al., Nature 404:394-398 (2000)

Fernandez-Funez et al., Identification of genes that modify ataxin-1-induced neurodegeneration. Nature 408:101-106 (2000)

Fishman et al., Internalization of plasma proteins by cerebellar Purkinje cells. J Neurol Sci 100: 43-49 (1990)

Fletcher et al., Partially modified retro-inverso peptides: development, synthesis, and conformational behaviour. Chem. Rev. 98:763-795 (1998)

Forsell et al., Neurosci. Lett. 184:90-93 (1995)

Fox et al., Human islet amyloid polypeptide transgenic mice as a model of non-insulin-dependent diabetes mellitus (NIDDM). FEBS Lett. 323:40-44 (1993).

Gajdusek et al., Clinical, pathological and epidemiological study of an acute progressive degenerative disease of the central nervous system among natives of the eastern highlands of New Guinea. Am J Med 26: 442-469 (1959)

Gajdusek et al., Degenerative disease of the central nervous system in New Guinea: the epidemic occurrence of "kuru" in the native population. N Eng J Med 257: 974-978 (1957)

Gajdusek et al., Experimental transmission of a kuru-like syndrome to chimpanzees. Nature 209: 794-796 (1966)

Games et al., Nature 373:523-527 (1995)

Gerstmann et al., Uber eine eigenartige hereditar-familiare erkrankung des zentral-nervensystems sugleich ein beitrag zur frage des vorzeitigen lokalen alterns. Z Neurol 154: 736-762 (1936)

Ghetti et al., Familial Gerstmann-Straussler-Scheinker disease with neurofibrillary tangles. Mol Neurobiol 8: 41-48 (1994)

Ghetti et al., Vascular variant of prion protein cerebral amyloidosis with T-positive neurofibrillary tangles: The phenotype of the stop codon 145 mutation in PRNP. Proc Natl Acad Sci USA 93:744-748 (1996)

Ghiso et al. Biochem. J. 293:27-30 (1994)

Ghiso et al., Epitope map of two polyclonal antibodies that recognize amyloid lesions in patients with Alzheimer's disease, Biochem. J. 282:517-522 (1992)

Giasson et al., A hydrophobic stretch of 12 amino acid residues in the middle of alpha-synuclein is essential for filament assembly. J Biol Chem 276: 2380-2386 (2001)

Giasson et al., Neuron 34:521-533 (2002)

Goedert, Alpha-synuclein and neurodegenerative diseases. Nat Rev Neurosci 2: 492-501 (2001)

Golabek et al., The interaction between apolipoprotein E and Alzheimer's amyloid p-peptide is dependent on p-peptide conformation, J. Biol. Chem. 271:10602-10606 (1996)

Goldfarb et al., Fatal familial insomnia and familial Creutzfeldt-Jacob disease: disease phenotype determined by a DNA polymorphism. Science 258: 806-808 (1992)

Gordon, Advances in veterinary research. Vet Rec 58: 518-525 (1947)

Graus et al., Effect of intraventricular injection of an anti-Purkinje cell antibody (anti-Yo) in a guinea pig model. J Neurol Sci 106: 82-87 (1991)

Griffith, Self-replication and scrapie. Nature 215: 1043-1044 (1967)

Gross et al., Proc. Natl. Acad. Sci. USA, 86:10024-8 (1989)

Gutekunst et al., Nuclear and neuropil aggregates in Huntington's disease: relationship to neuropathology. J Neurosci 19: 2522-2534 (1999)

Hadlow, Scrapie and kuru. Lancet 11: 289-290 (1959)

Hagan et al., Molec. Immunol. 28:287-294 (1991)

Hagan et al., Vaccine 9:768-771 (1991)

Harlow et al., ANTIBODIES: A LABORATORY MANUAL, Cold Spring Harbor Laboratory, Cold Spring Harbor, N.Y. (1988)

Harris et al., Processing of a cellular prion protein: identification of N-terminal and C-terminal cleavage sites. Biochem 32: 1009-1016 (1993)

Hart et al., Stereochemical aspects of drug action I: Conformational restriction, steric hindrance and hydrophobic collapse. In: Pract. Med. Chem.; Wermuth, C., Ed.; Acad. Press: London, U.K.; pp 393-412 (1996)

Heiser et al., Inhibition of huntingtin fibrillogenesis by specific antibodies and small molecules: implications for Huntington's disease therapy. Proc Natl Acad Sci U S A 97: 6739-6744 (2000)

Hely et al., Treatment of Parkinson's disease. J Clin Neurosci 7: 484-494 (2000)

Hilbich et al., J. Mol. Biol. 228:460-473 (1992)

Hodgson et al., A YAC mouse model for Huntington's disease with full-length mutant huntingtin, cytoplasmic toxicity, and selective striatal neurodegeneration. Neuron 23:181-192 (1999)

Holcomb et al., Accelerated Alzheimer-type phenotype in transgenic mice carrying both mutant amyloid precursor protein and presenilin 1 transgenes, Nat. Genet. 4:97-100 (1998).

Höppener et al., Chronic overproduction of islet amyloid polypeptide/amylin in transgenic mice: lysosomal localization of human islet amyloid polypeptide and lack of marked hyperglycaemia or hyperinsulinaemia. Diabetologia 36:1258-1265 (1993).

Höppener et al., Extensive islet amyloid formation is induced by development of type II diabetes mellitus and contributes to its progression: pathogenesis of diabetes in a mouse model. Diabetologia 42:427-434 (1999).

Höppener et al., Islet amyloid and type 2 diabetes mellitus. N Engl J Med 343:411-419 (2000)

Horwich et al., Deadly conformations-protein misfolding in prion diseases. Cell 89: 499-510 (1997)

Howard, Insular amyloidosis and diabetes mellitus in Macaca nigra. Diabetes 27:357-364 (1978)

Howard, Longitudinal studies on the development of diabetes in individual Macaca nigra. Diabetologia 29: 301-306 (1986)

Hsiao et al., Correlative memory deficits, Aβ elevation and amyloid plaques in transgenic mice, Science 274:99-102 (1996)

Hsiao et al., Mutant prion proteins in Gerstmann-Straussler-Scheinker disease with neurofibrillary tangles. Nature Genet 1: 68-71 (1992)

Hsiao et al., Serial transmission in rodents of neurodegeneration from transgenic mice expressing mutant prion protein. Proc Natl Acad Sci (USA) 91: 9126-9130 (1994)

Hughes et al., Therapeutic opportunities in polyglutamine disease. Nat Med 7: 419-423 (2001)

Inzucchi et al., Efficacy and metabolic effects of metformin and troglitazone in type II diabetes mellitus. N Engl J Med 338: 867-872 (1998)

Isberg et al., Cell 60:861 (1990)

Jacob, Uber eigenaritge erkrankungen des zentral-nervensystems mit bemerkenswertem anatomischen befunde (spastische pseudosklerose-encephalomyelopathie mit disseminierten degenerationsherden). Z Gesamte Neurol Psychiatre 64: 147-228 (1921)

Jaikaran et al., Biochim. Biophys. Acta, 1537:179-203 (2001)

Jameson et al., The Antigenic Index: A Novel Algorithm for Predicating Antigenic Determinants, Comput. Appl. Biosci. 4:181-186 (1988)

Janson et al., The mechanism of islet amyloid polypeptide toxicity is membrane disruption by intermediate-sized toxic amyloid particles. Diabetes 48: 491-498 (1999)

Jarrett et al., Biochem. 32 :4693-4697 (1993)

Jarrett et al., Cell 73:1055-1058 (1993)

Johnson et al., Islet amyloid, islet-amyloid polypeptide, and diabetes mellitus. N Engl J Med 321: 513-518 (1989)

Kanecko et al., J. Mol. Biol., 295:997-1007 (2000)

Kang et al. Nature 325:503-507, 1987; Dyrks et al. EMBO J. 7:949-957, (1988)

Kascsak et al., "Immunodiagnosis of prion disease", Immun. Invest. 26:259-268 (1997)

Kaytor et al., Aberrant protein deposition and neurological disease. J Biol Chem 274: 37507-37510 (1999)

Kazemi-Esfarjani and S. Benzer, Genetic suppression of polyglutamine toxicity in Drosophila. Science 287:1837-1840 (2000).

Kisilevsky et al., Nature Medicine 1(2):143-148 (1995)

Kisilevsky, Anti-amyloid drugs: potential in the treatment of diseases associated with aging. Drugs Aging 8: 75-83 (1996)

Kitamoto et al., An amber mutation of prion protein in Gerstmann-Straussler syndrome-with mutant PrP plaques. Biochem Biophys Res Commun 192: 525-531 (1993)

Kohler et al., Nature 256:495-497 (1975)

Kosaka, Lewy bodies in cerebral cortex, report of three cases. Acta Neuropathol (Berl) 42: 127-134 (1978)

Koudinov et al., Biochem. Biophys. Res. Commun. 205: 1164-1171, (1994)

Kretzschmar et al., Scrapie prion protein are synthesized in neurons. Am J Pathol 122: 1-5 (1986)

Kudo et al., European Patent Application 184187 (published

Ladogana et al., Sulphate polyanions prolong the incubation period of scrapie-infected hamsters. J Gen Virol 73 (Pt 3): 661-665 (1992)

Laforet et al., Changes in cortical and striatal neurons predict behavioural and electrophysiological abnormalities in a transgenic murine model of Huntington's disease. J. Neurosci. 21:9112-9123 (2001)

Latarjet et al., Inactivation of the scrapie agent by near monchromatic ultraviolet light. Nature 227: 1341-1443 (1970)

Lee et al., Proc. Natl. Acad. Sci. USA 99:8968-8973 (2002)

LeVine, Thioflavine T interaction with synthetic Alzheimer's disease β-amyloid proteins: detection of amyloid aggregation in solution, Protein Sci. 2:404-410 (1993)

Liao et al., Human prion protein cDNA: molecular cloning, chromosomal mapping and biological implications. Science 233: 364-367 (1986)

Liedo et al., Mice deficient for prion protein exhibit normal neuronal excitability and synaptic transmission in the hippocampus. Proc Natl Acad Sci (USA) 93: 2403-2407 (1996)

Lin et al., Neurological abnormalities in a knock-in mouse model of Huntington's disease. Hum. Mol. Genet. 10:137-144 (2001)

Lindstrom et al., Effect of insulin treatment on circulating islet amyloid polypeptide in patients with NIDDM. Diabet Med 14: 472-476 (1997)

Liu et al., Brain Res 896:118-129 (2001)

Liu et al., Proc. Natl. Acad. Sci USA 84:3439-3443 (1987)

Mangiarini et al., Exon 1 of the HD gene with an expanded CAG repeat is sufficient to cause a progressive neurological phenotype in transgenic mice. Cell 87:493-506 (1996)

Manson et al., 129/Ola mice carrying a null mutation in PrP that abolishes mRNA production are developmentally normal. Mol Neurobiol 8: 121-127 (1994)

Marsh et al., Expanded polyglutamine peptides alone are intrinsically cytotoxic and cause neurodegeneration in Drosophila. Hum. Mol. Genet. 9 pp. 13-25 (2000), Martel et al., Neuroscience Letter, 206:157-160 (1996)

Martinez-Fong et al., "Nonenzymatic glycosylation of poly-L-lysine: a new tool for targeted gene delivery", Hepatology, 20(6):1602-8 (1994)

Medori et al., Fatal familial insomnia, a prion disease with a mutation at codon 178 of the prion protein gene. N Eng J Med 326: 444-449 (1992)

Merlini et al., Proc. Natl. Acad. Sci. USA 92:2959-2963 (1995)

Merz et al., Abnormal fibrils from scrapie-infected brain. Acta Neuropathol 54: 63-74 (1981)

Mirzabekov et al., Pore formation by the cytotoxic islet amyloid peptide amylin. J Biol Chem 271: 1988-1992 (1988-1992)

Moriarty et al., Effects of sequential proline substitutions on amyloid formation by human amylin20-29. Biochemistry 38: 1811-1818 (1999)

Morrison et al., European Patent Application 173494 (published Mar. 5, 1986)

Morrison et al., Proc. Natl. Acad. Sci. USA 81:6851-6855, (1984)

Muller-Hill and Beyreuther, Ann. Rev. Biochem. 38:287-307 (1989)

Neuberger et al., Nature 314:268-270, (1985)

Neuberger et al., PCT Application WO 8601533, (published Mar. 13, 1986)

O'Brien et al., Immunohistochemical morphometry of pancreatic endocrine cells in diabetic, normoglycaemic, glucose-intolerant and normal cats. J. Comp. Pathol. 96:357-369 (1986).

Oesch et al., A cellular gene encodes scrapie PrP 27-30 protein. Cell 40: 735-746 (1985)

Pallitto et al., Biochemistry 38:3570-3578 (1999)

Pan et al., Conversion of alpha-helices into β-sheets features in the formation of scrapie prion poteins. Proc Natl Acad Sci (USA) 90: 10962-10966 (1993).

Peretz et al., "Antibodies inhibit prion propagation and clear cell cultures of prion infectivity", Nature 412:739-743 (2001)

Peterson et al., "Polyamino acid enhancement of bacterial phagocytosis by human polymorphonuclear leukocytes and peritoneal macrophages", Infect Immun 43(2):561-6 (1984)

Pocchiari et al., Amphotericin B delays the incubation period of scrapie in intracerebrally inoculated hamsters. J Gen Virol 68 (Pt 1): 219-223 (1987)

Polymeropoulos et al., Mutation in the alpha-synuclein gene identified in families with Parkinson's disease. Science 276: 2045-2047 (1997)

Priola et al., Porphyrin and phthalocyanine antiscrapie compounds. Science 287: 1503-1506 (2000)

Prusiner et al., Ablation of the prion protein (PrP) gene in mice prevents scrapie and facilitates production of anti-PrP antibodies. Proc Natl Acad Sci (USA) 90: 10608-10612 (1993)

Prusiner et al., Prion protein biology. Cell 93: 337-348 (1998)

Prusiner, Novel proteinaceous infectious particles cause scrapie. Science 216: 136-144 (1982)

Quartermain et al., Enoxaparin, a low molecular weight heparin decreases infarct size and improves sensorimotor function in a rat model of focal cerebral ischemia. Neurosci Lett 288:155-8 (2000).

Reddy et al., Behavioural abnormalities and selective neuronal loss in HD transgenic mice expressing mutated full-length HD cDNA. Nat. Genet. 20:198-202 (1998)

Ripka et al., Peptidomimetic design. Curr. Opin. Chem. Biol. 2:441-452 (1998)

Robinson et al., International Patent Publication WO 9702671 (published May 7, 1987)

Roullet et al., Detection of object orientation and spatial changes by mice: importance of local views, Physiol Behav 64:203-7 (1998)

Roullet et al., Radial maze learning using exclusively distant visual cues reveals learners and nonlearners among inbred mouse strains. Physiol Behav 58:1189-95 (1995)

Rubinsztein et al., Intracellular inclusions, pathological markers in diseases caused by expanded polyglutamine tracts? J Med Genet 36: 265-270 (1999)

Rubinsztein, Trends Gen. 18:202-206 (2002)

Safar et al., Thermal stability and conformational transitions of scrapie amyloid (prion) protein correlates with infectivity. Protein Sci 2: 2206-2216 (1993)

Sahagan et al., J. Immunol. 137:1066-1074, (1986)

Sakaguchi et al., Loss of cerebellar Purkinje cells in aged mice homozygous for a disrupted PrP gene. Nature 380: 528-531 (1996)

Schenk et al., Immunization with Amyloid-β Attenuates Alzheimer Disease-like Pathology in the PDAPP Mouse, Nature 400:173-177 (1999)

Schilling et al., Intranuclear inclusions and neuritic aggregates in transgenic mice expressing a mutant N-terminal fragment of huntingtin. Hum. Mol. Genet. 8:397-407 (1999)

Serpell et al., Fiber diffraction of synthetic alpha-synuclein filaments shows amyloid-like cross-beta conformation. Proc Natl Acad Sci U S A 97: 4897-4902 (2000)

Seubert et al., Nature 359:355-327 (1992)

Shelbourne et al., A Huntington's disease CAG expansion at the murine Hdh locus is unstable and associated with behavioural abnormalities in mice. Hum. Mol. Genet. 8:763-774 (1999)

Shen et al., "Disulfide spacer between methotrexate and poly (D-lysine). A probe for exploring the reductive process in endocytosis", J. Biol. Chem, 260(20):10905-8 (1985)

Shoji et al., Science 258:126-129 (1992)

Shyng et al., A prion protein cycles between the cell surface and endocytic compartment in cultured neuroblastoma cells. J Biol Chem 268: 15922-15928 (1997)

Sigurdsson et al., Anti-prion antibodies for prophylaxis following prion exposure in mice. Neuroscience Lett (in press, 2002)

Sigurdsson et al., Immunization delays the onset of prion disease in mice. Am J Pathol 161:13-17 (2002)

Sigurdsson et al., Immunization with a nontoxic/nonfibrillar amyloid-β homologous peptide reduces Alzheimer's Disease-associated pathology in transgenic mice. Am J Pathol 159:439-447 (2001)

Sigurdsson et al., In vivo reversal of amyloid-β lesions in rat brain. J Neuropath Exp Neurol 59: 11-17 (2000)

Sigurdsson et al., Infectivity of amyloid diseases, Trends in Molecular Medicine 8:411-413 (2002)

Sigurdsson et al., Local and distant histopathological effects of unilateral amyloid-beta 25-35 injections into the amygdala of young F344 rats, Neurobiol. Aging 17:893-901 (1996)

Sobotka et al., Neurobehavioral studies of tremorgenic mycotoxins verruculogen and penitrem A. Pharmacology 16:287-94 (1978).

Soeller et al., Islet amyloid-associated diabetes in obese A(vy)/a mice expressing human islet amyloid polypeptide. Diabetes 47:743-750 (1998).

Soto et al. J. Neurochem. 63:1191-1198 (1994)

Soto et al., Alzheimer's soluble p-amyloid is conformationally modified by apolipoproteins in vitro, Neuroreport 7:721725 (1996)

Soto et al., Apolipoprotein E increases the fibrillogenic potential of synthetic peptides derived from Alzheimer's, gelsolin and AA amyloids, FEBS Lett. 371:110-114 (1995)

Soto et al., Biochem. J. 314:701-707 (1996)

Soto et al., Reversion of prion protein conformational changes by synthetic beta-sheet breaker peptides. Lancet 355: 192-197 (2000)

Soto et al., The alpha-helical to beta-strand transition in the amino-terminal fragment of the amyloid beta-peptide modulates amyloid formation, J. Biol. Chem. 270:3063-3067 (1995)

Soto et al., β-sheet breaker peptides inhibit fibrillogenesis in a rat brain model of amyloidosis: Implications for Alzheimer's therapy. Nat Med 4: 822-826 (1998)

Spatola, Peptide backbone modifications: a structure-activity analysis of peptides containing amide bond surrogates, conformational constraints, and related backbone replacements. In: Chem. Biochem. Amino Acids, Pept., Proteins; Weinstein, B., Ed.; Marcel Dekker: New York; pp 267-257 (1983)

Spillantini et al., Alpha-synuclein in Lewy bodies. Nature 388: 839-840 (1997)

Strittmatter et al., Proc. Natl. Acad. Sci. USA 90:1977-1981, (1993)

Sun et al., Proc. Natl. Acad. Sci. USA 84:214-218, (1987)

Surewicz et al., Determination of protein secondary structure by Fourier transform infrared spectroscopy: a critical assessment, Biochem. 32:389-394 (1993)

Tagliavini et al., Effectiveness of anthracycline against experimental prion disease in Syrian hamsters. Science 276: 1119-1122 (1997)

Taniguchi et al., European Patent Application 171496 (published Feb. 19, 1985)

Taraboulos et al., Synthesis and trafficking of prion proteins in cultured cells. Mol Biol Cell 3: 851-863 (1992)

Telling et al., Interactions between wild-type and mutant prion proteins modulate neurodegeneration transgenic mice. Genes Dev 10: 1736-1750 (1996)

Telling et al., Prion propagation in mice expressing human and chimeric PrP transgenes implicates the interaction of cellular PrP with another protein. Cell 83: 79-90 (1995)

Telling et al., Transmission to Creutzfeldt-Jacob disease from human to transgenic mice expressing chimeric human-mouse prion protein. Proc Natl Acad Sci (USA) 91: 9936-9940 (1994)

Tobler et al., Altered circadian activity rhythms and sleep in mice devoid of prion protein. Nature 380: 639-642 (1996)

Tran Van Nhieu et al., J. Biol. Chem. 266:24367 (1991)

Verchere et al., Islet amyloid formation associated with hyperglycemia in transgenic mice with pancreatic beta cell expression of human islet amyloid polypeptide. Proc. Natl. Acad. Sci. USA 93:3492-3496 (1996)

Verchere et al., Transgenic overproduction of islet amyloid polypeptide (amylin) is not sufficient for islet amyloid formation. Hormone Metab. Res. 29:311-316 (1997)

Wang et al., "Endocytosis of horseradish peroxidase-polylysine conjugate by glomerular epithelial cells: an in vivo study", J. Pathol., 159(2):159-67 (1989)

Warrick et al., Suppression of polyglutamine-mediated neurodegeneration in Drosophila by the molecular chaperone HSP70. Nat. Genet. 23:425-428 (1999)

Weissmann, Molecular biology of transmissible spongiform encephalopathies. FEBS Lett 389: 3-11 (1996)

Westermark et al., Islet amyloid polypeptide: pinpointing amino acid residues linked to amyloid fibril formation. Proc Natl Acad Sci U S A 87: 5036-5040 (1990)

White et al., Huntingtin is required for neurogenesis and is not impaired by the Huntington's disease CAG expansion. Nat. Genet. 17:404-410 (1997)

Will et al., A new variant of Creutzfeldt-Jacob disease in the UK. Lancet 347: 921-925 (1997)

Wisniewski et al., Acceleration of Alzheimer's fibril formation by apolipoprotein E in vitro, Am. J. Pathol. 145:1030-1035 (1994)

Wisniewski et al., Ann. Neurol. 17:278-282 (1985)

Wisniewski et al., Cerebrospinal fluid inhibits Alzheimer beta-amyloid fibril formation in vitro, Ann. Neurol. 34:631-633 (1993)

Wisniewski et al., Peptides homologous to the amyloid protein of Alzheimer's disease containing a glutamine for glutamic acid substitution have accelerated amyloid fibril formation, Biochem. Biophys. Res. Commun. 179:1247-1254 (1991)

Wood et al., Biochemistry 34:724-730 (1995)

Yamamoto et al., Reversal of neuropathology and motor dysfunction in a conditional model of Huntington's disease. Cell 101:57-66 (2000)

Yano et al., Ultrastructural evidence for intracellular formation by non-endocrine cells. Lab. Invest. 45:149-156 (1981)

Zagorski et al., Biochem. 31:5621-5631 (1992)

Zapecka-Dubno et al., Effect of oral antidiabetic agents on plasma amylin level in patients with non-insulin-dependent diabetes mellitus (type 2). Arzneimittelforschung 49: 330-334 (1999)

Zlokovic et al., Biochem. Biophys. Res. Commun. 205:1431-1437 (1994)

Zlokovic et al., Proc. Natl. Acad. Sci. USA 93:4229-04233 (1996)

Zoghbi et al., Glutamine repeats and neurodegeneration. Annu Rev Neurosci 23: 217-247 (2000)

---

SEQUENCE LISTING

<160> NUMBER OF SEQ ID NOS: 55

<210> SEQ ID NO 1
<211> LENGTH: 30
<212> TYPE: PRT
<213> ORGANISM: Artificial Sequence
<220> FEATURE:
<223> OTHER INFORMATION: Synthetic

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala
            20                  25                  30

```
<210> SEQ ID NO 2
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 either are present,
      together as all Lys or all Asp, or are all absent.  When residues
      7-10 are present then any one or all of residues 1-6 can either
      be absent or present as Lys or Asp to form, in combination with
      residues 7-10, a N-terminal
<220> FEATURE:
<223> OTHER INFORMATION: polylysine or polyaspartate segment of 4 to 10
      residues in length.
<220> FEATURE:
<221> NAME/KEY: misc_feature
<222> LOCATION: (27)..(31)
<223> OTHER INFORMATION: Amino acid residues 27-31 are LeuValPhePheAla
      in which at least one of residues 27-31 are substituted with Lys,
      Asp, or Glu.  The C-terminal Ala residue may be amidated.

<400> SEQUENCE: 2

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala
        35                  40

<210> SEQ ID NO 3
<211> LENGTH: 70
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10  are all Lys or all
      Asp, or are all absent. When residues 7-10 are present, then any
      one or all of amino acid residues 1-6 can either be absent or
      present as Lys or Asp to form, in combination with residues 7-10,
      a N-terminal polylysine or
<220> FEATURE:
<223> OTHER INFORMATION: polyaspartate segment of 4 to 10 residues in
      length.
<220> FEATURE:
<221> NAME/KEY: misc_feature
<222> LOCATION: (27)..(31)
<223> OTHER INFORMATION: Amino acid residues 27-31 and 57-61 are the
      same and are LeuValPhePheAla in which at least one of residues
      27-31 and the same at least one residues of residues 57-61 are
      substituted with Lys, Asp, or Glu.  The C-terminal Ala residue
      may be amidated.
<220> FEATURE:
<221> NAME/KEY: misc_feature
<222> LOCATION: (57)..(61)
<223> OTHER INFORMATION: Amino acid residues 27-31 and 57-61 are the
      same and are LeuValPhePheAla in which at least one of residues
      27-31 and the same at least one residues of residues 57-61 are
      substituted with Lys, Asp, or Glu.  The C-terminal Ala residue
      may be amidated.

<400> SEQUENCE: 3

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30
```

```
Asp Val Gly Ser Asn Lys Gly Ala Asp Ala Glu Phe Arg His Asp Ser
        35                  40                  45

Gly Tyr Glu Val His His Gln Lys Xaa Xaa Xaa Xaa Xaa Glu Asp Val
    50                  55                  60

Gly Ser Asn Lys Gly Ala
65                  70

<210> SEQ ID NO 4
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(40)
<223> OTHER INFORMATION: Amino acid residues 31-34 are all Lys or all
      Asp or are all absent. When all residues 31-34 are present, then
      any one or all of residues 35-40 can either be absent or present
      as Lys or Asp to form, in combination with residues 31-34, a
      C-terminal polylysine or
<220> FEATURE:
<223> OTHER INFORMATION: polyaspartate segment of 4 to 10 residues in
      length.
<220> FEATURE:
<221> NAME/KEY: misc_feature
<222> LOCATION: (17)..(21)
<223> OTHER INFORMATION: Amino acid residues 17-21 are LeuValPhePheAla
      in which at least one of residues 17-21 is substituted with Lys,
      Asp, or Glu.

<400> SEQUENCE: 4

Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala Xaa Xaa
                20                  25                  30

Xaa Xaa Xaa Xaa Xaa Xaa Xaa Xaa
            35                  40

<210> SEQ ID NO 5
<211> LENGTH: 70
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (61)..(70)
<223> OTHER INFORMATION: Amino acid residues 61-64 are all Lys or all
      Asp, or are all absent. When all residues 61-64 are present,
      then any one or all of residues 65-70 can either be Lys or Asp to
      form, in combination with residues 61-64, a C-terminal polylysine
      or polyaspartate
<220> FEATURE:
<223> OTHER INFORMATION: segment of 4 to 10 residues in length.
<220> FEATURE:
<221> NAME/KEY: misc_feature
<222> LOCATION: (17)..(21)
<223> OTHER INFORMATION: Amino acid residues 17-21 and 47-51 are the
      same and are LeuValPhePheAla in which at least one of residues
      17-21 and the same at least one residues of 47-51 are the same at
      least one residues substituted with Lys, Asp, or Glu.
<220> FEATURE:
<221> NAME/KEY: misc_feature
<222> LOCATION: (47)..(51)
<223> OTHER INFORMATION: Amino acid residues 17-21 and 47-51 are the
      same and are LeuValPhePheAla in which at least one of residues
      17-21 and the same at least one residues of 47-51 are the same
      at least one residues substituted with Lys, Asp, or Glu.

<400> SEQUENCE: 5
```

-continued

```
Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala Asp Ala
                20                  25                  30

Glu Phe Arg His Asp Ser Gly Tyr Glu Val His His Gln Lys Xaa Xaa
            35                  40                  45

Xaa Xaa Xaa Glu Asp Val Gly Ser Asn Lys Gly Ala Xaa Xaa Xaa Xaa
        50                  55                  60

Xaa Xaa Xaa Xaa Xaa Xaa
65                  70

<210> SEQ ID NO 6
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: C-terminal residue 36 may be amidated.

<400> SEQUENCE: 6

Lys Lys Lys Lys Lys Lys Asp Ala Glu Phe Arg His Asp Ser Gly Tyr
1               5                   10                  15

Glu Val His His Gln Lys Leu Val Phe Phe Ala Glu Asp Val Gly Ser
                20                  25                  30

Asn Lys Gly Ala
        35

<210> SEQ ID NO 7
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 1-6 can either be absent
      or present as Lys or Asp to form, in combination with residues
      7-10, a N-terminal polylysine or polyaspartate segment of 4 to10
      residues in length.
<220> FEATURE:
<221> NAME/KEY: misc_feature
<223> OTHER INFORMATION: The C-terminal Ala residue may be amidated.

<400> SEQUENCE: 7

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Leu Val Phe Phe Ala Glu
                20                  25                  30

Asp Val Gly Ser Asn Lys Gly Ala
        35                  40

<210> SEQ ID NO 8
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(40)
<223> OTHER INFORMATION: Amino acid residues 35-40 can either be absent
      or present as Lys or Asp to form, in combination with residues
      31-34, a C-terminal polylysine or polyaspartate segment of 4-10
``` residues in length.

<400> SEQUENCE: 8

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Xaa Xaa
                20                  25                  30

Xaa Xaa Xaa Xaa Xaa Xaa Xaa Xaa
        35                  40

<210> SEQ ID NO 9
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 are all Lys or all
      Asp. Any one or all of residues 1-6 can either be absent or
      present as Lys or Asp to form, in combination with residues 7-10,
      a N-terminal polylysine or polyaspartate segment of 4 to 10
      residues in length.
<220> FEATURE:
<221> NAME/KEY: misc_feature
<222> LOCATION: (27)..(31)
<223> OTHER INFORMATION: Amino acid residues 27-31 are LeuValPhePheAla
      in which at least one of residues 27-31 are substituted with Lys,
      Asp, or Glu.
<220> FEATURE:
<221> NAME/KEY: misc_feature
<222> LOCATION: (41)..(50)
<223> OTHER INFORMATION: Amino acid residues 41-44 are all Lys or all
      Asp. Any one or all of residues 45-50 can be either absent or
      present as Lys or Asp to form, in combination with residues 41-44,
      a C-terminal polysine or polyaspartate segment of 4-10 residues.

<400> SEQUENCE: 9

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
                20                  25                  30

Asp Val Gly Ser Asn Lys Gly Ala Xaa Xaa Xaa Xaa Xaa Xaa Xaa Xaa
        35                  40                  45

Xaa Xaa
    50

<210> SEQ ID NO 10
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 are all Lys or all
      Asp. Any one or all of amino acid residues 1-6 can either be
      absent or present as Lys or Asp to form, in combination with
      residues 7-10, a N-terminal polylysine or polyaspartate segment
      of 4 to 10 residues in length.
<220> FEATURE:
<221> NAME/KEY: misc_feature
<222> LOCATION: (27)..(31)
<223> OTHER INFORMATION: Amino acid residues 27-31 and 57-61 are the
      same and are LeuValPhePheAla in which at least one of residues
      27-31 and the same at least one residues of residues 57-61 are
      substituted with Lys, Asp, or Glu.
<220> FEATURE:

```
<221> NAME/KEY: misc_feature
<222> LOCATION: (57)..(61)
<223> OTHER INFORMATION: Amino acid residues 27-31 and 57-61 are the
      same and are LeuValPhePheAla in which at least one of residues
      27-31 and the same at least one residues of residues 57-61 are
      substituted with Lys, Asp, or Glu.
<220> FEATURE:
<221> NAME/KEY: misc_feature
<222> LOCATION: (71)..(80)
<223> OTHER INFORMATION: Amino acid residues 71-74 are all Lys or all
      Asp. Any one or all of residues 75-80 can either be absent or
      present as Lys or Asp to form, in combination with residues 71-74,
      a C-terminal polylysine or polyaspartate segment of 4 to 10
      residues.

<400> SEQUENCE: 10

Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Glu
            20                  25                  30

Asp Val Gly Ser Asn Lys Gly Ala Asp Ala Glu Phe Arg His Asp Ser
        35                  40                  45

Gly Tyr Glu Val His His Gln Lys Xaa Xaa Xaa Xaa Glu Asp Val
    50                  55                  60

Gly Ser Asn Lys Gly Ala Xaa Xaa Xaa Xaa Xaa Xaa Xaa Xaa Xaa
65                  70                  75                  80

<210> SEQ ID NO 11
<211> LENGTH: 36
<212> TYPE: PRT
<213> ORGANISM: Artificial Sequence
<220> FEATURE:
<223> OTHER INFORMATION: Synthetic

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Lys Lys
            20                  25                  30

Lys Lys Lys Lys
        35

<210> SEQ ID NO 12
<211> LENGTH: 30
<212> TYPE: PRT
<213> ORGANISM: Artificial Sequence
<220> FEATURE:
<223> OTHER INFORMATION: Synthetic

<400> SEQUENCE: 12

Asp Ala Glu Phe Arg His Asp Ser Gly Tyr Glu Val His His Gln Lys
1               5                   10                  15

Leu Glu Glu Phe Ala Glu Asp Val Gly Ser Asn Lys Gly Ala
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Synthetic

<400> SEQUENCE: 13

Asp Ala Glu Phe Arg His Asp Ser Gly Tyr Glu Val His His Gln Lys
1               5                   10                  15
```

```
Leu Asp Asp Phe Ala Glu Asp Val Gly Ser Asn Lys Gly Ala
            20                  25                  30

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Leu Pro Phe Phe Asp
1               5

<210> SEQ ID NO 15
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 either are present,
      together as all Lys or all Asp, or are all absent.  When residues
      7-10 are present then any one or all of residues 1-6 can either
      be absent or present as Lys or Asp to form, in combination with
      residues 7-10, a
<220> FEATURE:
<223> OTHER INFORMATION: N-terminal polylysine or polyaspartate segment
      of 4 to10 residues in length.
<220> FEATURE:
<221> NAME/KEY: misc_feature
<222> LOCATION: (27)..(31)
<223> OTHER INFORMATION: Amino acid residues 27-31 are LeuValPhePheAla
      in which at least one of residues 27-31 are substituted with Pro,
      Gly, or Ser.  The C-terminal Ala residue may be amidated.

<400> SEQUENCE: 15

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala
            35                  40

<210> SEQ ID NO 16
<211> LENGTH: 70
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 are all Lys or all
      Asp, or are all absent. When residues 7-10 are present, then any
      one or all of amino acid residues 1-6 can either be absent or
      present as Lys or Asp to form, in combination with residues 7-10,
      a N-terminal polylysine or
<220> FEATURE:
<223> OTHER INFORMATION: polyaspartate segment of 4 to 10 residues in
      length.
<220> FEATURE:
<221> NAME/KEY: misc_feature
<222> LOCATION: (27)..(31)
<223> OTHER INFORMATION: Amino acid residues 27-31 and 57-61 are the
      same and are LeuValPhePheAla in which at least one of residues
      27-31 and the same at least one residues of residues 57-61 are
      substituted with Pro, Gly, or Ser. The C-terminal Ala residue may
      be amidated.
```

```
<220> FEATURE:
<221> NAME/KEY: misc_feature
<222> LOCATION: (57)..(61)
<223> OTHER INFORMATION: Amino acid residues 27-31 and 57-61 are the
      same and are LeuValPhePheAla in which at least one of residues
      27-31 and the same at least one residues of residues 57-61 are
      substituted with Pro, Gly, or Ser.  The C-terminal Ala residue
      may be amidated.

<400> SEQUENCE: 16

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala Asp Ala Glu Phe Arg His Asp Ser
        35                  40                  45

Gly Tyr Glu Val His His Gln Lys Xaa Xaa Xaa Xaa Xaa Glu Asp Val
    50                  55                  60

Gly Ser Asn Lys Gly Ala
65                  70

<210> SEQ ID NO 17
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(40)
<223> OTHER INFORMATION: Amino acid residues 31-34 are all Lys or all
      Asp or are all absent.  When all residues 31-34 are present, then
      any one or all of residues 35-40 can either be absent or present
      as Lys or Asp to form, in combination with residues 31-34, a
      C-terminal polylysine or
<220> FEATURE:
<223> OTHER INFORMATION: polyaspartate segment of 4 to 10 residues in
      length.
<220> FEATURE:
<221> NAME/KEY: misc_feature
<222> LOCATION: (17)..(27)
<223> OTHER INFORMATION: Amino acid residues 17-21 are LeuValPhePheAla
      in which at least one of residues 17-21 are substituted with Pro,
      Gly, or Ser.

<400> SEQUENCE: 17

Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala Xaa Xaa
            20                  25                  30

Xaa Xaa Xaa Xaa Xaa Xaa Xaa Xaa
        35                  40

<210> SEQ ID NO 18
<211> LENGTH: 70
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (61)..(70)
<223> OTHER INFORMATION: Amino acid residues 61-64 are all Lys or all
      Asp, or are all absent. When all residues 61-64 are present, then
      any one or all of residues 65-70 can either be Lys or Asp to form,
      in combination with residues 61-64, a C-terminal polylysine or
      polyaspartate segment
<220> FEATURE:
<223> OTHER INFORMATION: of 4 to 10 residues in length.
```

```
<220> FEATURE:
<221> NAME/KEY: misc_feature
<222> LOCATION: (17)..(21)
<223> OTHER INFORMATION: Amino acid residues 17-21 and 47-51 are the
      same and are LeuValPhePheAla in which at least one of residues
      17-21 and the same at least one residues of 47-51 are the same
      at least one residues substituted with Pro, Gly, or Ser.
<220> FEATURE:
<221> NAME/KEY: misc_feature
<222> LOCATION: (47)..(51)
<223> OTHER INFORMATION: Amino acid residues 17-21 and 47-51 are the
      same and are LeuValPhePheAla in which at least one of residues
      17-21 and the same at least one residues of 47-51 are the same
      at least one residues substituted with Pro, Gly, or Ser.

<400> SEQUENCE: 18

Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala Asp Ala
                20                  25                  30

Glu Phe Arg His Asp Ser Gly Tyr Glu Val His His Gln Lys Xaa Xaa
            35                  40                  45

Xaa Xaa Xaa Glu Asp Val Gly Ser Asn Lys Gly Ala Xaa Xaa Xaa Xaa
        50                  55                  60

Xaa Xaa Xaa Xaa Xaa Xaa
65                  70

<210> SEQ ID NO 19
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 are all Lys or all
      Asp.  Any one or all of residues 1-6 can either be absent or
      present as Lys or Asp to form, in combination with residues
      7-10, a N-terminal polylysine or polyaspartate segment of 4-10
      residues in length.
<220> FEATURE:
<221> NAME/KEY: misc_feature
<222> LOCATION: (27)..(31)
<223> OTHER INFORMATION: Amino acid residues 27-31 are LeuValPhePheAla
      in which at least one of residues 27-31 are substituted with Pro,
      Gly, or Ser.
<220> FEATURE:
<221> NAME/KEY: misc_feature
<222> LOCATION: (41)..(50)
<223> OTHER INFORMATION: Amino acid residues 41-44 are all Lys or all
      Asp.  Any one or all of residues 45-50 can be either absent or
      present as Lys or Asp to form, in combination with residues 41-44,
      a C-terminal polysine or polyaspartate segment of 4-10 residues.

<400> SEQUENCE: 19

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala Xaa Xaa Xaa Xaa Xaa Xaa Xaa Xaa
            35                  40                  45

Xaa Xaa
    50

<210> SEQ ID NO 20
<211> LENGTH: 80
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: Amino acid residues 7-10 are all Lys or all
      Asp. Any one or all of amino acid residues 1-6 can either be
      absent or present as Lys or Asp to form, in combination with
      residues 7-10, a N-terminal polylysine or polyaspartate segment
      of 4 to 10 residues in length.
<220> FEATURE:
<221> NAME/KEY: misc_feature
<222> LOCATION: (27)..(31)
<223> OTHER INFORMATION: Amino acid residues 27-31 and 57-61 are the
      same and are LeuValPhePheAla in which at least one of residues
      27-31 and the same at least one residues of residues 57-61 are
      substituted with Lys, Asp, or Glu.
<220> FEATURE:
<221> NAME/KEY: misc_feature
<222> LOCATION: (57)..(61)
<223> OTHER INFORMATION: Amino acid residues 27-31 and 57-61 are the
      same and are LeuValPhePheAla in which at least one of residues
      27-31 and the same at least one residues of residues 57-61 are
      substituted with Lys, Asp, or Glu.
<220> FEATURE:
<221> NAME/KEY: misc_feature
<222> LOCATION: (71)..(80)
<223> OTHER INFORMATION: Amino acid residues 71-74 are all Lys or all
      Asp. Any one or all of residues 75-80 can either be absent or
      present as Lys or Asp to form, in combination with residues 71-74,
      a C-terminal polylysine or polyaspartate segment of 4 to 10
      residues.

<400> SEQUENCE: 20

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala Asp Ala Glu Phe Arg His Asp Ser
        35                  40                  45

Gly Tyr Glu Val His His Gln Lys Xaa Xaa Xaa Xaa Xaa Glu Asp Val
    50                  55                  60

Gly Ser Asn Lys Gly Ala Xaa Xaa Xaa Xaa Xaa Xaa Xaa Xaa Xaa Xaa
65                  70                  75                  80

<210> SEQ ID NO 21
<211> LENGTH: 253
<212> TYPE: PRT
<213> ORGANISM: Homo sapiens

<400> SEQUENCE: 21

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
            85                  90                  95

Ser Gln Trp Asn Lys Pro Ser Lys Pro Lys Thr Asn Met Lys His Met
            100                 105                 110
```

```
Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 22
<211> LENGTH: 253
<212> TYPE: PRT
<213> ORGANISM: Gorilla

<400> SEQUENCE: 22

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
```

```
                                      225                 230                 235                 240

Ile Leu Leu Ile Ser Phe Leu Ile Phe Leu Ile Val Gly
                        245                 250

<210> SEQ ID NO 23
<211> LENGTH: 254
<212> TYPE: PRT
<213> ORGANISM: Chimpanzee

<400> SEQUENCE: 23

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
        50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Gln Tyr Ser Ser Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Leu Ile Val Gly
                245                 250

<210> SEQ ID NO 24
<211> LENGTH: 254
<212> TYPE: PRT
<213> ORGANISM: Mus sp.

<400> SEQUENCE: 24

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Thr Trp Gly Gln Pro His Gly Gly Gly Trp
```

```
                  50                  55                  60
Gly Gln Pro His Gly Gly Ser Trp Gly Gln Pro Gly Gly Ser Trp
 65                  70                  75                  80

Gly Gln Pro His Gly Gly Trp Gly Gln Gly Gly Thr His Asn
                 85                  90                  95

Gln Trp Asn Lys Pro Ser Lys Pro Lys Thr Asn Leu Lys His Val Ala
                100                 105                 110

Gly Ala Ala Ala Gly Ala Val Gly Gly Leu Gly Gly Tyr Met
            115                 120                 125

Leu Gly Ser Ala Met Ser Arg Pro Met Ile His Phe Gly Asn Asp Trp
        130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
                195                 200                 205

Val Glu Gln Met Cys Val Thr Gln Tyr Gln Lys Glu Ser Asp Ala Tyr
210                 215                 220

Tyr Asp Gly Arg Arg Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 25
<211> LENGTH: 225
<212> TYPE: PRT
<213> ORGANISM: Rat

<400> SEQUENCE: 25

Gly Gly Trp Asn Thr Gly Gly Ser Arg Tyr Pro Gly Gln Gly Ser Pro
 1               5                  10                  15

Gly Gly Asn Arg Tyr Pro Pro Gln Ser Gly Gly Thr Trp Gly Gln Pro
                20                  25                  30

His Gly Gly Gly Trp Gly Gln Pro His Gly Gly Trp Gly Gln Pro
            35                  40                  45

His Gly Gly Gly Trp Gly Gln Pro His Gly Gly Trp Ser Gln Gly
        50                  55                  60

Gly Gly Thr His Asn Gln Trp Asn Lys Pro Ser Lys Pro Lys Thr Asn
 65                  70                  75                  80

Leu Lys His Val Ala Gly Ala Ala Ala Gly Ala Val Val Gly Gly
                85                  90                  95

Leu Gly Gly Tyr Met Leu Gly Ser Ala Met Ser Arg Pro Met Leu His
                100                 105                 110

Phe Gly Asn Asp Trp Glu Asp Arg Tyr Tyr Arg Glu Asn Met Tyr Arg
            115                 120                 125

Tyr Pro Asn Gln Val Tyr Tyr Arg Pro Val Asp Gln Tyr Ser Asn Gln
        130                 135                 140

Asn Asn Phe Val His Asp Cys Val Asn Ile Thr Ile Lys Gln His Thr
145                 150                 155                 160

Val Thr Thr Thr Thr Lys Gly Glu Asn Phe Thr Glu Thr Asp Val Lys
                165                 170                 175
```

```
Met Met Glu Arg Val Val Glu Gln Met Cys Val Thr Gln Tyr Gln Lys
            180                 185                 190

Glu Ser Gln Ala Tyr Tyr Asp Gly Arg Arg Ser Ser Ala Val Leu Phe
            195                 200                 205

Ser Ser Pro Pro Val Ile Leu Leu Ile Ser Leu Ile Phe Leu Ile Val
        210                 215                 220

Gly
225

<210> SEQ ID NO 26
<211> LENGTH: 254
<212> TYPE: PRT
<213> ORGANISM: Syrian Hamster

<400> SEQUENCE: 26

Met Ala Asn Leu Ser Tyr Trp Leu Leu Ala Leu Phe Val Ala Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
    130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175

His Asp Cys Val Asn Ile Thr Ile Lys Gln His Thr Val Thr Thr Tyr
            180                 185                 190

Thr Lys Gly Glu Asn Phe Thr Glu Thr Asp Ile Lys Ile Met Glu Arg
        195                 200                 205

Val Val Glu Gln Met Cys Thr Thr Gln Tyr Gln Lys Glu Ser Gln Ala
    210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Met Val Gly
                245                 250

<210> SEQ ID NO 27
<211> LENGTH: 258
<212> TYPE: PRT
<213> ORGANISM: Mink

<400> SEQUENCE: 27

Met Val Lys Ser His Ile Gly Ser Trp Leu Leu Val Leu Phe Val Ala
1               5                   10                  15
```

```
Thr Trp Ser Asp Ile Gly Phe Cys Lys Lys Pro Lys Pro Gly Gly
             20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Gly Trp Gly Gln Gly
                 85                  90                  95

Gly Gly Ser His Gly Gln Trp Gly Lys Pro Ser Lys Pro Lys Thr Asn
            100                 105                 110

Met Lys His Val Ala Gly Ala Ala Ala Gly Ala Val Val Gly Gly
            115                 120                 125

Leu Gly Gly Tyr Met Leu Gly Ser Ala Met Ser Arg Pro Leu Ile His
            130                 135                 140

Phe Gly Asn Asp Tyr Glu Asp Arg Tyr Tyr Arg Glu Asn Met Tyr Arg
145                 150                 155                 160

Tyr Pro Asn Gln Val Tyr Tyr Lys Pro Val Asp Gln Tyr Ser Asn Gln
                165                 170                 175

Asn Asn Phe Val His Asp Cys Val Asn Ile Thr Val Lys Gln His Thr
            180                 185                 190

Val Thr Thr Thr Thr Lys Gly Glu Asn Phe Thr Glu Thr Asp Met Lys
            195                 200                 205

Ile Met Glu Arg Val Val Glu Gln Met Cys Val Thr Gln Tyr Gln Arg
210                 215                 220

Glu Ser Glu Ala Ala Tyr Tyr Gln Arg Gly Ala Ser Ala Ile Leu Phe
225                 230                 235                 240

Ser Pro Pro Pro Val Ile Leu Leu Ile Ser Leu Leu Ile Leu Leu Ile
                245                 250                 255

Val Gly

<210> SEQ ID NO 28
<211> LENGTH: 256
<212> TYPE: PRT
<213> ORGANISM: Sheep

<400> SEQUENCE: 28

Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
             20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Gly Trp Gly Gln Gly
                 85                  90                  95

Gly Ser His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125
```

```
Gly Gly Tyr Met Leu Gly Ser Ala Met Ser Arg Pro Leu Ile His Phe
            130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Arg Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
            195                 200                 205

Met Glu Arg Val Val Glu Gln Met Cys Ile Thr Gln Tyr Gln Arg Glu
            210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 29
<211> LENGTH: 256
<212> TYPE: PRT
<213> ORGANISM: Goat

<400> SEQUENCE: 29

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
        50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Ser His Ser Asp Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
            130                 135                 140

Gly His Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser His Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
            195                 200                 205

Met Glu Arg Val Val Glu Gln Met Cys Ile Thr Gln Tyr Gln Arg Glu
            210                 215                 220

Ser Gln Ala Tyr Tyr Gln Arg Gly Ala Ser Val Ile Leu Phe Ser Pro
225                 230                 235                 240

Pro Pro Val Ile Leu Leu Ile Ser Leu Leu Ile Leu Leu Ile Val Gly
                245                 250                 255
```

<210> SEQ ID NO 30
<211> LENGTH: 264
<212> TYPE: PRT
<213> ORGANISM: Cow

<400> SEQUENCE: 30

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260
```

<210> SEQ ID NO 31
<211> LENGTH: 263
<212> TYPE: PRT
<213> ORGANISM: Greater Kudu

<400> SEQUENCE: 31

```
Met Val Lys Ser His Ile Gly Ser Trp Ile Leu Val Leu Phe Val Ala
1               5                   10                  15

Met Trp Ser Asp Val Ala Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Ser Gln Gly Gly Gly Trp Gly Gln Pro His
    50                  55                  60
```

```
Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Lys Thr Asn Met Lys His Val Ala Gly Ala Ala Ala
        115                 120                 125

Gly Ala Val Val Gly Leu Gly Gly Tyr Met Leu Gly Ser Ala Met
    130                 135                 140

Ser Arg Pro Leu Ile His Phe Gly Ser Asp Tyr Glu Asp Arg Tyr Tyr
145                 150                 155                 160

Arg Glu Asn Met Tyr Arg Tyr Pro Asn Gln Val Tyr Tyr Arg Pro Val
                165                 170                 175

Asp Gln Tyr Ser Asn Gln Asn Asn Phe Val His Asp Val Asn Asn Ile
            180                 185                 190

Thr Val Lys Gln His Thr Val Thr Thr Thr Thr Lys Gly Glu Asn Phe
        195                 200                 205

Thr Glu Thr Asp Ile Lys Met Met Glu Arg Val Val Glu Gln Met Cys
210                 215                 220

Ile Thr Gln Tyr Gln Arg Glu Ser Glu Ala Tyr Tyr Gln Arg Gly Ala
225                 230                 235                 240

Ser Val Ile Leu Phe Ser Ser Pro Val Ile Leu Leu Ile Ser Phe
                245                 250                 255

Leu Ile Phe Leu Ile Val Gly
            260

<210> SEQ ID NO 32
<211> LENGTH: 253
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (121)..(122)
<223> OTHER INFORMATION: Amino acid residues 121, 122, 128, 129, and
      130 are Val, Val, Tyr, Met, and Leu, respectively, in which one
      to five of residues 121, 122, 128, 129, and 130, is substituted
      with Pro, Asp, Glu, Lys, Gly, or Ser.
<220> FEATURE:
<221> NAME/KEY: misc_feature
<222> LOCATION: (128)..(130)
<223> OTHER INFORMATION: Amino acid residues 121, 122, 128, 129, and
      130 are Val, Val, Tyr, Met, and Leu, respectively, in which one
      to five of residues 121, 122, 128, 129, and 130 is substituted
      with Pro, Asp, Glu, Lys, Gly, or Ser.

<400> SEQUENCE: 32

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Gly Trp Gly Gln Pro His Gly Gly Gly
    50                  55                  60

Trp Gly Gln Pro His Gly Gly Trp Gly Gln Pro His Gly Gly Gly
65                  70                  75                  80
```

```
Trp Gly Gln Pro His Gly Gly Trp Gly Gln Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Gly Ala Xaa Xaa Gly Gly Leu Gly Gly Xaa
            115                 120                 125

Xaa Xaa Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

<210> SEQ ID NO 33
<211> LENGTH: 264
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (132)..(133)
<223> OTHER INFORMATION: Amino acid residues 132, 133, 139, 140, and 141
      are Val, Val, Tyr, Met, and Leu, respectively, in which one to
      five of residues 132, 133, 139, 140, and 141 is substituted with
      Pro, Asp, Glu, Lys, Gly, or Ser.
<220> FEATURE:
<221> NAME/KEY: misc_feature
<222> LOCATION: (139)..(141)
<223> OTHER INFORMATION: Amino acid residues 132, 133, 139, 140, and 141
      are Val, Val, Tyr, Met, and Leu, respectively, in which one to
      five of residues 132, 133, 139, 140, and 141 is substituted with
      Pro, Asp, Glu, Lys, Gly, or Ser.

<400> SEQUENCE: 33

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
```

```
                   115                 120                 125
Ala Gly Ala Xaa Xaa Gly Gly Leu Gly Gly Xaa Xaa Gly Ser Ala
        130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
                180                 185                 190

Ile Thr Val Lys Glu His Thr Val Thr Thr Thr Thr Lys Gly Glu Asn
                195                 200                 205

Phe Thr Glu Thr Asp Ile Lys Met Met Glu Arg Val Val Glu Gln Met
        210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260
```

<210> SEQ ID NO 34
<211> LENGTH: 65
<212> TYPE: PRT
<213> ORGANISM: human PrP
<220> FEATURE:
<221> NAME/KEY: misc_feature
<222> LOCATION: (1)..(10)
<223> OTHER INFORMATION: Amino acid residues 7-10 either are present,
      together as all Lys or all Asp, or are all absent. When residues
      7-10 are present then any one or all of residues 1-6 can either
      be absent or present as Lys or Asp to form, in combination with
      residues 7-10, a N-
<220> FEATURE:
<223> OTHER INFORMATION: terminal polylysine or polyaspartate segment of
      4 to 10 residues in
<220> FEATURE:
<223> OTHER INFORMATION: length.
<220> FEATURE:
<221> NAME/KEY: misc_feature
<222> LOCATION: (42)..(43)
<223> OTHER INFORMATION: Amino acid residues 42, 43, 49, 50, and 51 are
      Val, Val, Tyr, Met, and Leu, respectively, in which zero or one to
      five of residues 42, 43, 49, 50, and 51 is substituted with Pro,
      Asp, Glu, Lys, Gly, or Ser. The C-terminal Asp residue may be
      amidated.
<220> FEATURE:
<221> NAME/KEY: misc_feature
<222> LOCATION: (49)..(51)
<223> OTHER INFORMATION: Amino acid residues 42, 43, 49, 50, and 51 are
      Val, Val, Tyr, Met, and Leu, respectively, in which zero or one
      to five of residues 42, 43, 49, 50, and 51 is substituted with
      Pro, Asp, Glu, Lys, Gly, or Ser. The C-terminal Asp residue may
      be amidated.

<400> SEQUENCE: 34

```
Xaa Xaa Xaa Xaa Xaa Xaa Xaa Xaa Xaa Xaa Gly Gln Gly Gly Gly Thr
1               5                   10                  15

His Ser Gln Trp Asn Lys Pro Ser Lys Pro Lys Thr Asn Met Lys His
                20                  25                  30

Met Ala Gly Ala Ala Ala Ala Gly Ala Xaa Xaa Gly Gly Leu Gly Gly
            35                  40                  45

Xaa Xaa Xaa Gly Ser Ala Met Ser Arg Pro Ile Ile His Phe Gly Ser
        50                  55                  60

Asp
```

<210> SEQ ID NO 35
<211> LENGTH: 120
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 either are present, together as all Lys or all Asp, or are all absent. When residues 7-10 are present then any one or all of residues 1-6 can either be absent or present as Lys or Asp to form, in combination with residues 7-10, a N-
<220> FEATURE:
<223> OTHER INFORMATION: terminal polylysine or polyaspartate segment of 4 to 10 residues in length.
<220> FEATURE:
<221> NAME/KEY: misc_feature
<222> LOCATION: (42)..(43)
<223> OTHER INFORMATION: Amino acid residues 42, 43, 49, 50, 51 and residues 97, 98, 104, 105, 106 are the same and are Val, Val, Tyr, Met, and Leu, respectively, in which zero or one to five of residues 42, 43, 49, 50, and 51 and the same zero or one to five of residues 97, 98, 104, 105,
<220> FEATURE:
<223> OTHER INFORMATION: and 106 is substituted with Pro, Asp, Glu, Lys, Gly, or Ser.
<220> FEATURE:
<221> NAME/KEY: misc_feature
<222> LOCATION: (49)..(51)
<223> OTHER INFORMATION: Amino acid residues 42, 43, 49, 50, 51 and residues 97, 98, 104, 105, 106 are the same and are Val, Val, Tyr, Met, and Leu, respectively, in which zero or one to five of residues 42, 43, 49, 50, and 51 and the same zero or one to five of residues 97, 98, 104, 105,
<220> FEATURE:
<223> OTHER INFORMATION: and 106 is substituted with Pro, Asp, Glu, Lys, Gly, or Ser.
<220> FEATURE:
<221> NAME/KEY: misc_feature
<222> LOCATION: (97)..(98)
<223> OTHER INFORMATION: Amino acid residues 42, 43, 49, 50, 51 and residues 97, 98, 104, 105, 106 are the same and are Val, Val, Tyr, Met, and Leu, respectively, in which zero or one to five of residues 42, 43, 49, 50, and 51 and the same zero or one to five of residues 97, 98, 104, 105,
<220> FEATURE:
<223> OTHER INFORMATION: and 106 is substituted with Pro, Asp, Glu, Lys, Gly, or Ser.
<220> FEATURE:
<221> NAME/KEY: misc_feature
<222> LOCATION: (104)..(106)
<223> OTHER INFORMATION: Amino acid residues 42, 43, 49, 50, 51 and residues 97, 98, 104, 105, 106 are the same and are Val, Val, Tyr, Met, and Leu, respectively, in which zero or one to five of residues 42, 43, 49, 50, and 51 and the same zero or one to five of residues 97, 98, 104, 105,
<220> FEATURE:
<223> OTHER INFORMATION: and 106 is substituted with Pro, Asp, Glu, Lys, Gly, or Ser.
<220> FEATURE:
<221> NAME/KEY: misc_feature
<223> OTHER INFORMATION: The C-terminal Asp residue may be amidated.

<400> SEQUENCE: 35

Xaa Xaa Xaa Xaa Xaa Xaa Xaa Xaa Xaa Xaa Gly Gln Gly Gly Gly Thr
1               5                   10                  15

His Ser Gln Trp Asn Lys Pro Ser Lys Pro Lys Thr Asn Met Lys His
            20                  25                  30

Met Ala Gly Ala Ala Ala Ala Gly Ala Xaa Xaa Gly Gly Leu Gly Gly
        35                  40                  45

```
Xaa Xaa Xaa Gly Ser Ala Met Ser Arg Pro Ile Ile His Phe Gly Ser
        50                  55                  60

Asp Gly Gln Gly Gly Gly Thr His Ser Gln Trp Asn Lys Pro Ser Lys
 65                  70                  75                  80

Pro Lys Thr Asn Met Lys His Met Ala Gly Ala Ala Ala Ala Gly Ala
                85                  90                  95

Xaa Xaa Gly Gly Leu Gly Gly Xaa Xaa Xaa Gly Ser Ala Met Ser Arg
            100                 105                 110

Pro Ile Ile His Phe Gly Ser Asp
        115                 120

<210> SEQ ID NO 36
<211> LENGTH: 65
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (32)..(33)
<223> OTHER INFORMATION: Amino acid residues 32, 33, 39, 40, and 41 are
      Val, Val, Tyr, Met, and Leu, respectively, in which zero or one to
      five of residues 32, 33, 39, 40, and 41 is substituted with Pro,
      Asp, Glu, Lys, Gly, or Ser.
<220> FEATURE:
<221> NAME/KEY: misc_feature
<222> LOCATION: (39)..(41)
<223> OTHER INFORMATION: Amino acid residues 32, 33, 39, 40, and 41 are
      Val, Val, Tyr, Met, and Leu, respectively, in which zero or one to
      five of residues 32, 33, 39, 40, and 41 is substituted with Pro,
      Asp, Glu, Lys, Gly, or Ser.
<220> FEATURE:
<221> NAME/KEY: misc_feature
<222> LOCATION: (56)..(65)
<223> OTHER INFORMATION: Amino acid residues 56-59 are all Lys or all
      Asp or are all absent. When all residues 56-59 are present, then
      any one or all of the residues 60-65 can either be absent or
      present as Lys or Asp to form, in combination with residues 56-59,
      a C-terminal polylysine
<220> FEATURE:
<223> OTHER INFORMATION: or polyaspartate segment of 4 to 10 residues in
      length.

<400> SEQUENCE: 36

Gly Gln Gly Gly Gly Thr His Ser Gln Trp Asn Lys Pro Ser Lys Pro
 1               5                  10                  15

Lys Thr Asn Met Lys His Met Ala Gly Ala Ala Ala Ala Gly Ala Xaa
                20                  25                  30

Xaa Gly Gly Leu Gly Gly Xaa Xaa Xaa Gly Ser Ala Met Ser Arg Pro
            35                  40                  45

Ile Ile His Phe Gly Ser Asp Xaa Xaa Xaa Xaa Xaa Xaa Xaa Xaa
    50                  55                  60

Xaa
65

<210> SEQ ID NO 37
<211> LENGTH: 120
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (32)..(33)
<223> OTHER INFORMATION: Amino acid residues 32, 33, 39, 40, 41 and
      residues 87, 88, 94, 95, 96 are the same and are Val, Val,
      Tyr, Met, and Leu, respectively, in which zero or one to five of
      residues 32, 33, 39, 40, and 41 and the same zero, one to five of
```

```
              residues 87, 88, 94, 95, and
<220> FEATURE:
<223> OTHER INFORMATION: 96 is substituted with Pro, Asp, Glu, Lys,
      Gly, or Ser.
<220> FEATURE:
<221> NAME/KEY: misc_feature
<222> LOCATION: (39)..(41)
<223> OTHER INFORMATION: Amino acid residues 32, 33, 39, 40, 41 and
      residues 87, 88, 94, 95, 96 are the same and are Val, Val, Tyr,
      Met, and Leu, respectively in which zero or one to five of
      residues 32, 33, 39, 40, and 41 and the same zero, one to five
      of residues 87, 88, 94, 95, and
<220> FEATURE:
<223> OTHER INFORMATION: 96 is substituted with Pro, Asp, Glu, Lys, Gly,
      or Ser.
<220> FEATURE:
<221> NAME/KEY: misc_feature
<222> LOCATION: (87)..(88)
<223> OTHER INFORMATION: Amino acid residues 32, 33, 39, 40, 41 and
      residues 87, 88, 94, 95, 96 are the same and are Val, Val, Tyr,
      Met, and Leu, respectively, in which zero or one to five of
      residues 32, 33, 39, 40, and 41 and the same zero, one to five
      of residues 87, 88, 94, 95, and
<220> FEATURE:
<223> OTHER INFORMATION: 96 is substituted with Pro, Asp, Glu, Lys, Gly,
      or Ser.
<220> FEATURE:
<221> NAME/KEY: misc_feature
<222> LOCATION: (94)..(96)
<223> OTHER INFORMATION: Amino acid residues 32, 33, 39, 40, 41 and
      residues 87, 88, 94, 95, 96 are the same and are Val, Val, Tyr,
      Met, and Leu, respectively, in which zero or one to five of
      residues 32, 33, 39, 40, and 41 and the same zero, one to five
      of residues 87, 88, 94, 95, and
<220> FEATURE:
<223> OTHER INFORMATION: 96 is substituted with Pro, Asp, Glu, Lys, Gly,
      or Ser.
<220> FEATURE:
<221> NAME/KEY: misc_feature
<222> LOCATION: (111)..(120)
<223> OTHER INFORMATION: Amino acid residues 111-114 are all Lys or all
      Asp, or are all absent When all residues 111-114 are present,
      then any one or all of residues 115-120 can either be Lys or Asp
      to form, in combination with residues 111-114, a C-terminal
      polylysine or polyaspartate
<220> FEATURE:
<223> OTHER INFORMATION: segment of 4-10 residues in length.

<400> SEQUENCE: 37

Gly Gln Gly Gly Gly Thr His Ser Gln Trp Asn Lys Pro Ser Lys Pro
1               5                   10                  15

Lys Thr Asn Met Lys His Met Ala Gly Ala Ala Ala Ala Gly Ala Xaa
            20                  25                  30

Xaa Gly Gly Leu Gly Gly Xaa Xaa Xaa Gly Ser Ala Met Ser Arg Pro
        35                  40                  45

Ile Ile His Phe Gly Ser Asp Gly Gln Gly Gly Thr His Ser Gln
    50                  55                  60

Trp Asn Lys Pro Ser Lys Pro Lys Thr Asn Met Lys His Met Ala Gly
65                  70                  75                  80

Ala Ala Ala Ala Gly Ala Xaa Xaa Gly Gly Leu Gly Gly Xaa Xaa Xaa
                85                  90                  95

Gly Ser Ala Met Ser Arg Pro Ile Ile His Phe Gly Ser Asp Xaa Xaa
                100                 105                 110

Xaa Xaa Xaa Xaa Xaa Xaa Xaa Xaa
        115                 120

<210> SEQ ID NO 38
<211> LENGTH: 75
<212> TYPE: PRT
<213> ORGANISM: Artificial Sequence
```

```
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 are all Lys or all
      Asp.  Any one or all of residues 1-6 can either be absent or
      present as Lys or Asp to form, in combination with residues
      7-10, a N-terminal polylysine or polyaspartate segment of 4 to
      10 residues in length.
<220> FEATURE:
<221> NAME/KEY: misc_feature
<222> LOCATION: (42)..(43)
<223> OTHER INFORMATION: Amino acid residues 42, 43, 49, 50, and 51 are
      Val, Val, Tyr, Met, and Leu, respectively, in which zero or one to
      five of residues 42, 43, 49, 50, and 51 is substituted with Pro,
      Asp, Glu, Lys, Gly or Ser.
<220> FEATURE:
<221> NAME/KEY: misc_feature
<222> LOCATION: (49)..(51)
<223> OTHER INFORMATION: Amino acid residues 42, 43, 49, 50, and 51 are
      Val, Val, Tyr, Met, and Leu, respectively, in which zero or one to
      five of residues 42, 43, 49, 50, and 51 is substituted with Pro,
      Asp, Glu, Lys, Gly, or Ser.
<220> FEATURE:
<221> NAME/KEY: misc_feature
<222> LOCATION: (66)..(75)
<223> OTHER INFORMATION: Amino acids 66-69 are all Lys or all Asp.  Any
      one or all of residues 70-75 can either be absent or present as
      Lys or Asp to form, in combination with residues 66-69, a
      C-terminal polylysine or polyaspartate segment of 4 to 10 residues
      in length.

<400> SEQUENCE: 38

Xaa Xaa Xaa Xaa Xaa Xaa Xaa Xaa Xaa Xaa Gly Gln Gly Gly Gly Thr
1               5                   10                  15

His Ser Gln Trp Asn Lys Pro Ser Lys Pro Lys Thr Asn Met Lys His
            20                  25                  30

Met Ala Gly Ala Ala Ala Ala Gly Ala Xaa Xaa Gly Gly Leu Gly Gly
        35                  40                  45

Xaa Xaa Xaa Gly Ser Ala Met Ser Arg Pro Ile Ile His Phe Gly Ser
    50                  55                  60

Asp Xaa Xaa Xaa Xaa Xaa Xaa Xaa Xaa Xaa Xaa
65                  70                  75

<210> SEQ ID NO 39
<211> LENGTH: 130
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 are all Lys or all
      Asp.  Any one or all of residues 1-6 can either be absent or
      present as Lys or Asp to form, in combination with residues
      7-10, a N-terminal polylysine or polyaspartate segment of 4 to
      10 residues in length.
<220> FEATURE:
<221> NAME/KEY: misc_feature
<222> LOCATION: (42)..(43)
<223> OTHER INFORMATION: Amino acid residues 42, 43, 49, 50, 51 and
      residues 97, 98, 104, 105, 106 are the same and are Val, Val,
      Tyr, Met, and Leu, respectively, in which zero or one to five of
      residues 42, 43, 49, 50, and 51 and the same zero or one to five
      of residues 97, 98, 104, 105,
<220> FEATURE:
<223> OTHER INFORMATION: and 106 is substituted with Pro, Asp, Glu, Lys,
      Gly, or Ser.
<220> FEATURE:
<221> NAME/KEY: misc_feature
<222> LOCATION: (49)..(51)
```

US 7,479,482 B2

107

108

-continued

```
<223> OTHER INFORMATION: Amino acid residues 42, 43, 49, 50, 51 and
      residues 97, 98, 104, 105, 106 are the same and are Val, Val, Tyr,
      Met, and Leu, respectively, in which zero or one to five of
      residues 42, 43, 49, 50, and 51 and the same zero or one to five
      of residues 97, 98, 104, 105,
<220> FEATURE:
<223> OTHER INFORMATION: and 106 is substituted with Pro, Asp, Glu, Lys,
      Gly, or Ser.
<220> FEATURE:
<221> NAME/KEY: misc_feature
<222> LOCATION: (97)..(98)
<223> OTHER INFORMATION: Amino acid residues 42, 43, 49, 50, 51 and
      residues 97, 98, 104, 105, 106 are the same and are Val, Val,
      Tyr, Met, and Leu, respectively, in which zero or one to five of
      residues 42, 43, 49, 50, and 51 and the same zero or one to five
      of residues 97, 98, 104, 105,
<220> FEATURE:
<223> OTHER INFORMATION: and 106 is substituted with Pro, Asp, Glu, Lys,
      Gly, or Ser.
<220> FEATURE:
<221> NAME/KEY: misc_feature
<222> LOCATION: (104)..(106)
<223> OTHER INFORMATION: Amino acid residues 42, 43, 49, 50, 51 and
      residues 97, 98, 104, 105, 106 are the same and are Val, Val, Tyr,
      Met, and Leu, respectively, in which zero or one to five of
      residues 42, 43, 49, 50, and 51 and the same zero or one to five
      of residues 97, 98, 104, 105,
<220> FEATURE:
<223> OTHER INFORMATION: and 106 is substituted with Pro, Asp, Glu, Lys,
      Gly, or Ser.
<220> FEATURE:
<221> NAME/KEY: misc_feature
<222> LOCATION: (121)..(130)
<223> OTHER INFORMATION: Amino acids 121-124 are all Lys or all Asp.
      Any one or all of residues 125-130 can either be absent or
      present as Lys or Asp to form, in combination with residues
      121-124, a C-terminal polylysine or polyaspartate segment of 4 to
      10 residues in length.

<400> SEQUENCE: 39

Xaa Xaa Xaa Xaa Xaa Xaa Xaa Xaa Xaa Xaa Gly Gln Gly Gly Gly Thr
1               5                   10                  15

His Ser Gln Trp Asn Lys Pro Ser Lys Pro Lys Thr Asn Met Lys His
            20                  25                  30

Met Ala Gly Ala Ala Ala Ala Gly Ala Xaa Xaa Gly Gly Leu Gly Gly
        35                  40                  45

Xaa Xaa Xaa Gly Ser Ala Met Ser Arg Pro Ile Ile His Phe Gly Ser
    50                  55                  60

Asp Gly Gln Gly Gly Gly Thr His Ser Gln Trp Asn Lys Pro Ser Lys
65                  70                  75                  80

Pro Lys Thr Asn Met Lys His Met Ala Gly Ala Ala Ala Ala Gly Ala
                85                  90                  95

Xaa Xaa Gly Gly Leu Gly Gly Xaa Xaa Xaa Gly Ser Ala Met Ser Arg
            100                 105                 110

Pro Ile Ile His Phe Gly Ser Asp Xaa Xaa Xaa Xaa Xaa Xaa Xaa Xaa
        115                 120                 125

Xaa Xaa
    130

<210> SEQ ID NO 40
<211> LENGTH: 73
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 either are present,
``` together as all Lys or all Asp, or are all absent. When residues
7-10 are present then any one or all of residues 1-6 can either be
absent or present as Lys or Asp to form, in combination with
residues 7-10, a N-
<220> FEATURE:
<223> OTHER INFORMATION: terrminal polylysine or polyaspartate segment
of 4 to10 residues in length.
<220> FEATURE:
<221> NAME/KEY: misc_feature
<222> LOCATION: (50)..(51)
<223> OTHER INFORMATION: Amino acid residues 50, 51, 57, 58, and 59 are
Val, Val, Tyr, Met, and Leu, respectively, in which zero or one
to five of residues 50, 51, 57, 58, and 59 is substituted with
Pro, Asp, Glu, Lys, Gly, or Ser. The C-terminal Asp residue
may be amidated.
<220> FEATURE:
<221> NAME/KEY: misc_feature
<222> LOCATION: (57)..(59)
<223> OTHER INFORMATION: Amino acid residues 50, 51, 57, 58, and 59
are Val, Val, Tyr, Met, and Leu, respectively, in which zero or
one to five of residues 50, 51, 57, 58, and 59 is substituted
with Pro, Asp, Glu, Lys, Gly, or Ser. The C-terminal Asp residue
may be amidated.

<400> SEQUENCE: 40

Xaa Xaa Xaa Xaa Xaa Xaa Xaa Xaa Xaa Xaa Gly Gln Pro His Gly Gly
1               5                   10                  15

Gly Gly Trp Gly Gln Gly Gly Thr His Gly Gln Trp Asn Lys Pro Ser
            20                  25                  30

Lys Pro Lys Thr Asn Met Lys His Val Ala Gly Ala Ala Ala Ala Gly
        35                  40                  45

Ala Xaa Xaa Gly Gly Leu Gly Gly Xaa Xaa Xaa Gly Ser Ala Met Ser
    50                  55                  60

Arg Pro Leu Ile His Phe Gly Asn Asp
65                  70

<210> SEQ ID NO 41
<211> LENGTH: 136
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 either are present,
together as all Lys or all Asp, or are all absent. When residues
7-10 are present then any one or all of residues 1-6 can either
be absent or present as Lys or Asp to form, in combination with
residues 7-10, a N-
<220> FEATURE:
<223> OTHER INFORMATION: terrminal polylysine or polyaspartate segment
of 4 to10 residues in length.
<220> FEATURE:
<221> NAME/KEY: misc_feature
<222> LOCATION: (50)..(51)
<223> OTHER INFORMATION: Amino acid residues 50, 51, 57, 58, 59 and
residues 113, 114, 120, 121, 122 are the same and are Val, Val,
Tyr, Met, and Leu, respectively, in which zero or one to five of
residues 50, 51, 57, 58, 59 and the same zero or one to five of
residues 113, 114, 120, 121,
<220> FEATURE:
<223> OTHER INFORMATION: 122 is substituted with Pro, Asp, Glu, Lys,
Gly, or Ser.
<220> FEATURE:
<221> NAME/KEY: misc_feature
<222> LOCATION: (57)..(59)
<223> OTHER INFORMATION: Amino acid residues 50, 51, 57, 58, 59 and
residues 113, 114, 120, 121, 122 are the same and are Val, Val,
Tyr, Met, and Leu, respectively, in which zero or one to five of
residues 50, 51, 57, 58, 59 and the same zero or one to five of
residues 113, 114, 120, 121,
<220> FEATURE:

```
<223> OTHER INFORMATION: 122 is substituted with Pro, Asp, Glu, Lys,
      Gly, or Ser.
<220> FEATURE:
<221> NAME/KEY: misc_feature
<222> LOCATION: (113)..(114)
<223> OTHER INFORMATION: Amino acid residues 50, 51, 57, 58, 59 and
      residues 113, 114, 120, 121, 122 are the same and are Val, Val,
      Tyr, Met, and Leu, respectively, in which zero or one to five of
      residues 50, 51, 57, 58, 59 and the same zero or one to five of
      residues 113, 114, 120, 121,
<220> FEATURE:
<223> OTHER INFORMATION: 122 is substituted with Pro, Asp, Glu, Lys,
      Gly, or Ser.
<220> FEATURE:
<221> NAME/KEY: misc_feature
<222> LOCATION: (120)..(122)
<223> OTHER INFORMATION: Amino acid residues 50, 51, 57, 58, 59 and
      residues 113, 114, 120, 121, 122 are the same and are Val, Val,
      Tyr, Met, and Leu, respectively, in which zero or one to five of
      residues 50, 51, 57, 58, 59 and the same zero or one to five of
      residues 113, 114, 120, 121,
<220> FEATURE:
<223> OTHER INFORMATION: 122 is substituted with Pro, Asp, Glu, Lys,
      Gly, or Ser.
<220> FEATURE:
<221> NAME/KEY: misc_feature
<223> OTHER INFORMATION: The C-terminal Asp residue may be amidated.

<400> SEQUENCE: 41

Xaa Xaa Xaa Xaa Xaa Xaa Xaa Xaa Xaa Gly Gln Pro His Gly Gly
1               5                   10                  15

Gly Gly Trp Gly Gln Gly Gly Thr His Gly Gln Trp Asn Lys Pro Ser
            20                  25                  30

Lys Pro Lys Thr Asn Met Lys His Val Ala Gly Ala Ala Ala Ala Gly
        35                  40                  45

Ala Xaa Xaa Gly Gly Leu Gly Gly Xaa Xaa Xaa Gly Ser Ala Met Ser
    50                  55                  60

Arg Pro Leu Ile His Phe Gly Asn Asp Gly Gln Pro His Gly Gly
65                  70                  75                  80

Gly Trp Gly Gln Gly Gly Thr His Gly Gln Trp Asn Lys Pro Ser Lys
                85                  90                  95

Pro Lys Thr Asn Met Lys His Val Ala Gly Ala Ala Ala Ala Gly Ala
            100                 105                 110

Xaa Xaa Gly Gly Leu Gly Gly Xaa Xaa Xaa Gly Ser Ala Met Ser Arg
        115                 120                 125

Pro Leu Ile His Phe Gly Asn Asp
    130                 135

<210> SEQ ID NO 42
<211> LENGTH: 73
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (40)..(41)
<223> OTHER INFORMATION: Amino acid residues 40, 41, 47, 48, and 49 are
      Val, Val, Tyr, Met, and Leu, respectively, in which zero or one to
      five of residues 40, 41, 47, 48, and 49 is substituted with Pro,
      Asp, Glu, Lys, Gly, or Ser.
<220> FEATURE:
<221> NAME/KEY: misc_feature
<222> LOCATION: (47)..(49)
<223> OTHER INFORMATION: Amino acid residues 40, 41, 47, 48, and 49 are
      Val, Val, Tyr, Met, and Leu, respectively, in which zero or one
      to five of residues 40, 41, 47, 48, and 49 is substituted with
      Pro, Asp, Glu, Lys, Gly, or Ser.
<220> FEATURE:
```

```
<221> NAME/KEY: misc_feature
<222> LOCATION: (64)..(73)
<223> OTHER INFORMATION: Amino acid residues 64-67 are all Lys or all
      Asp, or are all absent. When all residues 64-67 are present, then
      any one or all of residues 68-73 can either be absent or present
      as Lys or Asp to form, in combination with residues 64-67, a
      C-terminal polylysine
<220> FEATURE:
<223> OTHER INFORMATION: or polyaspartate segment of 4 to 10 residues in
      length.

<400> SEQUENCE: 42

Gly Gln Pro His Gly Gly Gly Trp Gly Gln Gly Gly Thr His Gly
1               5                   10                  15

Gln Trp Asn Lys Pro Ser Lys Pro Lys Thr Asn Met Lys His Val Ala
            20                  25                  30

Gly Ala Ala Ala Ala Gly Ala Xaa Xaa Gly Gly Leu Gly Gly Xaa Xaa
            35                  40                  45

Xaa Gly Ser Ala Met Ser Arg Pro Leu Ile His Phe Gly Asn Asp Xaa
        50                  55                  60

Xaa Xaa Xaa Xaa Xaa Xaa Xaa Xaa Xaa
65                  70

<210> SEQ ID NO 43
<211> LENGTH: 136
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (40)..(41)
<223> OTHER INFORMATION: Amino acid residues 40, 41, 47, 48, 49 and
      residues 103, 104, 110, 111, 112 are the same and are Val, Val,
      Tyr, Met, and Leu, respectively in which zero or one to five of
      residues 40, 41, 47, 48, and 49 and the same zero or one to five
      of residues 103, 104, 110,
<220> FEATURE:
<223> OTHER INFORMATION: 111, and 112 is substituted with Pro, Asp, Glu,
      Lys, Gly, or Ser.
<220> FEATURE:
<221> NAME/KEY: misc_feature
<222> LOCATION: (47)..(49)
<223> OTHER INFORMATION: Amino acid residues 40, 41, 47, 48, 49 and
      residues 103, 104, 110, 111, 112 are the same and are Val, Val,
      Tyr, Met, and Leu, respectively in which zero or one to five of
      residues 40, 41, 47, 48, and 49 and the same zero or one to five
      of residues 103, 104, 110,
<220> FEATURE:
<223> OTHER INFORMATION: 111, and 112 is substituted with Pro, Asp, Glu,
      Lys, Gly, or Ser.
<220> FEATURE:
<221> NAME/KEY: misc_feature
<222> LOCATION: (103)..(104)
<223> OTHER INFORMATION: Amino acid residues 40, 41, 47, 48, 49 and
      residues 103, 104, 110, 111, 112 are the same and are Val, Val,
      Tyr, Met, and Leu, respectively in which zero or one to five of
      residues 40, 41, 47, 48, and 49 and the same zero or one to five
      of residues 103, 104, 110,
<220> FEATURE:
<223> OTHER INFORMATION: 111, and 112 is substituted with Pro, Asp, Glu,
      Lys, Gly, or Ser.
<220> FEATURE:
<221> NAME/KEY: misc_feature
<222> LOCATION: (110)..(112)
<223> OTHER INFORMATION: Amino acid residues 40, 41, 47, 48, 49 and
      residues 103, 104, 110, 111, 112 are the same and are Val, Val,
      Tyr, Met, and Leu, respectively in which zero or one to five of
      residues 40, 41, 47, 48, and 49 and the same zero or one to five
      of residues 103, 104, 110,
<220> FEATURE:
<223> OTHER INFORMATION: 111, and 112 is substituted with Pro, Asp, Glu,
      Lys, Gly, or Ser.
```

```
<220> FEATURE:
<221> NAME/KEY: misc_feature
<222> LOCATION: (127)..(136)
<223> OTHER INFORMATION: Amino acid residues 127-130 are all Lys or all
      Asp, or are all absent. When all residues 127-130 are present,
      then any one or all of residues 131-136 can either be Lys or Asp
      to form, in combination with residues 127-130, a C-terminal
      polylysine or polyaspartate
<220> FEATURE:
<223> OTHER INFORMATION: segment of 4 to 10 residues in length.

<400> SEQUENCE: 43

Gly Gln Pro His Gly Gly Gly Trp Gly Gln Gly Gly Thr His Gly
1               5                   10                  15

Gln Trp Asn Lys Pro Ser Lys Pro Lys Thr Asn Met Lys His Val Ala
            20                  25                  30

Gly Ala Ala Ala Gly Ala Xaa Xaa Gly Gly Leu Gly Gly Xaa Xaa
            35                  40                  45

Xaa Gly Ser Ala Met Ser Arg Pro Leu Ile His Phe Gly Asn Asp Gly
    50                  55                  60

Gln Pro His Gly Gly Gly Trp Gly Gln Gly Gly Thr His Gly Gln
65              70                  75                  80

Trp Asn Lys Pro Ser Lys Pro Lys Thr Asn Met Lys His Val Ala Gly
                85                  90                  95

Ala Ala Ala Gly Ala Xaa Xaa Gly Gly Leu Gly Gly Xaa Xaa Xaa
            100                 105                 110

Gly Ser Ala Met Ser Arg Pro Leu Ile His Phe Gly Asn Asp Xaa Xaa
        115                 120                 125

Xaa Xaa Xaa Xaa Xaa Xaa Xaa Xaa
    130                 135

<210> SEQ ID NO 44
<211> LENGTH: 83
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 are all Lys or all
      Asp. Any one or all of residues 1-6 can either be absent or
      present as Lys or Asp to form, in combination with residues
      7-10, a N-terminal polylysine or polyaspartate segment of 4 to
      10 residues in length.
<220> FEATURE:
<221> NAME/KEY: misc_feature
<222> LOCATION: (50)..(51)
<223> OTHER INFORMATION: Amino acid residues 50, 51, 57, 58 and 59 are
      Val, Val, Tyr, Met, and Leu, respectively, in which zero or one to
      five of residues 50, 51, 57, 58, and 59 is substituted with Pro,
      Asp, Glu, Lys, Gly, or Ser. The C-terminal Asp residue may be
      amidated.
<220> FEATURE:
<221> NAME/KEY: misc_feature
<222> LOCATION: (57)..(59)
<223> OTHER INFORMATION: Amino acid residues 50, 51, 57, 58 and 59 are
      Val, Val, Tyr, Met, and Leu, respectively, in which zero or one to
      five of residues 50, 51, 57, 58, and 59 is substituted with Pro,
      Asp, Glu, Lys, Gly, or Ser. The C-terminal Asp residue may be
      amidated.
<220> FEATURE:
<221> NAME/KEY: misc_feature
<222> LOCATION: (74)..(83)
<223> OTHER INFORMATION: Amino acids 74-77 are all Lys or all Asp. Any
      one or all of 78-83 can either be absent or present as Lys or Asp
      to form, in combination with residues 74-77, a C-terminal
      polylysine or polyaspartate segment of 4 to 10 residues in length.
```

```
<400> SEQUENCE: 44

Xaa Xaa Xaa Xaa Xaa Xaa Xaa Xaa Xaa Xaa Gly Gln Pro His Gly Gly
1               5                   10                  15

Gly Gly Trp Gly Gln Gly Gly Thr His Gly Gln Trp Asn Lys Pro Ser
            20                  25                  30

Lys Pro Lys Thr Asn Met Lys His Val Ala Gly Ala Ala Ala Ala Gly
        35                  40                  45

Ala Xaa Xaa Gly Gly Leu Gly Gly Xaa Xaa Xaa Gly Ser Ala Met Ser
    50                  55                  60

Arg Pro Leu Ile His Phe Gly Asn Asp Xaa Xaa Xaa Xaa Xaa Xaa
65                  70                  75                  80

Xaa Xaa Xaa

<210> SEQ ID NO 45
<211> LENGTH: 146
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 are all Lys or all
      Asp. Any one or all of residues 1-6 can either be absent or
      present as Lys or Asp to form, in combination with residues 7-10,
      a N-terminal polylysine or polyaspartate segment of 4 to 10
      residues in length.
<220> FEATURE:
<221> NAME/KEY: misc_feature
<222> LOCATION: (50)..(51)
<223> OTHER INFORMATION: Amino acid residues 50, 51, 57, 58, 59 and
      residues 113, 114, 120, 121, 122 are the same and are Val, Val,
      Tyr, Met, and Leu, respectively, in which zero or one to five of
      residues 50, 51, 57, 58, and 59 and the same zero or one to five
      of residues 113, 114, 120,
<220> FEATURE:
<223> OTHER INFORMATION: 121, and 122 is substituted with Pro, Asp, Glu,
      Lys, Gly or Ser.
<220> FEATURE:
<221> NAME/KEY: misc_feature
<222> LOCATION: (57)..(59)
<223> OTHER INFORMATION: Amino acid residues 50, 51, 57, 58, 59 and
      residues 113, 114, 120, 121, 122 are the same and are Val, Val,
      Tyr, Met, and Leu, respectively, in which zero or one to five of
      residues 50, 51, 57, 58, and 59 and the same zero or one to five
      of residues 113, 114, 120,
<220> FEATURE:
<223> OTHER INFORMATION: 121, and 122 is substituted with Pro, Asp, Glu,
      Lys, Gly or Ser.
<220> FEATURE:
<221> NAME/KEY: misc_feature
<222> LOCATION: (113)..(114)
<223> OTHER INFORMATION: Amino acid residues 50, 51, 57, 58, 59 and
      residues 113, 114, 120, 121, 122 are the same and are Val, Val,
      Tyr, Met, and Leu, respectively, in which zero or one to five of
      residues 50, 51, 57, 58, and 59 and the same zero or one to five
      of residues 113, 114, 120,
<220> FEATURE:
<223> OTHER INFORMATION: 121, and 122 is substituted with Pro, Asp,
      Glu, Lys, Gly or Ser.
<220> FEATURE:
<221> NAME/KEY: misc_feature
<222> LOCATION: (120)..(122)
<223> OTHER INFORMATION: Amino acid residues 50, 51, 57, 58, 59 and
      residues 113, 114, 120, 121, 122 are the same and are Val, Val,
      Tyr, Met, and Leu, respectively, in which zero or one to five of
      residues 50, 51, 57, 58,
      and 59 and the same zero or one to five of residues 113, 114, 120,
<220> FEATURE:
<223> OTHER INFORMATION: 121, and 122 is substituted with Pro, Asp, Glu,
      Lys, Gly or Ser.
<220> FEATURE:
```

```
<221> NAME/KEY: misc_feature
<222> LOCATION: (137)..(146)
<223> OTHER INFORMATION: Amino acids 137-140 are all Lys or all Asp.
      Any one or all of residues 140-146 can either be absent or present
      as Lys or Asp to form, in combination with residues 137-140, a
      C-terminal polylysine or polyaspartate segment of 4 to 10 residues
      in length.

<400> SEQUENCE: 45

Xaa Xaa Xaa Xaa Xaa Xaa Xaa Xaa Xaa Xaa Gly Gln Pro His Gly Gly
1               5                   10                  15

Gly Gly Trp Gly Gln Gly Gly Thr His Gly Gln Trp Asn Lys Pro Ser
            20                  25                  30

Lys Pro Lys Thr Asn Met Lys His Val Ala Gly Ala Ala Ala Ala Gly
        35                  40                  45

Ala Xaa Xaa Gly Gly Leu Gly Gly Xaa Xaa Xaa Gly Ser Ala Met Ser
    50                  55                  60

Arg Pro Leu Ile His Phe Gly Asn Asp Gly Gln Pro His Gly Gly Gly
65                  70                  75                  80

Gly Trp Gly Gln Gly Gly Thr His Gly Gln Trp Asn Lys Pro Ser Lys
            85                  90                  95

Pro Lys Thr Asn Met Lys His Val Ala Gly Ala Ala Ala Ala Gly Ala
        100                 105                 110

Xaa Xaa Gly Gly Leu Gly Gly Xaa Xaa Xaa Gly Ser Ala Met Ser Arg
    115                 120                 125

Pro Leu Ile His Phe Gly Asn Asp Xaa Xaa Xaa Xaa Xaa Xaa Xaa Xaa
130                 135                 140

Xaa Xaa
145

<210> SEQ ID NO 46
<211> LENGTH: 37
<212> TYPE: PRT
<213> ORGANISM: Homo sapiens

<400> SEQUENCE: 46

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 47
<211> LENGTH: 36
<212> TYPE: PRT
<213> ORGANISM: Mus sp.

<400> SEQUENCE: 47

Lys Cys Asn Thr Ala Thr Cys Ala Thr Gln Arg Leu Ala Asn Phe Val
1               5                   10                  15

Arg Ser Ser Asn Asn Leu Gly Pro Val Leu Pro Pro Thr Asn Val Gly
            20                  25                  30

Ser Asn Thr Tyr
        35

<210> SEQ ID NO 48
<211> LENGTH: 47
<212> TYPE: PRT
<213> ORGANISM: Artificial Sequence
```

```
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 either are present,
      together as all Lys or all Asp, or are all absent. When residues
      7-10 are present then any one or all of residues 1-6 can either be
      absent or present as Lys or Asp to form, in combination with
      residues 7-10, a N-
<220> FEATURE:
<223> OTHER INFORMATION: terminal polylysine or polyaspartate segment of
      4 to10 residues in length.
<220> FEATURE:
<221> NAME/KEY: misc_feature
<222> LOCATION: (33)..(33)
<223> OTHER INFORMATION: Amino acid residues 33, 36, and 37 are Phe, Ile
      and Leu, respectively, in which zero, one, two, or three of
      residues 33, 36 and 37 is substituted with Pro, Asp, Glu, Lys,
      Gly, or Ser.
<220> FEATURE:
<221> NAME/KEY: misc_feature
<222> LOCATION: (36)..(37)
<223> OTHER INFORMATION: Amino acid residues 33, 36, and 37 are Phe, Ile
      and Leu, respectively, in which zero, one, two, or three of
      residues 33, 36 and 37 is substituted with Pro, Asp, Glu, Lys,
      Gly, or Ser.

<400> SEQUENCE: 48

Xaa Xaa Xaa Xaa Xaa Xaa Xaa Xaa Xaa Xaa Lys Cys Asn Thr Ala Thr
1               5                   10                  15

Cys Ala Thr Gln Arg Leu Ala Asn Phe Leu Val His Ser Ser Asn Asn
            20                  25                  30

Xaa Gly Ala Xaa Xaa Ser Ser Thr Asn Val Gly Ser Asn Thr Tyr
        35                  40                  45

<210> SEQ ID NO 49
<211> LENGTH: 84
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 either are present,
      together as all Lys or all Asp, or are all absent. When residues
      7-10 are present then any one or all of residues 1-6 can either be
      absent or present as Lys or Asp to form, in combination with
      residues 7-10, a N-
<220> FEATURE:
<223> OTHER INFORMATION: terrminal polylysine or polyaspartate segment
      of 4 to 10 residues in length.
<220> FEATURE:
<221> NAME/KEY: misc_feature
<222> LOCATION: (33)..(33)
<223> OTHER INFORMATION: Amino acid residues 33, 36, 37 and residues 70,
      73, 74 are the same and are Phe, Ile, and Leu, respectively, in
      which zero, one, two, or three of residues 33, 36, and 37 and the
      same zero, one, two, or three of residues 70, 73, 74 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (36)..(37)
<223> OTHER INFORMATION: Amino acid residues 33, 36, 37 and residues
      70, 73, 74 are the same and are Phe, Ile, and Leu, respectively,
      in which zero, one, two, or three of residues 33, 36, and 37 and
      the same zero, one, two, or three of residues 70, 73, 74 is
      substituted with Pro, Asp,
<220> FEATURE:
<223> OTHER INFORMATION: Glu, Lys, Gly, or Ser.
<220> FEATURE:
<221> NAME/KEY: misc_feature
```

```
<222> LOCATION: (70)..(70)
<223> OTHER INFORMATION: Amino acid residues 33, 36, 37 and residues
      70, 73, 74 are the same and are Phe, Ile, and Leu, respectively,
      in which zero, one, two, or three of residues 33, 36, and 37 and
      the same zero, one, two, or three of residues 70, 73, 74 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (73)..(74)
<223> OTHER INFORMATION: Amino acid residues 33, 36, 37 and residues
      70, 73, 74 are the same and are Phe, Ile, and Leu, respectively,
      in which zero, one, two, or three of residues 33, 36, and 37 and
      the same zero, one, two, or three of residues 70, 73, 74 is
      substituted with Pro, Asp,
<220> FEATURE:
<223> OTHER INFORMATION: Glu, Lys, Gly, or Ser.

<400> SEQUENCE: 49

Xaa Xaa Xaa Xaa Xaa Xaa Xaa Xaa Xaa Xaa Lys Cys Asn Thr Ala Thr
1               5                   10                  15

Cys Ala Thr Gln Arg Leu Ala Asn Phe Leu Val His Ser Ser Asn Asn
            20                  25                  30

Xaa Gly Ala Xaa Xaa Ser Ser Thr Asn Val Gly Ser Thr Tyr Lys
        35                  40                  45

Cys Asn Thr Ala Thr Cys Ala Thr Gln Arg Leu Ala Asn Phe Leu Val
    50                  55                  60

His Ser Ser Asn Asn Xaa Gly Ala Xaa Xaa Ser Ser Thr Asn Val Gly
65                  70                  75                  80

Ser Asn Thr Tyr

<210> SEQ ID NO 50
<211> LENGTH: 47
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: Amino acid residues 23, 26, and 27 are Phe,
      Ile, and Leu, respectively, in which zero, one, two or three of
      residues 23, 26, and 27 is substituted with Pro, Asp, Glu, Lys,
      Gly, or Ser.
<220> FEATURE:
<221> NAME/KEY: misc_feature
<222> LOCATION: (26)..(27)
<223> OTHER INFORMATION: Amino acid residues 23, 26, and 27 are Phe,
      Ile, and Leu, respectively, in which zero, one, two or three of
      residues 23, 26, and 27 is substituted with Pro, Asp, Glu, Lys,
      Gly, or Ser.
<220> FEATURE:
<221> NAME/KEY: misc_feature
<222> LOCATION: (38)..(47)
<223> OTHER INFORMATION: Amino acid residues 38-41 are all Lys or all
      Asp, or are all absent. When all residues 38-41 are present, then
      any one or all of residues 42-47 can either be absent or present
      as Lys or Asp to form, in combination with residues 38-41, a
      C-terminal polylysine
<220> FEATURE:
<223> OTHER INFORMATION: or polyaspartate segment of 4 to 10 residues
      in length.

<400> SEQUENCE: 50

Lys Cys Asn Thr Ala Thr Cys Ala Thr Gln Arg Leu Ala Asn Phe Leu
1               5                   10                  15

Val His Ser Ser Asn Asn Xaa Gly Ala Xaa Xaa Ser Ser Thr Asn Val
            20                  25                  30
```

-continued

Gly Ser Asn Thr Tyr Xaa Xaa Xaa Xaa Xaa Xaa Xaa Xaa Xaa
            35                  40                  45

<210> SEQ ID NO 51
<211> LENGTH: 84
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: Amino acid residues 23, 26, 27 and residues 60,
      63, 64 are the same and are Phe, Ile, and Leu, respectively, in
      which zero, one, two, or of residues 23, 26, and 27 and the same
      zero, one, two or three of residues 60, 63, 64 is substituted with
      Pro, Asp,
<220> FEATURE:
<223> OTHER INFORMATION: Glu, Lys, Gly, or Ser.
<220> FEATURE:
<221> NAME/KEY: misc_feature
<222> LOCATION: (26)..(27)
<223> OTHER INFORMATION: Amino acid residues 23, 26, 27 and residues 60,
      63, 64 are the same and are Phe, Ile, and Leu, respectively, in
      which zero, one, two, or three of residues 23, 26, and 27 and the
      same zero, one, two, or three of residues 60, 63, 64 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (60)..(60)
<223> OTHER INFORMATION: Amino acid residues 23, 26, 27 and residues 60,
      63, 64 are the same and are Phe, Ile, and Leu, respectively, in
      which zero, one, two, or three of residues 23, 26, and 27 and the
      same zero, one, two, or three of residues 60, 63, 64 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (63)..(64)
<223> OTHER INFORMATION: Amino acid residues 23, 26, 27 and residues 60,
      63, 64 are the same and are Phe, Ile, and Leu, respectively, in
      which zero, one, two, or three of residues 23, 26, and 27 and
      the same zero, one, two, or three of residues 60, 63, 64 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (75)..(84)
<223> OTHER INFORMATION: Amino acid residues 75-78 are all Lys or all
      Asp, or are all absent. When all residues 75-78 are present,
      then any one or all of residues 79-84 can either be Lys or Asp
      to form, in combination with residues 75-78, a C-terminal
      polylysine or polyaspartate segment
<220> FEATURE:
<223> OTHER INFORMATION: of 4 to 10 residues in length.

<400> SEQUENCE: 51

Lys Cys Asn Thr Ala Thr Cys Ala Thr Gln Arg Leu Ala Asn Phe Leu
1               5                   10                  15

Val His Ser Ser Asn Asn Xaa Gly Ala Xaa Xaa Ser Ser Thr Asn Val
            20                  25                  30

Gly Ser Asn Thr Tyr Lys Cys Asn Thr Ala Thr Cys Ala Thr Gln Arg
            35                  40                  45

Leu Ala Asn Phe Leu Val His Ser Ser Asn Asn Xaa Gly Ala Xaa Xaa
            50                  55                  60

Ser Ser Thr Asn Val Gly Ser Asn Thr Tyr Xaa Xaa Xaa Xaa Xaa Xaa
65                  70                  75                  80

Xaa Xaa Xaa Xaa

<210> SEQ ID NO 52
<211> LENGTH: 57
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 are all Lys or all
    Asp.  Any one or all of residues 1-6 can either be absent or
    present as Lys or Asp to form, in combination with residues 7-10,
    a N-terminal polylysine or polyaspartate segment of 4 to 10
    residues in length.
<220> FEATURE:
<221> NAME/KEY: misc_feature
<222> LOCATION: (33)..(33)
<223> OTHER INFORMATION: Amino acid residues 33, 36, and 37 are Phe, Ile
    and Leu, respectively, in which zero, one, two, or three of
    residues 33, 36 and 37 is substituted with Pro, Asp, Glu, Lys,
    Gly, or Ser.
<220> FEATURE:
<221> NAME/KEY: misc_feature
<222> LOCATION: (36)..(37)
<223> OTHER INFORMATION: Amino acid residues 33, 36, and 37 are Phe,
    Ile and Leu, respectively,in which zero, one, two, or three of
    residues 33, 36 and 37 is substituted with Pro, Asp, Glu, Lys,
    Gly, or Ser.
<220> FEATURE:
<221> NAME/KEY: misc_feature
<222> LOCATION: (48)..(69)
<223> OTHER INFORMATION: Amino acids 48-51 are all Lys or all Asp.  Any
    one or all of residues 52-57 can either be absent or present as
    Lys or Asp to form, in combination with residues 66-69, a
    C-terminal polylysine or polyaspartate segment of 4 to 10 residues
    in length.

<400> SEQUENCE: 52

Xaa Xaa Xaa Xaa Xaa Xaa Xaa Xaa Xaa Xaa Lys Cys Asn Thr Ala Thr
1               5                   10                  15

Cys Ala Thr Gln Arg Leu Ala Asn Phe Leu Val His Ser Ser Asn Asn
            20                  25                  30

Xaa Gly Ala Xaa Xaa Ser Ser Thr Asn Val Gly Ser Asn Thr Tyr Xaa
        35                  40                  45

Xaa Xaa Xaa Xaa Xaa Xaa Xaa Xaa Xaa
    50                  55

<210> SEQ ID NO 53
<211> LENGTH: 94
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: Amino acid residues 7-10 are all Lys or all
    Asp.  Any one or all of residues 1-6 can either be absent or
    present as Lys or Asp to form, in combination with residues
    7-10, a N-terminal polylysine or polyaspartate segment of 4 to 10
    residues in length.
<220> FEATURE:
<221> NAME/KEY: misc_feature
<222> LOCATION: (33)..(33)
<223> OTHER INFORMATION: Amino acid residues 33, 36, 37 and residues 70,
    73, 74 are the same and are Phe, Ile, and Leu, respectively, in
    which zero, one, two, or three of residues 33, 36, and 37 and
    the same zero, one, two, or three of residues 70, 73, 74 is
    substituted with Pro, Asp,
<220> FEATURE:
<223> OTHER INFORMATION: Glu, Lys, Gly, or Ser.
<220> FEATURE:

```
<221> NAME/KEY: misc_feature
<222> LOCATION: (36)..(37)
<223> OTHER INFORMATION: Amino acid residues 33, 36, 37 and residues 70,
      73, 74 are the same and are Phe, Ile, and Leu, respectively, in
      which zero, one, two, or three of residues 33, 36, and 37 and the
      same zero, one, two, or three of residues 70, 73, 74 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (70)..(70)
<223> OTHER INFORMATION: Amino acid residues 33, 36, 37 and residues 70,
      73, 74 are the same and are Phe, Ile, and Leu, respectively, in
      which zero, one, two, or three of residues 33, 36, and 37 and the
      same zero, one, two, or three of residues 70, 73, 74 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (73)..(74)
<223> OTHER INFORMATION: Amino acid residues 33, 36, 37 and residues 70,
      73, 74 are the same and are Phe, Ile, and Leu, respectively, in
      which zero, one, two, or three of residues 33, 36, and 37 and the
      same zero, one, two, or three of residues 70, 73, 74 is
      substituted with Pro, Asp,
<220> FEATURE:
<223> OTHER INFORMATION: Glu, Lys, Gly, or Ser.
<220> FEATURE:
<221> NAME/KEY: misc_feature
<222> LOCATION: (84)..(94)
<223> OTHER INFORMATION: Amino acids 84-88 are all Lys or all Asp.  Any
      one or all of residues 89-94 can either be absent or present as
      Lys or Asp to form, in combination with residues 85-88, a
      C-terminal polylysine or polyaspartate segment of 4 to 10 residues
      in length.

<400> SEQUENCE: 53

Xaa Xaa Xaa Xaa Xaa Xaa Xaa Xaa Xaa Xaa Lys Cys Asn Thr Ala Thr
 1               5                  10                  15

Cys Ala Thr Gln Arg Leu Ala Asn Phe Leu Val His Ser Ser Asn Asn
            20                  25                  30

Xaa Gly Ala Xaa Xaa Ser Ser Thr Asn Val Gly Ser Asn Thr Tyr Lys
        35                  40                  45

Cys Asn Thr Ala Thr Cys Ala Thr Gln Arg Leu Ala Asn Phe Leu Val
50                  55                  60

His Ser Ser Asn Asn Xaa Gly Ala Xaa Xaa Ser Ser Thr Asn Val Gly
65                  70                  75                  80

Ser Asn Thr Tyr Xaa Xaa Xaa Xaa Xaa Xaa Xaa Xaa Xaa
                85                  90

<210> SEQ ID NO 54
<211> LENGTH: 140
<212> TYPE: PRT
<213> ORGANISM: Homo sapiens

<400> SEQUENCE: 54

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
```

-continued

```
                65                  70                  75                  80
Thr Val Glu Gly Ala Gly Ser Ile Ala Ala Thr Gly Phe Val Lys
            85                  90                  95
Lys Asp Gln Leu Gly Lys Asn Glu Gly Ala Pro Gln Gly Ile
        100                 105                 110
Leu Glu Asp Met Pro Val Asp Pro Asn Glu Ala Tyr Glu Met Pro
    115                 120                 125
Ser Glu Glu Gly Tyr Gln Asp Tyr Glu Pro Glu Ala
    130                 135                 140

<210> SEQ ID NO 55
<211> LENGTH: 140
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: One or more of the three sets of valine
      residues, represented as Xaa residue sets (1) 37 and 40; (2) 48,
      49, and 52; and (3) 70, 71, and 74, can be substituted with either
      all Glu, all Asp, all Pro, or all Lys.
<220> FEATURE:
<221> NAME/KEY: misc_feature
<222> LOCATION: (40)..(40)
<223> OTHER INFORMATION: One or more of the three sets of valine
      residues, represented as Xaa residue sets (1) 37 and 40; (2) 48,
      49, and 52; and (3) 70, 71, and 74, can be substituted with either
      all Glu, all Asp, all Pro, or all Lys.
<220> FEATURE:
<221> NAME/KEY: misc_feature
<222> LOCATION: (48)..(49)
<223> OTHER INFORMATION: One or more of the three sets of valine
      residues, represented as Xaa residue sets (1) 37 and 40; (2) 48,
      49, and 52; and (3) 70, 71, and 74, can be substituted with either
      all Glu, all Asp, all Pro, or all Lys.
<220> FEATURE:
<221> NAME/KEY: misc_feature
<222> LOCATION: (52)..(52)
<223> OTHER INFORMATION: One or more of the three sets of valine
      residues, represented as Xaa residue sets (1) 37 and 40; (2) 48,
      49, and 52; and (3) 70, 71, and 74, can be substituted with either
      all Glu, all Asp, all Pro, or all Lys.
<220> FEATURE:
<221> NAME/KEY: misc_feature
<222> LOCATION: (70)..(71)
<223> OTHER INFORMATION: One or more of the three sets of valine
      residues, represented as Xaa residue sets (1) 37 and 40; (2) 48,
      49, and 52; and (3) 70, 71, and 74, can be substituted with either
      all Glu, all Asp, all Pro, or all Lys.
<220> FEATURE:
<221> NAME/KEY: misc_feature
<222> LOCATION: (74)..(74)
<223> OTHER INFORMATION: One or more of the three sets of valine
      residues, represented as Xaa residue sets (1) 37 and 40; (2) 48,
      49, and 52; and (3) 70, 71, and 74, can be substituted with either
      all Glu, all Asp, all Pro, or all Lys.

<400> SEQUENCE: 55

Met Asp Val Phe Met Lys Gly Leu Ser Lys Ala Lys Glu Gly Val Val
1               5                  10                  15
Ala Ala Ala Glu Lys Thr Lys Gln Gly Val Ala Glu Ala Gly Lys
            20                  25                  30
Thr Lys Glu Gly Xaa Leu Tyr Xaa Gly Ser Lys Thr Lys Glu Gly Xaa
        35                  40                  45
Xaa His Gly Xaa Ala Thr Val Ala Glu Lys Thr Lys Glu Gln Val Thr
    50                  55                  60
Asn Val Gly Gly Ala Xaa Xaa Thr Gly Xaa Thr Ala Val Ala Gln Lys
```

```
                65                  70                  75                  80
Thr Val Glu Gly Ala Gly Ser Ile Ala Ala Ala Thr Gly Phe Val Lys
                    85                  90                  95
Lys Asp Gln Leu Gly Lys Asn Glu Glu Gly Ala Pro Gln Glu Gly Ile
                    100                 105                 110
Leu Glu Asp Met Pro Val Asp Pro Asn Glu Ala Tyr Glu Met Pro
            115                 120                 125
Ser Glu Glu Gly Tyr Gln Asp Tyr Glu Pro Glu Ala
    130                 135                 140
```

What is claimed is:

1. An isolated polypeptide consisting of SEQ ID NO:55 in which two or more of the following sets, (i) residues 37 and 40, (ii) residues 48, 49, and 52, and (iii) residues 70, 71, and 74, are substituted with all Glu, all Asp, all Pro, all Lys, all Gly, or all Ser residues.

2. The isolated polypeptide of claim 1, wherein all residues are D-amino acid residues.

3. The isolated polypeptide of claim 1, which consists of SEQ ID NO:55 in which the following sets of residues (i) residues 37 and 40 (ii) residues 48, 49, and 52, and (iii) residues 70, 71, and 74, are substituted with all Glu, all Asp, all Pro, all Lys, all Gly, or all Ser residues.

4. An isolated peptide consisting of a 30 to 36 residue segment, wherein the peptide is residues 1-30 to 1-36 of SEQ ID NO: 55, alone or joined at its N-terminus and/or C-terminus to a polylysine or polyaspartate segment of 4-10 residues in length.

5. An isolated peptide consisting of a 30 to 66 residue segment, wherein the peptide is residues 75-140 to 111-140 of SEQ ID NO: 55, alone or joined at its N-terminus and/or C-terminus to a polylysine or polyaspartate segment of 4-10 residues in length.

6. A conjugate of the polypeptide or peptide according to any one of claims 1, 4, or 5 cross-linked to a polymer molecule.

7. The conjugate of claim 6, wherein said polymer molecule is a peptide comprising a promiscuous T helper cell epitope.

8. An immunizing composition, comprising an immunizing effective amount of the polypeptide or peptide according to any one of claims 1, 4, or 5 or a conjugate thereof, and a pharmaceutically acceptable carrier, excipient, diluent, adjuvant, or auxiliary agent.

* * * * *